United States Patent [19]

Tatsuoka et al.

[11] Patent Number: 5,155,129
[45] Date of Patent: Oct. 13, 1992

[54] AGENTS FOR TREATING DISORDERS FROM CEREBRAL NEURO-DEGENERATION

[75] Inventors: Toshio Tatsuoka, Hyogo; Kayoko Nomura, Tochigi; Yuzo Nakagawa, Tochigi; Shizuo Nakamura, Osaka, all of Japan

[73] Assignee: Suntory Limited, Osaka, Japan

[21] Appl. No.: 662,105

[22] Filed: Feb. 28, 1991

[30] Foreign Application Priority Data

Jun. 6, 1990 [JP] Japan .................. 2-147709

[51] Int. Cl.$^5$ .............................. A61V 31/35
[52] U.S. Cl. ................................... 514/454
[58] Field of Search ......................... 514/454

[56] References Cited

U.S. PATENT DOCUMENTS 4,713,453  12/1987  Tatsuoka et al. .................. 544/60

*Primary Examiner*—S. J. Friedman
*Attorney, Agent, or Firm*—Cushman, Darby & Cushman

[57] ABSTRACT

A therapeutic agent for alleviating disorders caused by nerve cell degeneration in the brain which contains a cyclopropachromen derivative represented by the following general formula (I):

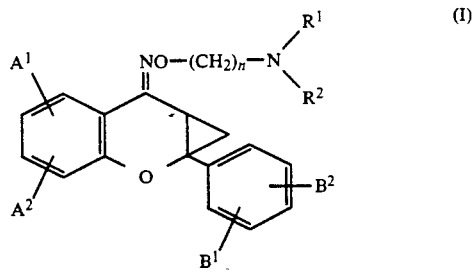

wherein
n is an integer of from 2 to 5;
the carbon atom in the —$(CH_2)_n$— moiety may be optionally substituted with a methyl group or a hydroxyl group;
$R^1$ and $R^2$ independently represent a hydrogen atom, an alkyl group having 1 to 5 carbon atoms, a phenyl group or an aralkyl group having 7 to 10 carbon atoms; or alternatively $R^1$ and $R^2$ form together with the nitrogen atom to which they are attached, a morpholino group, a thiomorpholino group, a pyrrolidinyl group, a piperidinyl group, a homopiperidinyl group, a piperazinyl group, a homopiperazinyl group, an N-alkylpiperazinyl group, N-alkylhomopiperazinyl group, an N-hydroxyalkylpiperazinyl group or a pyrrolidonyl group or alternatively $R^1$ and $R^2$ form together with the nitrogen atom to which they are attached, and further a carbon atom to which said nitrogen atom is bound, a pyrrolitidinyl group;
$A^1$ and $A^2$ independently represent a hydrogen atom, a hydroxyl group, a halogen atom, an optionally halogenated alkyl group having 1 to 5 carbon atoms, an optionally substituted alkoxy group, an acyloxy group, a carbamyloxy group or an optionally substituted carboxyl group;
and $B^1$ and $B^2$ independently represents a hydrogen atom, a halogen atom, a nitro group, a cyano group, an optionally halogenated alkyl group having 1 to 5 carbon atoms, an alkoxy group having 1 to 5 carbon atoms or an optionally substituted carboxyl group;
or a pharmaceutically acceptable salt thereof as an active ingredient, together with a pharmaceutical carrier or adjuvant.

6 Claims, No Drawings

AGENTS FOR TREATING DISORDERS FROM CEREBRAL NEURO-DEGENERATION

BACKGROUND OF THE INVENTION

1. Field of the Invention

This invention relates to an agent for treating disorders from cerebral neuro-degeneration comprising a specified cyclopropachromen derivative or a pharmaceutically acceptable salt thereof as an active ingredient.

2. Prior Art

Organic and functional disorders in the human brain which controls high grade mental actions and motor functions are critical diseases that concern not only the physical but also the mental well-being of a person. In a rapidly aging society, the development of effective methods of treating brain disorders as well as therapeutic drugs is of pressing importance. However, despite many years of studies conducted to unravel the functions of the brain, only a partial understanding has so far been achieved and an understanding of individual diseases, still less a comprehensive and systematic knowledge of the brain, has not yet been obtained.

While many brain diseases are known today, Alzheimer's disease (hereinafter sometimes abbreviated as AD) and senile dementia of the Alzheimer's type (hereinafter sometimes referred to as SDAT), both of which are progressive organic diseases of the brain that are characterized by lowered cognitive capabilities due to the degenerative atrophy of neurocytes in the brain, are becoming major social concerns requiring the implementation of effective care methods since the number of patients suffering from these diseases, especially in industrialized countries is rapidly increasing, and the progression of these diseases results in severe disability and ultimate death for those afflicted.

Under these circumstances, industrialized countries are engaged in nationwide projects for the establishment of effective methods for treating AD and SDAT. However, even the causes of the diseases have not been properly elucidated. Only the morphological changes that can be observed in the brain or the biochemical changes as the consequences have been partly unravelled, but no effective therapy has yet been established.

Cholinergic agents including choline precursors, cholinesterase inhibitors, etc. are being tested, on the basis of the cholinergic theory, in clinical fields as nosotropic agents for treating AD and SDAT. However, the evaluation on the utility of these therapeutics is varied and no single drug exhibits definite therapeutic effects.

Three basic methods may be conceived of to treat neurodegenetative diseases including AD and SDAT: (1) suppressing or preventing the degerative process of neurons; (2) compensating for the lost function of neurons with a drug; and (3) promoting the plasticity of remaining neurons to form a new neuro-circuit. The aforementioned cholinergic agents and cholinesterase inhibitors are within the class (2) since they are focused on the fact that, in a characteristic pathological symptom of AD and SDAT, cholinergic nerve fascicles that project from the basal forebrain to the cerebral cortex and the hippocampus undergo atrophic degeneration, yet acetylcholine receptors in the cerebral cortex and the hippocampus which are the cells that control those cholinergic nerve fascicles remain in a normal state. These drugs are expected to work effectively in the case of dysfunction of acetylcholine systems but no definite therapeutic effects are anticipated for diseases such as AD and SDAT which cannot be fully explained solely on the basis of the dysfunction of acetylcholine systems.

Aggravation of brain diseases could be prevented if the degenerative process of neurons could be suppressed as in (1). If a new neuron network could be formed by promoting the compensatory functional recovery of remaining neurons as in (3), not only could the progress of the diseases be prevented but also positive recovery of neurofunctions could reasonably be expected.

A drug that has been proposed in line with these approaches is a nerve growth factor (which is hereinafter referred to as "NGF"). NGF has long been known as a factor that is essential to the existence of sympathetic ganglion and sensory ganglion neurons in the peripheral nervous system, and hence extensive studies have been conducted on NGF. Recently, it has become clear that NGF also takes part in the existence and sustained functions of cholinergic neurons in the basal forebrain which are important to memory and learning. Thus the possibility of using NGF as an effective means of recovering part of the brain functions has been studied. However, NGF is a basic protein having a molecular weight of ca. 27,000 and the efforts to develop a direct method of compensatory therapy using NGF have not yet achieved a prospect for applicaton in clinical fields since they involve many problems to be solved as regards the methods of its production and administration.

Under these circumstances, increasing attention has recently been drawn by ganglioside as a non-peptide trophic factor like substance. For example, L. Facci et al. reported in J. Neurochem., 42, 299–305 (1985) that monosialoganglioside ($GM_1$) promoted the formation of nerve dendrites in cultured cells derived from mouse neuroblasts. L. F. Agnati et al., Acta Physiol. Scand., 119, 347–364 (1983) and G. Toffano et al., Brain Res., 296, 233–239 (1984) reported that $GM_1$ inhibited the degeneration of the cell body of nigra dopamine neurons that occurred after the removal of the cortex on one side of the brain. Further, G. Jonsson et al. reported in Neurosci. Lett. (Suppl.), 14, 185 (1983) that $GM_1$ worked suppressively on the decrease in 5-HT in the frontal and occipital lobes that was caused by pretreatment with 5,7-dihydroxytryptamine. These reports did not make it clear whether the action of ganglioside was direct or indirect in relation to the intermediary of the neurotrophic factor in NGF but they did show that ganglioside had the ability to either inhibit the degeneration of neurons or promote the compensatory functional recovery of a degenerated nerve circuit. Therefore, these observations suggest the possibility of new pharmaceutical therapy of AD and SDAT.

In fact, however, ganglioside is a glycosphingolipid containing sialic acid and $GM_1$, too, is a high-molecular weight compound that is the condensate of sialic acid, four saccharides and ceramide. Hence, the use of ganglioside as a drug for treating AD and SDAT involves several problems to be solved in terms of the methods of preparation and administration.

SUMMARY OF THE INVENTION

Under these circumstances, the present inventors conducted intensive studies and found compounds that were easy-to-synthesize. They are low molecular weight compounds that are capable of promoting the extension of nerve dendrites and that are as effective as NGF and ganglioside in suppressing the degenerative process of nerves or regenerating a damage nerve network to promote the recovery of its functions. The present invention has been accomplished on the basis of this finding and has as an object the provision of an entirely new therapeutic agent that relies upon the concept of recovering the functions of cerebral nerves by enhancing the plasticity of synapses and the level of learning activities.

DETAILED DESCRIPTION OF THE INVENTION

According to the present invention, a therapeutic agent for alleviating disorders resulting from cerebral neuro-degeneration which comprises a cyclopropachromen derivative represented by the following general formula (I):

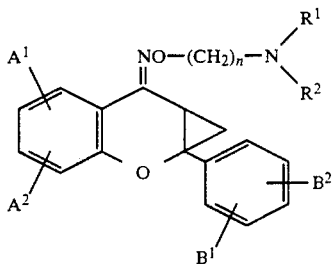

wherein
n is an integer of from 2 to 5;
the carbon atom in the —$(CH_2)_n$—moiety may be optionally substituted with a methyl group or a hydroxyl group;
$R^1$ and $R^2$ independently represent a hydrogen atom, an alkyl group having 1 to 5 carbon atoms, a phenyl group or an aralkyl group having 7 to 10 carbon atoms; or alternatively $R^1$ and $R^2$ form together with the nitrogen atom to which they are attached, a morpholino group, a thiomorpholino group, a pyrrolidinyl group, a piperidinyl group, a homopiperidinyl group, a piperazinyl group, a homopiperazinyl group, an N-alkylpiperazinyl group, N-alkylhomopiperazinyl group, an N-hydroxyalkylpiperazinyl group or a pyrrolidonyl group or alternatively $R^1$ and $R^2$ form together with the nitrogen atom to which they are attached, and further a carbon atom to which said nitrogen atom is bound, a pyrrolitidinyl group;
$A^1$ and $A^2$ independently represent a hydrogen atom, a hydroxyl group, a halogen atom, an optionally halogenated alkyl group having 1 to 5 carbon atoms, an optionally substituted alkoxy group, an acyloxy group, a carbamyloxy group or an optionally substituted carboxyl group; and
$B^1$ and $B^2$ independently represent a hydrogen atom, a halogen atom, a nitro group, a cyano group, an optionally halogenated alkyl group having 1 to 5 carbon atoms, an alkoxy group having 1 to 5 carbon atoms or an optionally substituted carboxyl group;

or a pharmaceutically acceptable salt thereof as an active ingredient is provided.

The term "halogen" as used herein includes fluoro, chloro, bromo or iodo, and fluoro, chloro and bromo are preferred.

The integer represented by n is preferably 2-4 and more preferably 2 or 3.

Examples of the alkyl group represented by $R^1$ and $R^2$ include methyl, ethyl, propyl, isopropyl, butyl, isobutyl, pentyl and neopentyl. Those having 1-3 carbon atoms such as methyl, ethyl, propyl and isopropyl are preferred.

Examples of the aralkyl group represented by $R^1$ and $R^2$ include benzyl, phenethyl, phenylpropyl, phenylbutyl, tolylmethyl, tolylethyl, tolylpropyl, pyridylmethyl and pyridylethyl.

When $R^1$ and $R^2$ form together with the nitrogen atom, to which they are attached, an N-alkylpiperazinyl group, Nalkyl-homopiperazinyl group or an N-hydroxyalkylpiperazinyl group, examples of the alkyl moiety include methyl, ethyl and propyl.

When $A^1$ and $A^2$ independently represent an optionally halogenated alkyl group, examples thereof include methyl, ethyl, propyl, isopropyl, butyl, isobutyl, pentyl, neopentyl and trifluoromethyl. Those having 1-3 carbon atoms such as methyl, ethyl, propyl and isopropyl are preferred.

When $A^1$ and $A^2$ independently represent an optionally substituted alkoxy group, examples of the substituent include phenyl and pyridyl.

When $A^1$ and $A^2$ independently represent an optionally substituted carboxyl group, examples of the substituent include methyl, ethyl, propyl, butyl, phenyl, benzyl, pyridyl and pyridylmethyl. Methyl and ethyl are preferred.

When $B^1$ and $B^2$ independently represent an optionally halogenated alkyl group, the alkyl group has preferably 1-5 carbon atoms. Examples of such groups include methyl, ethyl, propyl and trifluoromethyl.

When $B^1$ and $B^2$ independently represent an optionally substituted carboxyl group, examples of the substituent include methyl, ethyl, propyl, butyl, phenyl, benzyl, pyridyl and pyridylmethyl. Methyl and ethyl are preferred.

It should be understood that the compound of the present invention comprises several isomers as schematically illustrated below. Namely, there are two geometrical isomers (E-form and Z-form) at the oxime structure, and further, each of the geometrical isomers has two optical isomers. Each isomers can be separated by a conventional manner by way of, e.g. recrystallization, column chromatography, TLC, HPLC or by using a chemical substance commonly used in the separation of optical isomers.

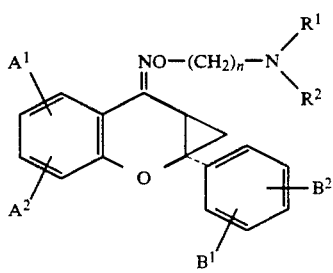

-continued

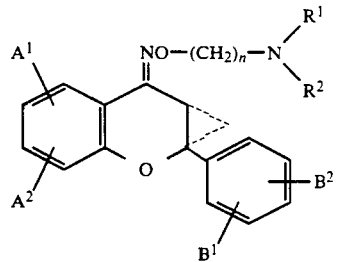

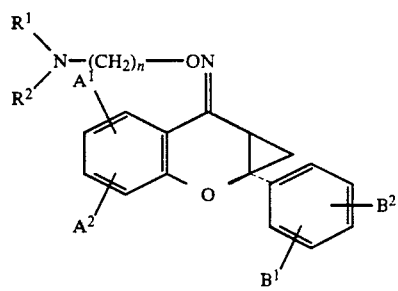

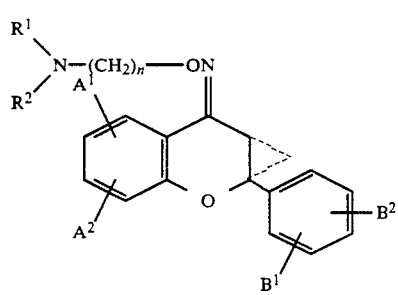

Typical examples of disorders resulting from cerebral neuro-degeneration to be treated with the use of the therapeutic agent of the present invention are progressive idiophrenic disorders, wherein cognitive capabilities deteriorate as a result of a degenerative atrophy of neurocytes in the brain, observed in Alzheimer's disease (AD) and senile demetia of an Alzheimer's type (SDAT).

Some of the cyclopropachromen derivatives represented by the above general formula (I) are described in Japanese Patent Laid-Open No. 198676/1987. However, these compounds are disclosed in the aforesaid Laid-Open patent as a therapeutic agent for postapopletic sequence, an antiamnestic agent and an antidepressant mainly based on the effect of preventing hypofunction of the brain in an ischemic state, namely, as a therapeutic agent for symptomatic treatment. In contrast thereto, the therapeutic agent of the present invention is a drug for causal treatment whereby degenerated cerebral neurocytes are restored and thus normalized. Therefore, the therapeutic agent of the present invention enables the treatment of kern-neurosis such as AD and SDAT caused by neuro-degeneration in the brain, differing from the case of the aforesaid therapeutic agent described in Japanese Patent Laid-Open No. 198676/1987.

Among the compounds of the general formula (I), novel ones may be synthesized in the following manner in accordance with a method described in Japanese Patent Laid-Open No. 198676/1987.

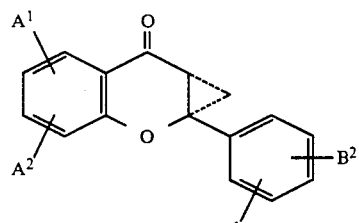

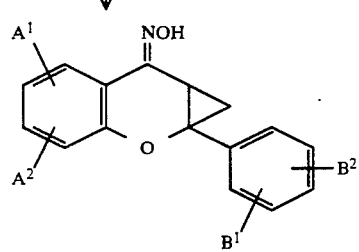

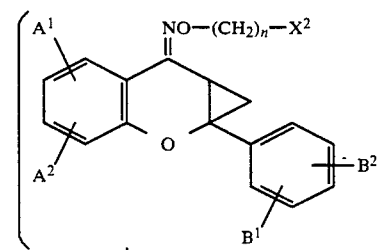

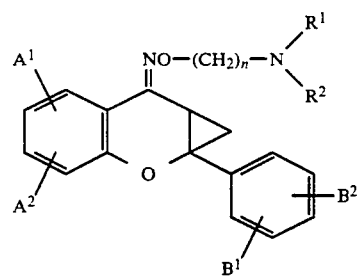

Namely, the compound of the general formula (II) is reacted with hydroxylamine hydrochloride in pyridine to give the compound (III). The compound (III) is then condensed with an aminohalide represented by the following formula:

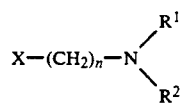

wherein
R$^1$, R$^2$ and —(CH$_2$)$_n$— are as defined above; and
X represents a halogen atom; to give the compound (I). Alternatively, the compound (III) is condensed with a bifunctional compound represented by the following formula:

wherein

—(CH$_2$)$_n$— is as defined above;

X$^1$ represents a halogen atom; and

X$^2$ represents a halogen atom or an epoxyethyl group;

to give the compound (IV). The compound (IV) is further reacted with an appropriate amine to give the compound (I).

The starting compound (II) to be used in the above synthesis is either a known compound reported by P. Bennett et al. [J. Chem. Soc., Perkin Trans., I, 2990 (1979)] or one which may be synthesized by a similar method.

The active ingredient of the present invention may be formulated into pharmaceutical compositions together with commonly known carriers either as such or in the form of a pharmaceutically acceptable salt, for example, an inorganic acid salt such as hydrochloride, sulfate, nitrate or phosphate, an organic acid salt such as acetate, propionate, butyrate, oxalate, malonate, succinate, maleate, fumarate, tartrate, citrate, malate, p-toluenesulfonate or methanesulfonate, or an alkali metal salt such as sodium or potassium salt when either A$^1$ or A$^2$ in the general formula (I) is a hydroxyl group. For example, the active ingredient may be formulated, optionally together with a common filler etc., into an appropriate preparation such as a capsule, tablet or injection and then orally or parenterally administered. These preparations may be obtained by, for example, the following methods. The active compound in the form of a powder is mixed with a filler such as lactose, starch or a derivative thereof or a cellulose derivative and then filled in a gelatin capsule to give a capsule. A tablet may be obtained by admixing the active compound together with an above-mentioned filler, a binder such as sodium carboxymethyl cellulose, alginic acid or gum arabic and water, optionally formulating into the kneaded mixture into granules, adding a lubricant such as talc or stearic acid thereto and then tableting the obtained mixture with a common compression tableting machine. In the case of parenteral administration by injection, the active compound is dissolved together with a dissolving aid in sterile distilled water or sterile physiological saline and then sealed in an ample to thereby give an injection preparation. The product may further contain a stabilizer or a buffer, if required.

The content of the active ingredient in the therapeutic agent may vary depending on the type of the disease, conditions, administration method and physical factors of the patient. In general, the content should be adjusted in such a manner as to give the active ingredient in an amount sufficient to alleviate the symptoms of the disease. For example, it may be administered to an adult in a dose of from approximately 0.1 to 1,000 mg, preferably from 1 to 500 mg, per day via oral administration, intravenous injection or application to mucosa.

In the following Reference Examples and Examples, the synthesis of the active ingredient compound of the present invention will be illustrated. In the Reference Examples given first, the preparation of a starting material to be used for synthesizing the active ingredient will be described. Each Reference Example is expressed in a combination of two numbers and the former number corresponds to the number of the above-mentioned general formulae (II) to (IV). [Namely, Reference Example II-1 shows the preparation of the starting material of the above-mentioned formula (II).]

REFERENCE EXAMPLE II-1

1a,7a-Dihydro-1a-phenylcyclopropa[b]chromen-7(1H)-one

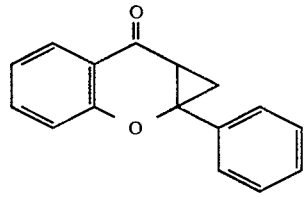

Although the method for synthesizing the titled compound is described by P. Bennett et al. [J. Chem. Soc., Perkin Trans. I, 2990 (1979)], no detailed description on a practical test method is given therein. By reference to their report, we have examined reaction conditions in detail and thus synthesized the titled compound by the following method.

11.2 g (50 mmol) of trimethylsulfoxonium iodide was dissolved in 100 ml of dimethylsulfoxide and 2.0 g (50 mmol) of sodium hydride (60% oil-dispersion) was added thereto by portions. The mixture was stirred at room temperature until no hydrogen evolved any more. To the obtained reaction mixture, was added a dimethylsulfoxide solution in which 11.1 g (50 mmol) of flavone had been dissolved. After stirring at room temperature for 2 hours and at 50° C. for 1 hour, the reaction mixture was poured onto ice/water and then extracted with ether. The extract was washed with water, dried and concentrated. The residue thus obtained was purified by silica gel chromatography (eluent: hexane:ethyl acetate=9:1) to give 6.01 g (yield: 48%) of the titled compound. The physicochemical data of the obtained product are shown in the following Table 1.

The compounds of Reference Examples II-2 to II-35 were each produced in the same manner as the one described in Reference Example II-1.

TABLE 1

| Reference Example | Structure | m.p. (°C.) | IR | | NMR |
|---|---|---|---|---|---|
| II-1 | 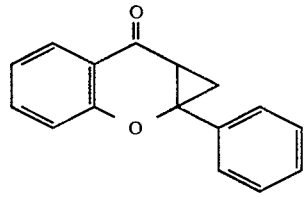 | 59.0–60.0 | 3050<br>1670<br>1605<br>1460<br>1320<br>1220<br>1025<br>750 | 2900<br>1640<br>1575<br>1380<br>1235<br>1130<br>960<br>690 | 1.73(t, 1H, J=6.6Hz)<br>2.06(dd, 1H, J=6.6Hz & 10.2Hz)<br>2.55(dd, 1H, J=6.6Hz & 10.2Hz)<br>7.03 –7.95(m, 9H) |

TABLE 1-continued

| Reference Example | Structure | m.p. (°C.) | IR | | NMR |
|---|---|---|---|---|---|
| II-2 | (4-F-phenyl fused chromanone with cyclopropane-phenyl) | 115–118 | 3000<br>1618<br>1300<br>1200<br>990<br>720 | 1670<br>1440<br>1260<br>1150<br>848 | 1.71(t, 1H, J=6.6Hz)<br>2.07(dd, 1H, J=6.6Hz) & 10.6Hz)<br>2.52(dd, 1H, J=6.6Hz & 10.6Hz)<br>6.7–6.85(m, 2H)7.3–7.5(m, 5H)<br>7.96(dd, 1H, J=6.6Hz & 8.6Hz) |
| II-3 | (6-Cl chromanone with cyclopropane-phenyl) | 102.0–103.5 | 3400<br>1670<br>1420<br>1220<br>975<br>860<br>755 | 3050<br>1600<br>1300<br>1065<br>900<br>810<br>690 | 1.73(dd, 1H, J=6.3Hz & 6.9Hz)<br>2.07(dd, 1H, J=6.9Hz & 10.9Hz)<br>2.52(dd, 1H, J=6.3Hz & 10.9Hz)<br>7.00–7.60(m, 7H)<br>7.87(d, 1H, J=8.2Hz) |
| II-4 | (6-Br chromanone with cyclopropane-phenyl) | 95–96 | 3000<br>1595<br>1298<br>962<br>720 | 1670<br>1418<br>1202 | 1.73(t, 1H, J=6.6Hz)<br>2.07(dd, 1H, J=6.6Hz & 10.9Hz)<br>2.53(dd, 1H, J=6.6Hz & 10.9Hz)<br>7.2–7.5(m, 7H)<br>7.80(d, 1H, J=8.6Hz) |
| II-5 | (6-H$_3$CO chromanone with cyclopropane-phenyl) | 115.0–116.5 | 3050<br>1650<br>1570<br>1440<br>1160<br>830<br>690 | 2990<br>1600<br>1490<br>1260<br>1080<br>740 | 1.67(t, 1H, J=6.3Hz),<br>1.99(dd, 1H, J=6.3Hz & 10.9Hz),<br>2.46(dd, 1H, J=6.3Hz & 10.9Hz),<br>3.83(s, 3H), 6.49(d, 1H, J=2.7Hz),<br>6.65(dd, 1H, J=2.7Hz & 8.9Hz)<br>7.26–7.48(m, 5H)<br>7.87(d, 1H, J=8.9Hz) |
| II-6 | (6-benzyloxy chromanone with cyclopropane-phenyl) | 123.0–124.5 | 3060<br>2940<br>1620<br>1440<br>1310<br>1180<br>700 | 3030<br>1670<br>1580<br>1390<br>1260<br>760 | 1.68(t, 1H, J=6.9Hz)<br>2.01(dd, 1H, J=6.9Hz & 11.6Hz)<br>2.46(dd, 1H, J=6.9Hz & 11.6Hz)<br>5.08(s, 2H)<br>6.55–7.88(m, 13H) |
| II-7 | (Cl chromanone with cyclopropane-phenyl) | 115–120 | 2990<br>1640<br>1565<br>1420<br>1280<br>1168<br>1100<br>955<br>860<br>680 | 1670<br>1598<br>1462<br>1345<br>1210<br>1128<br>985<br>912<br>815 | 1.74(t, 1H, J=6.6Hz)<br>2.08(dd, 1H, J=6.6Hz & 10.6Hz)<br>2.54(dd, 1H, J=6.6Hz & 10.6Hz) mx,1<br>7.02(d, 1H, J=8.6Hz)<br>7.3–7.5(m, 6H)<br>7.90(d, 1H, J=2.6Hz) |
| II-8 | (H$_3$CO chromanone with cyclopropane-phenyl) | 103–105 | 3020<br>2830<br>1610<br>1430<br>1345<br>1205<br>1030<br>865<br>750 | 2930<br>1660<br>1480<br>1380<br>1290<br>1080<br>970<br>835<br>690 | 1.70(t, 1H, J=6.6Hz),<br>2.04(dd, 1H, J=6.6Hz & 9.9Hz),<br>2.52(dd, 1H, J=6.6Hz & 9.9Hz)<br>3.82(s, 3H)<br>6.98–7.48(m, 8H) |

TABLE 1-continued

| Reference Example | Structure | m.p. (°C.) | IR | | NMR |
|---|---|---|---|---|---|
| II-9 | (2-methoxyphenyl ketone, 2-phenyl chromene cyclopropane) | oil | 3000 2830 1600 1470 1325 1230 1025 875 750 | 2930 1660 1570 1380 1260 1090 980 795 690 | 1.84(t, 1H, J=7.3Hz)<br>1.98(dd, 1H, J=7.3Hz & 9.9Hz)<br>2.58(dd, 1H, J=7.3Hz & 9.9Hz)<br>3.92(s, 3H),<br>6.57–6.68(m, 2H)<br>7.35–7.48(m, 6H) |
| II-10 | (3,4-dimethoxyphenyl ketone, 2-phenyl chromene cyclopropane) | 105–112 | 2920 1625 1498 1420 1280 1120 995 | 1670 1595 1440 1350 1260 1080 780 | 1.73(t, 1H, J=6.6Hz)<br>2.00–2.08(m, 1H)<br>2.50(dd, 1H, J=6.6Hz & 10.9Hz)<br>3.90(s, 3H), 3.94(s, 3H)<br>6.71(d, 1H, J=8.6Hz)<br>7.3–7.5(m, 5H)<br>7.71(d, 1H, J=8.6Hz) |
| II-11 | (4,5-dichlorophenyl ketone, 2-phenyl chromene cyclopropane) | 108–115 | 1675 1550 1405 1220 975 890 830 | 1598 1445 1260 1120 940 855 680 | 1.54(t, 1H, J=6.6Hz)<br>2.10(dd, 1H, J=6.6Hz & 10.6Hz)<br>2.53(dd, 1H, J=6.6Hz & 10.6Hz)<br>7.21(s, 1H), 7.3–7.5(m, 5H)<br>8.00(s, 1H) |
| II-12 | (5,6-dimethoxyphenyl ketone, 2-phenyl chromene cyclopropane) | 146–149 | 3000 1665 1500 1455 1380 1200 1080 1000 810 695 | 2940 1610 1470 1420 1280 1165 1030 960 755 | 1.66(t, 1H, J=6.6Hz)<br>2.01(dd, 1H, J=6.6Hz & 10.6Hz)<br>2.47(dd, 1H, J=6.6Hz & 10.6Hz)<br>3.90(s, 3H), 3.71(s, 3H)<br>6.52(s, 1H)<br>7.31–7.49(m, 6H) |
| II-13 | (5,6-dibenzyloxyphenyl ketone, 2-phenyl chromene cyclopropane) | 124–125 | 1660 1500 1370 1200 1000 820 740 | 1610 1445 1270 1080 865 760 695 | 1.64(t, 1H, J=6.6Hz)<br>1.99(dd, 1H, J=6.6Hz & 10.6Hz)<br>2.44(dd, 1H, J=6.6Hz & 10.6Hz)<br>5.15(s, 2H), 5.18(s, 2H)<br>6.56(s, 1H)<br>7.28–7.49(m, 16H) |
| II-14 | (phenyl ketone, 2-(2-methoxyphenyl) chromene cyclopropane) | 80–83 | 2900 1600 1380 1280 1230 1090 955 745 | 1670 1460 1315 1250 1120 1010 880 | 1.63(t, 1H, J=6.6Hz)<br>1.97(dd, 1H, J=6.6Hz & 10.6Hz)<br>2.41(dd, 1H, J=6.6Hz & 10.6Hz)<br>3.81(s, 3H), 6.94–7.51(m, 7H)<br>7.94(dd, 1H, J=2.0Hz & 7.2Hz) |
| II-15 | (phenyl ketone, 2-(2-methylphenyl) chromene cyclopropane) | 51–56 | 3050 1675 1580 1385 1230 1100 960 880 | 2940 1610 1465 1320 1130 1025 900 755 | 1.69(t, 1H, J=6.6Hz)<br>2.00(dd, 1H, J=6.6Hz & 11.2Hz)<br>2.43(s, 3H)<br>2.47(dd, 1H, J=6.6Hz & 11.2Hz)<br>6.94–7.52(m, 7H)<br>7.95(dd, 1H, J=2.0Hz & 7.9Hz) |

TABLE 1-continued

| Reference Example | Structure | m.p. (°C.) | IR | | NMR |
|---|---|---|---|---|---|
| II-16 | (chromanone cyclopropane with 3-chlorophenyl) | oil | 3050 1600 1460 1375 1255 1125 1015 885 | 1675 1570 1435 1320 1150 1080 965 855 | 1.77(t, 1H, J=7.3Hz)<br>2.04(dd, 1H, J=7.3Hz & 10.5Hz)<br>2.53(dd, 1H, J=7.3Hz & 10.5Hz)<br>7.06-7.57(m, 7H)<br>7.93(dd, 1H, J=1.3Hz & 7.9Hz) |
| II-17 | (chromanone cyclopropane with 3-methoxyphenyl) | 96-100 | 2950 1640 1580 1460 1320 1220 1125 850 755 | 1670 1600 1480 1430 1260 1155 1035 780 | 1.72(t, 1H, J=7.0Hz)<br>2.03(dd, 1H, J=7.0Hz & 10.8Hz)<br>2.53(dd, 1H, J=7.0Hz & 10.8Hz)<br>3.82(s, 3H), 6.87-7.53(m, 7H)<br>7.92(dd, 1H, J=2.0Hz & 7.9Hz) |
| II-18 | (chromanone cyclopropane with 3-methylphenyl) | 72-76 | 3000 1680 1600 1480 1345 1255 1200 1020 820 745 | 2900 1630 1575 1440 1280 1240 1150 980 780 680 | 1.72(t, 1H, J=6.2Hz)<br>2.05(dd, 1H, J=6.2Hz & 10.8Hz)<br>2.40(s, 3H)<br>2.52(dd, 1H, J=6.2Hz & 10.8Hz)<br>7.04-7.54(m, 7H)<br>7.93(dd, 1H, J=1.3Hz & 7.9Hz) |
| II-19 | (chromanone cyclopropane with 4-chlorophenyl) | 54-57 | 3000 1675 1500 1370 1225 1090 965 810 710 | 2900 1600 1460 1315 1145 1010 830 755 | 1.75(t, 1H, J=6.6Hz)<br>2.02(dd, 1H, J=6.6Hz & 11.2Hz)<br>2.51(dd, 1H, J=6.6Hz & 11.2Hz)<br>7.03-7.56(m, 7H)<br>7.93(dd, 1H, J=2.0Hz & 7.9Hz) |
| II-20 | (chromanone cyclopropane with 4-methoxyphenyl) | 99-104 | 2920 1670 1515 1380 1250 1175 1020 820 | 2820 1600 1460 1320 1230 1125 960 750 | 1.69(t, 1H, J=6.6Hz)<br>2.02(dd, 1H, J=6.6Hz & 10.6Hz)<br>2.49(dd, 1H, J=6.6Hz & 10.6Hz)<br>3.84(s, 3H)<br>6.93-7.53(m, 7H)<br>7.93(dd, 1H, J=2.0Hz & 7.9Hz) |
| II-21 | (chromanone cyclopropane with 4-methylphenyl) | 73-75 | 3010 1670 1460 1320 1125 1020 805 | 2900 1605 1380 1230 1100 960 750 | 1.71(t, 1H, J=6.6Hz)<br>2.03(dd, 1H, J=6.6Hz & 10.6Hz)<br>2.38(s, 3H)<br>2.50(dd, 1H, J=6.6Hz & 10.6Hz)<br>7.02-7.53(m, 7H)<br>7.93(dd, 1H, J=2.0Hz & 7.9Hz) |
| II-22 | (chromanone cyclopropane with 4-trifluoromethylphenyl) | 145-148 | 2950 1600 1460 1230 1110 1010 825 680 | 1675 1575 1320 1160 1065 970 755 | 1.83(t, 1H, J=6.6Hz)<br>2.07(dd, 1H, J=6.6Hz & 11.2Hz)<br>2.58(dd, 1H, J=6.6Hz & 11.2Hz)<br>7.07-7.71(m, 7H)<br>7.94(dd, 1H, J=1.3Hz & 7.6Hz) |

TABLE 1-continued

| Reference Example | Structure | m.p. (°C.) | IR | | NMR |
|---|---|---|---|---|---|
| II-23 | (chromanone cyclopropyl-4-CO₂CH₃-phenyl) | 88–90 | 2900<br>1665<br>1460<br>1310<br>1220<br>1100<br>965<br>760 | 1715<br>1600<br>1425<br>1280<br>1175<br>1000<br>830<br>740 | 1.82(t, 1H, J=6.6Hz)<br>2.10(dd, 1H, J=6.6Hz & 11.2Hz)<br>2.59(dd, 1H, J=6.6Hz & 11.2Hz)<br>3.94(s, 3H)<br>7.08–8.11(m, 8 H) |
| II-24 | (chromanone cyclopropyl-4-CN-phenyl) | 100–102 | 2220<br>1605<br>1378<br>1210<br>1100<br>965<br>820 | 1670<br>1460<br>1320<br>1122<br>1050<br>870 | 1.86(t, 1H, J=6.6Hz)<br>2.07(dd, 1H, J=6.6Hz & 11.2Hz)<br>2.59(dd, 1H, J=6.6Hz & 11.2Hz)<br>7.05–7.2(m, 2H), 7.5–7.6(m, 3H),<br>7.73(d, 2H, J=8.6Hz)<br>7.94(dd, 1H, J=2.0Hz & 7.6Hz) |
| II-25 | (chromanone cyclopropyl-4-NO₂-phenyl) | 157–160 | 3400<br>1610<br>1470<br>1320<br>1100<br>860<br>760 | 1675<br>1515<br>1350<br>1130<br>975<br>840<br>750 | 1.90(dd, 1H, J=6.6Hz & 7.3Hz)<br>2.12(dd, 1H, J=10.6Hz & 7.3Hz)<br>2.63(dd, 1H, J=6.6Hz & 10.6Hz)<br>7.14(m, 2H)7.5–7.6(m, 1H)<br>7.61(d, 2H, J=9.2Hz)<br>7.95(dd, 1H, J=1.3Hz & 7.3Hz)<br>8.29(d, 2H, J=9.2Hz) |
| II-26 | (chromanone cyclopropyl-3,4-diCl-phenyl) | 101–103 | 1665<br>1460<br>1318<br>1120<br>960 | 1600<br>1368<br>1190<br>1020 | 1.78(t, 1H, J=6.6Hz)<br>2.02(dd, 1H, J=6.6Hz & 10.9Hz)<br>2.52(dd, 1H, J=6.6Hz & 10.9Hz)<br>7.05–7.15(m, 2H)7.2–7.3(m, 1H)<br>7.45–7.6(m, 3H)<br>7.93(dd, 1H, J=1.3Hz & 7.9Hz) |
| II-27 | (chromanone cyclopropyl-3,4-diOCH₃-phenyl) | 107–110 | 2850<br>1630<br>1500<br>1405<br>1260<br>1120<br>740 | 1680<br>1575<br>1440<br>1330<br>1140<br>1010 | 1.70(t, 1H, J=6.6Hz)<br>2.03(dd, 1H, J=6.6Hz & 11.2Hz)<br>2.50(dd, 1H, J=6.6Hz & 11.2Hz)<br>3.91(s, 3H), 3.92(s, 3H)<br>6.88–7.54(m, 6H)<br>7.94(dd, 1H, J=2.0Hz & 7.9Hz) |
| II-28 | (6-Cl-chromanone cyclopropyl-4-Cl-phenyl) | 121–122 | 3090<br>1600<br>1495<br>1300<br>1095<br>1010<br>815 | 1675<br>1565<br>1425<br>1220<br>1070<br>980 | 1.74(t, 1H, J=6.6Hz)<br>2.04(dd, 1H, J=6.6Hz & 11.2Hz)<br>2.50(dd, 1H, J=6.6Hz & 11.2Hz)<br>7.05–7.15(m, 2H)7.3–7.5(m, 4H)<br>7.83–7.95(m, 1H) |
| II-29 | (6-Cl-chromanone cyclopropyl-4-NO₂-phenyl) | 176–178 | 3080<br>1680<br>1510<br>1340<br>1220<br>1090<br>900<br>750 | 3050<br>1600<br>1420<br>1290<br>1135<br>980<br>840 | 1.87(dd, 1H, J=6.7Hz & 7.4Hz)<br>2.13(dd, 1H, J=7.4Hz & 11.2Hz)<br>2.62(dd, 1H, J=6.7Hz & 11.2Hz)<br>7.09(dd, 1H, J=2.2Hz & 8.2Hz)<br>7.13(d, 1H, J=2.2Hz)<br>7.57(d, 2H, J=8.9Hz)<br>7.87(d, 1H, J=8.2Hz)<br>8.28(d, 2H, J=8.9Hz) |

TABLE 1-continued

| Reference Example | Structure | m.p. (°C.) | IR | | NMR |
|---|---|---|---|---|---|
| II-30 | 4-F-benzofuranyl cyclopropyl 4-F-phenyl ketone | 77–82 | 3090 1620 1440 1300 1230 1125 995 830 750 | 1670 1515 1375 1260 1150 1100 850 810 | 1.73(t, 1H, J=6.6Hz) 2.03(dd, 1H, J=6.6Hz & 10.7Hz) 2.49(dd, 1H, J=6.6Hz & 10.7Hz) 6.70–6.85(m, 2H) 7.09–7.48(m, 4H) 7.96(dd, 1H, J=6.6Hz & 9.2Hz) |
| II-31 | 4-Cl-benzofuranyl cyclopropyl 4-F-phenyl ketone | 136–138 | 1665 1515 1310 1140 980 835 800 | 1605 1425 1220 1095 910 820 | 1.72(t, 1H, 6.6Hz) 2.03(dd, 1H, J=6.6 & 10.6Hz) 2.49(dd, 1H, J=6.6 & 10.6Hz) 7.1(m, 4H) 7.4(m, 2H) 7.87(d, 1H, J=9.2Hz) |
| II-32 | 4-Cl-benzofuranyl cyclopropyl 4-Br-phenyl ketone | 125–127 | 1675 1565 1425 1225 1000 905 810 | 1605 1495 1300 1095 980 865 770 | 1.74(t, 1H, J=6.6Hz) 2.03(dd, 1H, J=6.6 & 11.2Hz) 2.49(dd, 1H, J=6.6 & 11.2Hz) 7.06(m, 2H) 7.31(d, 2H, J=8.6Hz) 7.56(d, 2H, J=8.6Hz) 7.87(d, 1H, J=8.6Hz) |
| II-33 | 4-Br-benzofuranyl cyclopropyl 4-F-phenyl ketone | 129–131 | 1670 1520 1305 1225 975 830 | 1595 1420 1235 1165 905 800 | 1.72(dd, 1H, J=6.6 & 7.3Hz) 2.03(dd, 1H, J=7.3 & 11.2Hz) 2.49(dd, 1H, J=6.6 & 11.2Hz) 7.1(m, 2H) 7.2(m, 2H) 7.4(m, 2H) 7.79(d, 1H, J=8.6Hz) |
| II-34 | 4-Br-benzofuranyl cyclopropyl 4-Cl-phenyl ketone | 144–146 | 1670 1500 1300 1095 975 865 | 1595 1420 1220 1010 900 | 1.74(dd, 1H, J=6.6 & 7.3Hz) 2.03(dd, 1H, J=7.3 & 11.2Hz) 2.50(dd, 1H, J=6.6 & 11.2Hz) 7.2(m, 2H) 7.4(m, 4H) 7.79(d, 1H, J=7.9Hz) |
| II-35 | 4-Br-benzofuranyl cyclopropyl 4-Br-phenyl ketone | 153–154 | 1670 1495 1300 1090 975 810 | 1595 1420 1220 1010 900 | 1.74(dd, 1H, J=6.6 & 7.3Hz) 2.03(dd, 1H, J=7.3 & 11.2Hz) 2.50(dd, 1H, J=6.6 & 11.2Hz) 7.2(m, 4H) 7.56(d, 2H, J=8.6Hz) 7.79(d, 1H, J=8.6Hz) |

REFERENCE EXAMPLE III-1

1a,
7a-Dihydro-7(1H)-hydroxyimino-1a-phenylcyclopropa[b]chromen

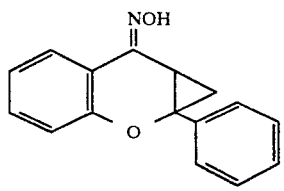

2.36 g (10 mmol) of the compound of Reference Example II-1 was dissolved in 80 ml of pyridine. 2.78 g (40 mmol) of hydroxylamine hydrochloride was added thereto and the obtained mixture was stirred at 55° C. for 2 hours. The reaction mixture was concentrated, diluted with water and then extracted with chloroform. The extract was washed with water, dried and concentrated. The residue thus obtained was purified by silica gel chromatography (eluent: hexane:ethyl acetate=9:1) to give 2.31 g (yield: 92.1%) of the titled compound. The physicochemical data of this product are shown in the following Table 2. Table 2 further shows the compounds of Reference Examples III-2 to III-35 which were produced by reacting the compounds of Reference Examples II with hydroxylamine hydrochloride followed by the treatment as the aforesaid manner.

TABLE 2

| Reference Example | Structure | m.p. (°C.) | IR | | NMR |
|---|---|---|---|---|---|
| III-1 | (structure) | 114–115 | 3250 2930 1600 1480 1380 1300 1220 1035 915 735 | 3050 1660 1565 1450 1330 1250 1105 975 880 690 | 1.65(t, 1H, J=6.6Hz) 1.93(dd, 1H, J=6.6Hz & 10.2Hz) 3.13(dd, 1H, J=6.6Hz & 10.2Hz) 6.96–7.79(m, 9H)8.62(s, 1H) |
| III-2 | (structure) | 141–143 | 3550 1608 1430 1200 998 715 | 3010 1500 1260 1148 848 | 1.63(t, 1H, J=6.6Hz) 1.94(dd, 1H, J=6.6Hz & 10.6Hz) 3.11(dd, 1H, J=6.6Hz & 10.6Hz) 6.65–6.76(m, 2H)7.3–7.5(m, 5H) 7.7–7.8(m, 1H) |
| III-3 | (structure) | 153–155 | 3200 3050 1600 1475 1410 1220 1010 900 790 680 | 3150 1640 1560 1440 1305 1070 980 860 740 | 1.61(dd, 1H, J=8.6Hz & 10.6Hz) 1.94(dd, 1H, J=6.6Hz & 10.6Hz) 3.11(dd, 1H, J=8.6Hz & 6.6Hz) 6.96(dd, 1H, J=2.3Hz & 8.6Hz) 7.02(d, 1H, J=2.3Hz) 7.28–7.50(m, 5H) 7.70(d, 1H, J=8.6Hz)7.99(br.s, 1H) |
| III-4 | (structure) | 164–166 | 3200 1598 1480 1305 980 | 1640 1560 1410 1218 920 | 1.61(t, 1H, J=6.6Hz) 1.93(dd, 1H, J=6.6Hz & 10.6Hz) 3.09(dd, 1H, J=6.6Hz & 10.6Hz) 7.10(m, 1H)7.12–7.13(m, 1H) 7.25–7.5(m, 5H) 7.65(d, 1H, J=8.6Hz) |
| III-5 | (structure) | oil | 3200 2820 1565 1435 1380 1160 1020 905 745 | 3050 1615 1500 1420 1260 1085 990 825 690 | 1.62(t, 1H, J=6.6Hz) 1.91(dd, 1H, J=6.6Hz & 10.6Hz) 3.09(dd, 1H, J=6.6Hz & 10.6Hz) 3.80(s, 3H)6.49–7.70 (m, 8H) 8.62(m, 1H) |

TABLE 2-continued

| Reference Example | Structure | m.p. (°C.) | IR | NMR |
|---|---|---|---|---|
| III-6 | 6-benzyloxy chromene oxime with phenyl on cyclopropane | 52–56 | 3400, 3050, 1610, 1500, 1450, 1430, 1380, 1260, 1235, 1165, 1140, 1090, 1020, 910, 830, 735, 695 | 1.62(t, 1H, J=6.9Hz) 1.91(dd, 1H, J=6.9Hz & 11.1Hz) 3.07(dd, 1H, J=6.9Hz & 11.1Hz) 5.04(s, 2H)6.57–7.72(m, 13H) |
| III-7 | 6-chloro chromene oxime with phenyl on cyclopropane | 161.5–163 | 3250, 1620, 1592, 1465, 1420, 1278, 1102, 1065, 1010, 970, 915, 870, 805, 685 | 1.62(t, 1H, J=6.6Hz) 1.93(dd, 1H, J=6.6Hz & 10.6Hz) 3.10(dd, 1H, J=6.6Hz & 10.6Hz) 6.93(d, 1H, J=9.2Hz)7.2–7.6(m, 6H) 7.76(d, 1H, J=2.6Hz) |
| III-8 | 6-methoxy chromene oxime with phenyl on cyclopropane | 142–145 | 3200, 3000, 1635, 1605, 1490, 1465, 1450, 1435, 1300, 1215, 1180, 1120, 1080, 1030, 980, 945, 860, 835, 760, 695 | 1.61(t, 1H, J=6.6Hz) 1.90(dd, 1H, J=6.6Hz & 10.6Hz) 3.09(dd, 1H, J=6.6Hz & 10.6Hz) 3.80(s, 3H)6.93–7.50(m, 8H) |
| III-9 | 8-methoxy chromene oxime with phenyl on cyclopropane | 213–217 | 3150, 1590, 1565, 1460, 1430, 1320, 1285, 1260, 1230, 1090, 1010, 985, 935, 910, 890, 780, 745, 720 | 1.66(t, 1H, J=6.6Hz) 1.85(dd, 1H, J=6.6Hz & 10.6Hz) 3.36(dd, 1H, J=6.6Hz & 10.6Hz) 3.91(s, 3H) 6.57–6.66(m, 2H)7.20–7.50(m, 6H) |
| III-10 | 7,8-dimethoxy chromene oxime with phenyl on cyclopropane | 152–153 | 3200, 2910, 1640, 1600, 1495, 1450, 1422, 1375, 1335, 1280, 1255, 1220, 1140, 1105, 1090, 1015, 960, 855, 825, 750, 715 | 1.66(t, 1H, J=6.6Hz) 1.92(dd, 1H, J=6.6Hz & 10.6Hz) 3.14(dd, 1H, J=6.6Hz & 10.6Hz) 3.89(s, 6H)6.62(d, 1H, J=8.6Hz) 7.25–7.55(m, 5H)7.77(m, 1H) |
| III-11 | 6,7-dichloro chromene oxime with phenyl on cyclopropane | 136.5–137.5 | 1625, 1405, 1200 | 1.60(t, 1H, J=6.6Hz) 1.94(dd, 1H, J=6.6Hz & 10.6Hz) 3.08(dd, 1H, J=6.6Hz & 10.6Hz) 7.13(s, 1H)7.25–7.5(m, 5H) 7.87(s, 1H) |
| III-12 | 6,7-dimethoxy chromene oxime with phenyl on cyclopropane | 194–195 | 3200, 2820, 1615, 1505, 1440, 1420, 1380, 1305, 1255, 1210, 1160, 1080, 1035, 1010, 900, 840, 765, 690 | 1.60(t, 1H, J=6.6Hz) 2.13(dd, 1H, J=6.6Hz & 10.6Hz) 2.92(dd, 1H, J=6.6Hz & 10.6Hz) 3.89(s, 3H), 3.92(s, 3H) 6.56(s, 1H)7.27–7.58(m, 6H) |

TABLE 2-continued

| Reference Example | Structure | m.p. (°C.) | IR | | NMR |
|---|---|---|---|---|---|
| III-13 | (3,4-dibenzyloxyphenyl, 2-phenyl cyclopropyl chromene oxime structure) | 160–161 | 3100 1610 1440 1300 1200 1080 1000 900 750 | 2850 1500 1375 1250 1170 1040 930 840 690 | 1.62(t, 1H, J=6.6Hz) 2.08(dd, 1H, J=6.6Hz & 10.5Hz) 2.90(dd, 1H, J=6.6Hz & 10.5Hz) 5.06(s, 2H), 5.12(s, 2H) 6.57(s, 1H)7.22–7.54(m, 16H) |
| III-14 | (2-methoxyphenyl substituted chromene oxime) | 222–224 | 3150 1635 1575 1460 1330 1225 1020 920 755 | 2900 1600 1485 1380 1280 1125 975 900 | 1.52(t, 1H, J=6.6Hz) 1.84(dd, 1H, J=6.6Hz & 10.6Hz) 2.99(dd, 1H, J=6.6Hz & 10.6Hz) 3.82(s, 3H) 6.80–7.50(m, 7H) 7.58(br.s, 1H) 7.79(d, 1H, J=7.3Hz) |
| III-15 | (2-methylphenyl substituted chromene oxime) | 179–183 | 3200 1605 1480 1380 1320 1130 975 900 740 | 1630 1570 1455 1335 1220 1020 920 760 | 1.58(t, 1H, J=6.6Hz) 1.87(dd, 1H, J=6.6Hz & 10.6Hz) 2.38(s, 3H) 3.07(dd, 1H, J=6.6Hz & 10.6Hz) 6.86–7.47(m, 7H) 7.55(br.s, 1H) 7.79(dd, 1H, J=2.0Hz & 7.3Hz) |
| III-16 | (3-chlorophenyl substituted chromene oxime) | oil | 3100 1595 1470 1370 1250 1120 1020 900 820 | 1620 1560 1410 1310 1220 1070 970 850 750 | 1.66(dd, 1H, J=6.6Hz & 7.3Hz) 1.89(dd, 1H, J=7.3Hz & 10.6Hz) 3.11(dd, 1H, J=6.6Hz & 10.6Hz) 6.78–7.50(m, 7H) 7.78(dd, 1H, J=2.0Hz & 6.6Hz) |
| III-17 | (3-methoxyphenyl substituted chromene oxime) | oil | 3200 1600 1480 1430 1230 1045 980 840 740 | 2900 1580 1450 1375 1125 1030 905 760 680 | 1.64(t, 1H, J=6.6Hz) 1.92(dd, 1H, J=6.6Hz & 10.6Hz) 3.17(dd, 1H, J=6.6Hz & 10.6Hz) 3.83(s, 3H) 6.85–7.36(m, 7H) 7.77(d, 1H, J=7.9Hz) |
| III-18 | (3-methylphenyl substituted chromene oxime) | oil | 3250 2900 1605 1455 1325 1255 1185 980 850 | 3040 1625 1480 1380 1310 1230 1125 910 760 | 1.63(t, 1H, J=6.6Hz) 1.94(dd, 1H, J=6.6Hz & 10.6Hz) 2.39(s, 3H) 3.14(dd, 1H, J=6.6Hz & 10.6Hz) 6.76–7.36(m, 7H) 7.76(d, 1H, J=7.9Hz) |
| III-19 | (4-chlorophenyl substituted chromene oxime) | 175–177 | 3200 1635 1570 1385 1305 1125 980 890 760 | 2890 1595 1450 1330 1220 1085 920 820 740 | 1.66(t, 1H, J=6.6Hz) 1.88(dd, 1H, J=6.6Hz & 10.5Hz) 3.11(dd, 1H, J=6.6Hz & 10.5Hz) 6.97–7.40(m, 7H) 7.76(dd, 1H, J=1.3Hz & 7.9Hz) |

TABLE 2-continued

| Reference Example | Structure | m.p. (°C.) | IR | | NMR |
|---|---|---|---|---|---|
| III-20 | (chromene cyclopropane with NOH, Ar-OCH₃) | 186–190 | 2920 1510 1300 1170 1020 910 765 | 1600 1445 1245 1125 970 810 740 | 1.59(t, 1H, J=6.6Hz)<br>1.86(dd, 1H, J=6.6Hz & 10.5Hz)<br>3.07(dd, 1H, J=6.6Hz & 10.5Hz)<br>3.83(s, 3H)<br>6.92–7.44(m, 7H)<br>7.77(dd, 1H, J=1.3Hz & 7.9Hz) |
| III-21 | (chromene cyclopropane with NOH, Ar-CH₃) | 167–169 | 3150 1635 1570 1370 1300 1220 1105 975 755 | 2900 1600 1450 1330 1250 1120 1020 800 725 | 1.61(t, 1H, J=6.6Hz)<br>1.89(dd, 1H, J=6.6Hz & 9.9Hz)<br>2.37(s, 3H)<br>3.09(dd, 1H, J=6.6Hz & 9.9Hz)<br>6.96–7.39(m, 7H)<br>7.77(dd, 1H, J=1.3Hz & 8.3Hz) |
| III-22 | (chromene cyclopropane with NOH, Ar-CF₃) | 155–158 | 3240 1620 1570 1320 1160 1065 900 760 | 3030 1600 1455 1230 1120 1010 825 730 | 1.73(dd, 1H, J=6.6Hz & 7.3Hz)<br>1.94(dd, 1H, J=7.3Hz & 10.6Hz)<br>3.21(dd, 1H, J=6.6Hz & 10.6Hz)<br>6.98–7.67(m, 7H)<br>7.76(dd, 1H, J=2.0Hz & 7.2Hz)<br>9.26(br.s, 1H) |
| III-23 | (chromene cyclopropane with NOH, Ar-CO₂CH₃) | oil | 3350 2940 1610 1435 1280 1180 1010 840 735 | 3050 1720 1455 1310 1230 1110 900 765 | 1.71(t, 1H, J=6.6Hz)<br>1.94(dd, 1H, J=6.6Hz & 10.6Hz)<br>3.22(dd, 1H, J=6.6Hz & 10.6Hz)<br>3.92(s, 3H)<br>6.96–8.08(m, 8H)<br>9.80(br.s, 1H) |
| III-24 | (chromene cyclopropane with NOH, Ar-CN) | 184–187 | 2210 1605 1370 1210 1005 900 | 1620 1455 1305 1100 970 | 1.76(t, 1H, J=6.6Hz)<br>1.94(dd, 1H, J=6.6Hz & 10.6Hz)<br>3.17(dd, 1H, J=6.6Hz & 10.6Hz)<br>6.95–7.1(m, 2H)7.3–7.45(m, 1H)<br>7.56(d, 2H, J=8.6Hz)<br>7.70(d, 2H, J=8.6Hz)<br>7.78(dd, 1H, J=1.4Hz & 8.6Hz) |
| III-25 | (chromene cyclopropane with NOH, Ar-NO₂) | 182–185 | 3250 1580 1460 1320 1235 980 850 | 1605 1520 1355 1255 1105 970 745 | 1.80(dd, 1H, J=6.6Hz & 7.3Hz)<br>1.99(dd, 1H, J=10.6Hz & 7.3Hz)<br>3.23(dd, 1H, J=6.6Hz & 10.6Hz)<br>7.03(m, 2H), 7.35(m, 1H)<br>7.61(d, 2H, J=8.6Hz)<br>7.78(dd, 1H, J=1.3Hz & 7.9Hz)<br>8.04(s, 1H), 8.27(d, 2H, J=8.6Hz) |
| III-26 | (chromene cyclopropane with NOH, Ar-3,4-diCl) | 119–120 | 1625 1375 1220 1105 978 | 1460 1310 1125 1022 900 | 1.68(t, 1H, J=6.6Hz)<br>1.88(dd, 1H, J=6.6Hz & 10.6Hz)<br>3.11(dd, 1H, J=6.6Hz & 10.6Hz)<br>6.95–7.05(m, 2H)<br>7.2–7.4(m, 2H)7.4–7.5(m, 1H)<br>7.59(d, 1H, J=2.0Hz)<br>7.79(dd, 1H, J=2.0Hz & 8.2Hz) |

TABLE 2-continued

| Reference Example | Structure | m.p. (°C.) | IR | NMR |
|---|---|---|---|---|
| III-27 | (2-chromanyl cyclopropane with NOH, aryl = 3,4-dimethoxyphenyl) | 154–156 | 3430 2950<br>2840 1630<br>1605 1515<br>1460 1415<br>1380 1320<br>1260 1235<br>1175 1140<br>1025 980<br>910 760 | 1.60(t, 1H, J=6.6Hz)<br>1.91(dd, 1H, J=6.6Hz & 10.6Hz)<br>3.08(dd, 1H, J=6.6Hz & 10.6Hz)<br>3.90(s, 3H), 3.92(s, 3H)<br>6.87–7.33(m, 6H)<br>7.79(dd, 1H, J=1.3Hz & 7.9Hz) |
| III-28 | (6-Cl-chromanyl cyclopropane with NOH, aryl = 4-Cl-phenyl) | 178–181 | 3220 1640<br>1600 1562<br>1480 1410<br>1305 1215<br>1090 1070<br>980 920<br>815 | 1.63(t, 1H, J=6.6Hz)<br>1.90(dd, 1H, J=6.6Hz & 10.6Hz)<br>3.08(dd, 1H, J=6.6Hz & 10.6Hz)<br>6.95–7.05(m, 2H), 7.38(s, 4H)<br>7.71(d, 1H, J=8.6Hz) |
| III-29 | (6-Cl-chromanyl cyclopropane with NOH, aryl = 4-NO₂-phenyl) | 173–174 | 3200 1600<br>1560 1510<br>1410 1340<br>1230 1095<br>1030 990<br>920 840<br>740 | 1.77(t, 1H, J=6.7Hz)<br>1.99(dd, 1H, J=6.7Hz & 11.0Hz)<br>3.19(dd, 1H, J=6.7Hz & 11.0Hz)<br>6.99(dd, 1H, J=1.8Hz & 9.1Hz)<br>7.07(d, 1H, J=1.8Hz)<br>7.57(d, 2H, J=9.1Hz)<br>7.72(d, 1H, J=9.1Hz)<br>8.27(d, 2H, J=9.1Hz) |
| III-30 | (6-F-chromanyl cyclopropane with NOH, aryl = 4-F-phenyl) | 85–90 | 3260 2900<br>1610 1515<br>1505 1430<br>1265 1230<br>1150 1125<br>1090 1000<br>830 810 | 1.62(t, 1H, J=6.6Hz)<br>1.89(dd, 1H, J=6.6Hz & 10.6Hz)<br>3.10(dd, 1H, J=6.6Hz & 10.6Hz)<br>6.66~6.76(m, 2H)<br>7.06~7.48(m, 4H)<br>7.75(dd, 1H, J=6.6Hz & 8.6Hz)<br>8.57(br.s, 1H) |
| III-31 | (6-Cl-chromanyl cyclopropane with NOH, aryl = 4-F-phenyl) | 152–153.5 | 3250 1605<br>1565 1520<br>1485 1415<br>1220 995<br>930 835 | 1.61(dd, 1H, J=6.6Hz & 7.3Hz)<br>1.89(dd, 1H, J=7.3Hz & 10.6Hz)<br>3.08(dd, 1H, J=6.6Hz & 10.6Hz)<br>7.0(m, 2H)<br>7.1(m, 2H)<br>7.4(m, 2H)<br>7.70(d, 1H, J=7.9Hz) |
| III-32 | (6-Cl-chromanyl cyclopropane with NOH, aryl = 4-Br-phenyl) | 208–211 | 3300 1605<br>1570 1485<br>1415 1225<br>1100 1075<br>1010 985<br>925 820 | 1.63(dd, 1H, J=6.6Hz & 7.3Hz)<br>1.90(dd, 1H, J=7.3Hz & 10.6Hz)<br>3.08(dd, 1H, J=6.6Hz & 10.6Hz)<br>7.0(m, 2H)<br>7.32(d, 2H, J=8.6Hz)<br>7.53(d, 2H, J=8.6Hz)<br>7.70(d, 1H, J=7.9Hz) |
| III-33 | (6-Br-chromanyl cyclopropane with NOH, aryl = 4-F-phenyl) | 130–133 | 3265 1600<br>1515 1415<br>1225 985<br>915 830 | 1.61(t, 1H, J=6.6Hz)<br>1.89(dd, 1H, J=6.6Hz & 10.6Hz)<br>3.07(dd, 1H, J=6.6Hz & 10.6Hz)<br>7.1(m, 4H)<br>7.4(m, 2H)<br>7.64(d, 1H, J=8.6Hz) |

TABLE 2-continued

| Reference Example | Structure | m.p. (°C.) | IR | | NMR |
|---|---|---|---|---|---|
| III-34 | (NOH, Br, O, Cl structure) | 202–204 | 3295 1570 1410 1100 985 | 1600 1480 1225 1015 920 | 1.63(t, 1H, J=6.6Hz)<br>1.90(dd, 1H, J=6.6Hz & 10.6Hz)<br>3.08(dd, 1H, J=6.6Hz & 10.6Hz)<br>7.1(m, 2H)<br>7.38(s, 4H)<br>7.64(d, 1H, J=8.6Hz) |
| III-35 | (NOH, Br, O, Br structure) | 208–213 | 3265 1570 1415 1010 920 | 1600 1480 1225 985 820 | 1.62(t, 1H, J=6.6Hz)<br>1.89(dd, 1H, J=7.3Hz & 10.6Hz)<br>3.08(dd, 1H, J=6.6Hz & 10.6Hz)<br>7.1(m, 2H)<br>7.31(d, 2H, J=8.6Hz)<br>7.53(d, 2H, J=8.6Hz)<br>7.64(d, 1H, J=8.6Hz) |

REFERENCE EXAMPLE IV-1

7(1H)-(2-Bromoethyloxyimino)-1a,7a-dihydro-1a-phenylcyclopropa[b]chromen

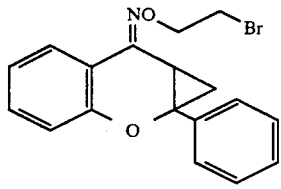

700 mg of the compound of Reference Example III-1 was dissolved in 60 ml of tetrahydrofuran and 223 mg (2 equivalents) of sodium hydride (60% oil-dispersion) was added thereto. After refluxing for 1 hour, 3.14 g (6 equivalents) of ethylene dibromide was added thereto and the mixture was refluxed for 5 hours. The reaction mixture was concentrated and ice/water was added thereto followed by extracting with ether. The extract was washed with water, dried and concentrated. The residue thus obtained was purified by silica gel column chromatography (eluent: hexane:ethyl acetate=95:5) to give 911 mg (yield: 91.3%) of the titled compound. The physicochemical data of the obtained product are shown in the following Table 3.

REFERENCE EXAMPLE IV-2

7(1H)-(2-Chloroethyloxyimino)-1a,7a-dihydro-1a-phenylcyclopropa[b]chromen

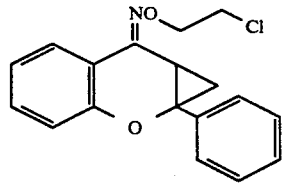

1.5 g of the compound of Reference Example III-1 was dissolved in 40 ml of dioxane and 718 mg (3 equivalents) of sodium hydride (60% oil-dispersion) was added thereto. After adding 5.13 g (6 equivalents) of 1-bromo-2-chloroethane, the mixture was heated under reflux at 100° C. for 5 hours. The reaction mixture was concentrated and ice/water was added thereto followed by extracting with ether. The extract was washed with water, dried and concentrated. The residue thus obtained was purified by silica gel chromatography (eluent: hexane:ethyl acetate=50:1) to give 1.78 g (yield: 95.1%) of the titled compound. The physicochemical data of the obtained product are shown in the following Table 3.

Table 3 further shows the compounds of Reference Examples IV-3 to IV-16 which were produced in the same manner as the one described in this Reference Example.

REFERENCE EXAMPLE IV-17

4-Chloro-1a,7a-dihydro-7(1H)-(2,3-oxypropyloxyimino)-1a-phenylcyclopropa[b]chromen

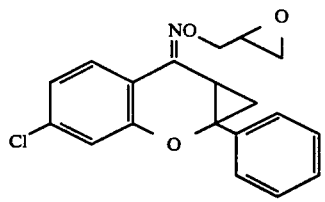

340 mg of the compound of Reference Example III-3 was dissolved in 12 ml of THF and 95.2 mg (2 equivalents) of sodium hydride (60% oil-dispersion) and 440 mg (4 equivalents) of epichlorohydrin were added thereto. After refluxing for 2 hours, the reaction mixture was poured onto ice/water and then extracted with either. The extract was washed with water and dried. The residue thus obtained was purified by silica gel column chromatography (eluent: hexane:ethyl acetate=9:1) to give 307 mg (yield: 79.2%) of the titled compound. The physicochemical data of the obtained product are shown in the following Table 3.

TABLE 3

| Reference Example | Structure | m.p. (°C.) | IR | | NMR |
|---|---|---|---|---|---|
| IV-1 | (phenyl-chromene cyclopropane with N-O-CH2CH2Br oxime) | oil | 3050<br>2960<br>1620<br>1450<br>1255<br>1080<br>1010<br>740 | 3030<br>2930<br>1610<br>1380<br>1235<br>1030<br>760<br>700 | 1.62(t, 1H, J=6.4Hz)<br>1.88(dd, 1H, J=6.4Hz & 9.6Hz)<br>3.06(dd, 1H, J=6.4Hz & 9.6Hz)<br>3.62(t, 2H, J=6.7Hz)<br>4.46(t, 2H, J=6.7Hz)<br>6.93–7.82(m, 9H) |
| IV-2 | (phenyl-chromene cyclopropane with N-O-CH2CH2Cl oxime) | oil | 3015<br>1620<br>1380<br>1255<br>1090<br>980<br>800<br>740 | 2870<br>1455<br>1315<br>1235<br>1035<br>870<br>760<br>695 | 1.63(t, 1H, J=6.6Hz)<br>1.91(dd, 1H, J=6.6Hz & 10.6Hz)<br>3.07(dd, 1H, J=6.6Hz & 10.6Hz)<br>3.81(t, 2H, J=5.9Hz)<br>4.41(t, 2H, J=5.9Hz)<br>6.95–7.50(m, 8H)<br>7.81(dd, 1H, J=1.3Hz & 8.1Hz) |
| IV-3 | (6-chloro-phenyl-chromene cyclopropane with N-O-CH2CH2Cl oxime) | oil | 2930<br>1595<br>1450<br>1375<br>1222<br>1030<br>920<br>746 | 1612<br>1480<br>1415<br>1302<br>1075<br>980<br>812<br>695 | 1.60(t, 1H, J=6.6Hz)<br>1.92(dd, 1H, J=6.6Hz & 10.6Hz)<br>3.04(dd, 1H, J=6.6Hz & 10.6Hz)<br>3.80(t, 2H, J=5.9Hz)<br>4.40(t, 2H, J=5.9Hz)<br>6.9–7.05(m, 2H)7.30–7.5(m, 5H)<br>7.75(d, 1H, J=8.6Hz) |
| IV-4 | (6-bromo-phenyl-chromene cyclopropane with N-O-CH2CH2Cl oxime) | oil | 3020<br>1610<br>1475<br>1410<br>1220<br>1062<br>975<br>805<br>690 | 2920<br>1590<br>1448<br>1300<br>1082<br>1030<br>910<br>745 | 1.60(t, 1H, J=6.6Hz)<br>1.92(dd, 1H, J=6.6Hz & 10.6Hz)<br>3.04(dd, 1H, J=6.6Hz & 10.6Hz)<br>3.79(t, 2H, J=6.0Hz)<br>4.40(t, 2H, J=6.0Hz)<br>7.10(dd, 1H, J=2.0Hz & 8.6Hz)<br>7.17(s, 1H)7.3–7.5(m, 5H)<br>7.68(d, 1H, J=8.6Hz) |
| IV-5 | (6,7-dimethoxy-phenyl-chromene cyclopropane with N-O-CH2CH2Cl oxime) | oil | 2950<br>1605<br>1455<br>1260<br>1200<br>1085<br>860<br>760 | 2840<br>1500<br>1425<br>1220<br>1170<br>1035<br>805<br>695 | 1.57(t, 1H, J=6.6Hz)<br>1.89(dd, 1H, J=6.6Hz & 10.6Hz)<br>3.02(dd, 1H, J=6.6Hz & 10.6Hz)<br>3.81(t, 2H, J=5.9Hz)<br>3.87(s, 3H), 3.90(s, 3H)<br>4.40(t, 2H, J=5.9Hz)<br>6.50(s, 1H)7.21–7.49(m, 6H) |
| IV-6 | (4-chlorophenyl-chromene cyclopropane with N-O-CH2CH2Cl oxime) | oil | 2900<br>1490<br>1380<br>1310<br>1230<br>1030<br>815<br>745 | 1610<br>1450<br>1340<br>1255<br>1085<br>980<br>760 | 1.63(t, 1H, J=6.6Hz)<br>1.85(dd, 1H, J=6.6Hz & 10.5Hz)<br>3.03(dd, 1H, J=6.6Hz & 10.5Hz)<br>3.78–3.84(m, 2H),<br>4.39–4.43(m, 2H)<br>6.96–7.40(m, 7H)<br>7.81(dd, 1H, J=2.2Hz & 7.9Hz) |
| IV-7 | (6-chloro-4-chlorophenyl-chromene cyclopropane with N-O-CH2CH2Cl oxime) | oil | 1612<br>1555<br>1415<br>1330<br>1265<br>1135<br>1090<br>1022<br>920<br>850<br>750 | 1598<br>1480<br>1370<br>1305<br>1220<br>1108<br>1070<br>1005<br>880<br>812<br>725 | 1.61(t, 1H, J=7.3Hz)<br>1.88(dd, 1H, J=7.3Hz & 10.6Hz)<br>3.02(dd, 1H, J=7.3Hz & 10.6Hz)<br>3.80(t, 2H, J=5.9Hz)<br>4.41(t, 2H, J=5.9Hz)<br>6.9–7.0(m, 2H)7.37(s, 4H)<br>7.75(d, 1H, J=8.6Hz) |

TABLE 3-continued

| Reference Example | Structure | m.p. (°C.) | IR | | NMR |
|---|---|---|---|---|---|
| IV-8 | [chromene cyclopropane with N-O-CH2CH2CH2-Br oxime, phenyl substituent] | oil | 3050 1615 1455 1310 1230 1105 980 760 690 | 2900 1600 1380 1255 1125 1030 870 740 | 1.61(t, 1H, J=6.6Hz) 1.89(dd, 1H, J=6.6Hz & 10.6Hz) 2.26–2.35(m, 2H), 2.99(dd, 1H, J=6.6Hz & 10.6Hz) 3.53(t, 2H, J=6.6Hz) 4.34(t, 2H, J=5.3Hz) 6.94–7.49(m, 8H) 7.82(dd, 1H, J=1.3Hz & 7.9Hz) |
| IV-9 | [chromene cyclopropane with N-O-CH2CH2CH2-Cl oxime, phenyl substituent] | oil | 3060 1620 1500 1460 1340 1260 1050 760 695 | 2970 1600 1480 1380 1310 1235 980 740 | 1.61(t, 1H, J=6.3Hz) 1.88(dd, 1H, J=6.3Hz & 11.1Hz) 2.16–2.26(m, 2H) 2.98(dd, 1H, J=6.3Hz & 11.1Hz) 3.67(t, 2H, J=14.3Hz) 4.30–4.36(m, 2H) 6.93–7.83(m, 9H) |
| IV-10 | [6-chloro chromene cyclopropane with N-O-CH2CH2CH2-Cl oxime, phenyl] | oil | 2920 1610 1445 1375 1220 1040 805 690 | 2820 1480 1410 1300 1070 980 745 | 1.59(t, 1H, J=6.6Hz) 1.91(dd, 1H, J=6.6Hz & 10.5Hz) 2.21(quintett, 2H, J=6.2Hz) 2.97(dd, 1H, J=6.6Hz & 10.5Hz) 3.67(t, 2H, J=6.2Hz) 4.33(t, 2H, J=6.2Hz) 6.93–7.46(m, 7H) 7.76(d, 1H, J=8.6Hz) |
| IV-11 | [6-bromo chromene cyclopropane with N-O-CH2CH2CH2-Cl oxime, phenyl] | oil | 2920 1590 1448 1370 1300 1220 1102 980 875 742 | 1605 1475 1410 1330 1260 1135 1035 902 805 685 | 1.50–1.65(t, 1H, J=6.6Hz) 1.91(dd, 1H, J=6.6Hz & 10.6Hz) 2.15–2.3(m, 2H) 2.97(dd, 1H, J=6.6Hz & 10.6Hz) 3.67(t, 2H, J=6.6Hz) 4.33(t, 2H, J=6.6Hz) 7.10(dd, 1H, J=2.0Hz & 8.6Hz) 7.17(d, 1H, J=2.0Hz) 7.3–7.5(m, 5H) 7.69(d, 1H, J=8.6Hz) |
| IV-12 | [6,7-dimethoxy chromene cyclopropane with N-O-CH2CH2CH2-Cl oxime, phenyl] | oil | 2920 1600 1465 1420 1300 1210 1160 1035 805 690 | 1620 1500 1450 1370 1255 1195 1080 865 755 | 1.56(t, 1H, J=6.6Hz) 1.87(dd, 1H, J=6.6Hz & 10.5Hz) 2.22(quintett, 2H, J=6.6Hz) 2.94(dd, 1H, J=6.6Hz & 10.5Hz) 3.69(t, 2H, J=6.6Hz) 3.87(s, 3H), 3.90(s, 3H) 4.32(t, 2H, J=6.6Hz) 6.49(s, 1H) 7.23–7.48(m, 6H) |
| IV-13 | [6-chloro chromene cyclopropane with N-O-CH2CH2CH2-Cl oxime, 4-chlorophenyl] | oil | 2920 1592 1412 1305 1090 1020 805 | 1605 1480 1375 1220 1040 980 | 1.60(t, 1H, J=6.6Hz) 1.87(dd, 1H, J=6.6Hz & 10.6Hz) 2.15–2.25(m, 2H) 2.94(dd, 1H, J=6.6Hz & 10.6Hz) 3.67(t, 2H, J=6.6Hz) 4.33(t, 2H, J=6.6Hz)6.9–7.0(m, 2H) 7.3–7.45(m, 4H)7.75(d, 1H, J=7.9Hz) |
| IV-14 | [chromene cyclopropane with N-O-CH2CH2CH2CH2-Br oxime, phenyl] | oil | 3050 2940 1615 1500 1450 1340 1255 1030 760 690 | 3030 2870 1600 1480 1380 1315 1235 980 740 | 1.51(t, 1H, J=6.4Hz) 1.84–2.06(m, 5H) 2.99(dd, 1H, J=6.4Hz & 10.9Hz) 3.47(t, 2H, J=7.1Hz) 4.22(t, 2H, J=5.8Hz) 6.95–7.83(m, 9H) |

TABLE 3-continued

| Reference Example | Structure | m.p. (°C.) | IR | | NMR |
|---|---|---|---|---|---|
| IV-15 | (chromene with cyclopropane, N-O-(CH2)5-Br, phenyl substituent) | oil | 3050 2930 1610 1480 1380 1230 740 | 3020 2860 1595 1445 1250 760 690 | 1.60–1.98(m, 8H) 3.01(dd, 1H, J=5.8Hz & 10.9Hz) 3.42(t, 2H, J=6.4Hz) 4.20(t, 2H, J=6.4Hz) 6.94–7.85(m, 9H) |
| IV-16 | (4-Cl-chromene with cyclopropane, N-O-(CH2)4-Br, 4-Cl-phenyl substituent) | oil | 2960 2875 1600 1480 1225 1075 1010 815 760 | 2940 1615 1495 1415 1100 1025 990 785 | 1.59(t, 1H, J=6.6Hz) 1.8–2.1(m, 5H) 2.95(dd, 1H, J=6.6Hz & 10.6Hz) 3.47(t, 2H, J=6.6Hz) 4.22(m, 2H) 6.9–7.0(m, 2H) 7.37(s, 4H) 7.76(d, 1H, J=8.6Hz) |
| IV-17 | (4-Cl-chromene with cyclopropane, N-O-CH2-CH=CH2 (allyl), phenyl substituent) | oil | 3050 2820 1590 1220 980 685 | 2980 1605 1410 1040 740 | 1.59(t, 1H, J=6.4Hz) 1.92(dd, 1H, J=6.4Hz & 10.2Hz) 2.67(m, 1H) 2.87(m, 1H) 3.03(m, 1H) 3.23(m, 1H) 4.12(dd, 1H, J=7.7Hz & 12.8Hz) 4.40(dd, 1H, J=3.2Hz & 12.8Hz) 6.95(dd, 1H, J=2.7Hz & 7.7Hz) 6.99(d, 1H, J=2.7Hz) 7.25–7.52(m, 5H) 7.77(d, 1H, J=7.7Hz) |

EXAMPLE 1

1a,7a-Dihydro-7(1H)-(2-methylaminoethyloxyimino)-1a-phenylcyclopropa[b]chromen [Compound of the general formula (I) wherein $A^1$=H; $A^2$=H; $B^1$=H; $B^2$=H; $NR^1R^2$=NHCH$_3$ and n=2]

260 mg of the compound of Reference Example IV-2 was dissolved in 10 ml of dioxane and 10 ml of monomethylaminesaturated dioxane was added thereto. The mixture was heated to 100° C. in a sealed tube for 17 hours. After distilling off the dioxane, water and an aqueous solution of sodium hydroxide were added thereto followed by extracting with methylene chloride. The extract was washed with water and dried over anhydrous magnesium sulfate. After filtering and concentrating the solution, the obtained residue was eluted with silica gel column chromatography by using methylene chloride/methanol (9:1). Thus 213 mg (yield: 83.4%) of the titled compound was obtained. The product thus obtained was further converted into the tartrate in a conventional manner.

EXAMPLE 2

4-Chloro-1a,7a-dihydro-7(1H)-(2-methylaminoethyloxyimino)-1a-phenylcyclopropa[b]chromen [Compound of the general formula (I) wherein $A^1$=4-Cl; $A^2$=H; $B^1$=H; $B^2$=H; $NR^1R^2$=NHCH$_3$ and n=2]

Starting from the compound of Reference Example IV-3, the titled compound was produced in the same manner as the one described in Example 1.

EXAMPLE 3

4-Bromo-1a,7a-dihydro-7(1H)-(2-methylaminoethyloxyimino)-1a-phenylcyclopropa[b]chromen [Compound of the general formula (I) wherein $A^1$=4-Br; $A^2$=H; $B^1$=H; $B^2$=H; $NR^1R^2$=NHCH$_3$ and n=2]

Starting from the compound of Reference Example IV-4, the titled compound was produced in the same manner as the one described in Example 1.

EXAMPLE 4

1a,7a-Dihydro-4,5-dimethoxy-7(1H)-(2-methylaminoethyloxyimino)-1a-phenylcyclopropa[b]chromen [Compound of the general formula (I) wherein $A^1$=4-OCH$_3$; $A^2$=5-OCH$_3$; $B^1$=H; $B^2$=H; $NR^1R^2$=NHCH$_3$ and n=2]

Starting from the compound of Reference Example IV-5, the titled compound was produced in the same manner as the one described in Example 1.

EXAMPLE 5

1a-(4-Chlorophenyl)-1a,7a-dihydro-7(1H)-(2-methylaminoethyloxyimino)cyclopropa[b]chromen [Compound of the general formula (I) wherein $A^1$=H; $A^2$=H; $B^1$=H; $B^2$=4-Cl; $NR^1R^2$=NHCH$_3$ and n=2]

Starting from the compound of Reference Example IV-6, the titled compound was produced in the same manner as the one described in Example 1.

EXAMPLE 6

4-Chloro-1a-(4-chlorophenyl)-1a,7a-dihydro-7(1H)-(2-methylaminoethyloxyimino)cyclopropa[b]chromen [Compound of the general formula (I) wherein $A^1$=4-Cl; $A^2$=H; $B^1$=H; $B^2$=4-Cl; $NR^1R^2$=NHCH$_3$ and n=2]

Starting from the compound of Reference Example IV-7, the titled compound was produced in the same manner as the one described in Example 1.

EXAMPLE 7

1a,7a-Dihydro-7(1H)-(2-dimethylaminoethyloxyimino)-1a-phenylcyclopropa[b]chromen [Compound of the general formula (I) wherein $A^1$=H; $A^2$=H; $B^1$=H; $B^2$=H; $NR^1R^2$=N(CH$_3$)$_2$ and n=2]

600 mg (2.4 mmol) of the compound of Reference Example III-1 was dissolved in 20 ml of tetrahydrofuran and 382 mg (9.6 mmol) of sodium hydride (60% oil-dispersion) and 1.54 g (7.2 mmol) of dimethylaminoethyl chloride were added thereto. The obtained mixture was heated under reflux over a day and night. The reaction mixture was concentrated and ice/water was added thereto followed by extracting with ether. The ether phase was washed with water and dried over anhydrous magnesium sulfate. After filtering and concentrating, the residue thus obtained was eluted by neutral silica gel column chromatography by eluting with methylene chloride/methanol (95:5) to give 220 mg (yield: 30.2%) of the titled compound. The product thus obtained was further converted into the maleate by a conventional manner and crystallized from ethanol/ether.

EXAMPLE 8

1a,7a-Dihydro-7(1H)-(2-dimethylaminoethyloxyimino)-4-fluoro-1a-phenylcyclopropa[b]chromen [Compound of the general formula (I) wherein $A^1$=4-F; $A^2$=H; $B^1$=H; $B^2$=H; $NR^1R^2$=N(CH$_3$)$_2$ and n=2]

Starting from the compound of Reference Example III-2, the titled compound was produced in the same manner as the one described in Example 7.

EXAMPLE 9

4-Chloro-1a,7a-dihydro-7(1H)-(2-dimethylaminoethyloxyimino)-1a-phenylcyclopropa[b]chromen [Compound of the general formula (I) wherein $A^1$=4-Cl; $A^2$=H; $B^1$=H; $B^2$=H; $NR^1R^2$=N(CH$_3$)$_2$ and n=2]

Starting from the compound of Reference Example III-3, the titled compound was produced in the same manner as the one described in Example 7.

EXAMPLE 10

4-Bromo-1a,7a-dihydro-7(1H)-(2-dimethylaminoethyloxyimino)-1a-phenylcyclopropa[b]chromen [Compound of the general formula (I) wherein $A^1$=4-Br; $A^2$=H; $B^1$=H; $B^2$=H; $NR^1R^2$=N(CH$_3$)$_2$ and n=2]

Starting from the compound of Reference Example III-4, the titled compound was produced in the same manner as the one described in Example 7.

EXAMPLE 11

1a,7a-Dihydro-7(1H)-(2-dimethylaminoethyloxyimino)-4-methoxy-1a-phenylcyclopropa[b]chromen [Compound of the general formula (I) wherein $A^1$=4-OCH$_3$; $A^2$=H; $B^1$=H; $B^2$=H; $NR^1R^2$=N(CH$_3$)$_2$ and n=2]

Starting from the compound of Reference Example III-5, the titled compound was produced in the same manner as the one described in Example 7.

EXAMPLE 12

5-Chloro-1a,7a-dihydro-7(1H)-(2-dimethylaminoethyloxyimino)-1a-phenylcyclopropa[b]chromen [Compound of the general formula (I) wherein $A^1$=5-Cl; $A^2$=H; $B^1$=H; $B^2$=H; $NR^1R^2$=N(CH$_3$)$_2$ and n=2]

Starting from the compound of Reference Example III-7, the titled compound was produced in the same manner as the one described in Example 7.

EXAMPLE 13

1a,7a-Dihydro-7(1H)-(2-dimethylaminoethyloxyimino)-5-methoxy-1a-phenylcyclopropa[b]chromen [Compound of the general formula (I) wherein $A^1$=5-OCH$_3$; $A^2$=H; $B^1$=H; $B^2$=H; $NR^1R^2$=N(CH$_3$)$_2$ and n=2]

Starting from the compound of Reference Example III-8, the titled compound was produced in the same manner as the one described in Example 7.

EXAMPLE 14

1a,7a-Dihydro-7(1H)-(2-dimethylaminoethyloxyimino)-6-methoxy-1a-phenylcyclopropa[b]chromen [Compound of the general formula (I) wherein $A^1$=6-OCH$_3$; $A^2$=H; $B^1$=H; $B^2$=H; $NR^1R^2$=N(CH$_3$)$_2$ and n=2]

Starting from the compound of Reference Example III-9, the titled compound was produced in the same manner as the one described in Example 7.

EXAMPLE 15

4,5-Dichloro-1a,7a-dihydro-7(1H)-(2-dimethylaminoethyloxyimino)-1a-phenylcyclopropa[b]chromen [Compound of the general formula (I) wherein $A^1$=4-Cl; $A^2$=5-Cl; $B^1$=H; $B^2$=H; $NR^1R^2$=N(CH$_3$)$_2$ and n=2]

Starting from the compound of Reference Example III-11, the titled compound was produced in the same manner as the one described in Example 7.

EXAMPLE 16

1a,7a-Dihydro-4,5-dimethoxy-7(1H)-(2-dimethylaminoethyloxyimino)-1a-phenylcyclopropa[b]chromen [Compound of the general formula (I) wherein $A^1$=4-OCH$_3$; $A^2$=5-OCH$_3$; $B^1$=H; $B^2$=H; $NR^1R^2$=N(CH$_3$)$_2$ and n=2]

Starting from the compound of Reference Example III-12, the titled compound was produced in the same manner as the one described in Example 7.

EXAMPLE 17

1a-(4-Chlorophenyl)-1a,7a-dihydro-7(1H)-(2-dimethylaminoethyloxyimino)cyclopropa[b]chromen [Compound of the general formula (I) wherein $A^1=H$; $A^2=H$; $B^1=4$-Cl; $B^2=H$; $NR^1R^2=N(CH_3)_2$ and $n=2$]

Starting from the compound of Reference Example III-19, the titled compound was produced in the same manner as the one described in Example 7.

EXAMPLE 18

1a,7a-Dihydro-7-(1H)-(2-dimethylaminoethyloxyimino)-1a-(4-methoxyphenyl)cyclopropa[b]chromen [Compound of the general formula (I) wherein $A^1=H$; $A^2=H$; $B^1=4$-OCH$_3$; $B^2=H$; $NR^1R^2=N(CH_3)_2$ and $n=2$]

Starting from the compound of Reference Example III-20, the titled compound was produced in the same manner as the one described in Example 7.

EXAMPLE 19

1a,7a-Dihydro-7(1H)-(2-dimethylaminoethyloxyimino)-1a-(4-methylphenyl)cyclopropa[b]chromen [Compound of the general formula (I) wherein $A^1=H$; $A^2=H$; $B^1=4$-CH$_3$; $B^2=H$; $NR^1R^2=N(CH_3)_2$ and $n=2$]

Starting from the compound of Reference Example III-21, the titled compound was produced in the same manner as the one described in Example 7.

EXAMPLE 20

1a,7a-Dihydro-7(1H)-(2-dimethylaminoethyloxyimino)-1a-(4-trifluoromethylphenyl)cyclopropa[b]chromen [Compound of the general formula (I) wherein $A^1=H$; $A^2=H$; $B^1=4$-CF$_3$; $B^2=H$; $NR^1R^2=N(CH_3)_2$ and $n=2$]

Starting from the compound of Reference Example III-22, the titled compound was produced in the same manner as the one described in Example 7.

EXAMPLE 21

1a,7a-Dihydro-7(1H)-(2-dimethylaminoethyloxyimino)-1a-(4-methoxycarbonylphenyl)cyclopropa[b]chromen [Compound of the general formula (I) wherein $A^1=H$; $A^2=H$; $B^1=4$-CO$_2$CH$_3$; $B^2=H$; $NR^1R^2=N(CH_3)_2$ and $n=2$]

Starting from the compound of Reference Example III-23, the titled compound was produced in the same manner as the one described in Example 7.

EXAMPLE 22

1a-(4-Cyanophenyl)-1a,7a-dihydro-7(1H)-(2-dimethylaminoethyloxyimino)cyclopropa[b]chromen [Compound of the general formula (I) wherein $A^1=H$; $A^2=H$; $B^1=4$-CN; $B^1=H$; $NR^1R^2=N(CH_3)_2$ and $n=2$]

Starting from the compound of Reference Example III-24, the titled compound was produced in the same manner as the one described in Example 7.

EXAMPLE 23

1a,7a-Dihydro-7(1H)-(2-dimethylaminoethyloxyimino)-1a-(4-nitrophenyl)cyclopropa[b]chromen [Compound of the general formula (I) wherein $A^1=H$; $A^2=H$; $B^1=4$-NO$_2$; $B^2=H$; $NR^1R^2=N(CH_3)_2$ and $n=2$]

Starting from the compound of Reference Example III-25, the titled compound was produced in the same manner as the one described in Example 7.

EXAMPLE 24

1a-(3,4-Dichlorophenyl)-1a,7a-dihydro-7(1H)-(2-dimethylaminoethyloxyimino)cyclopropa[b]chromen [Compound of the general formula (I) wherein $A^1=H$; $A^2=H$; $B^1=3$-Cl; $B^2=4$-Cl; $NR^1R^2=N(CH_3)_2$ and $n=2$]

Starting from the compound of Reference Example III-26, the titled compound was produced in the same manner as the one described in Example 7.

EXAMPLE 25

4-Chloro-1a-(4-chlorophenyl)-1a,7a-dihydro-7(1H)-(2-dimethylaminoethyloxyimino)cyclopropa[b]chromen [Compound of the general formula (I) wherein $A^1=4$-Cl; $A^2=H$; $B^1=4$-Cl; $B^2=H$; $NR^1R^2=N(CH_3)_2$ and $n=2$]

Starting from the compound of Reference Example III-28, the titled compound was produced in the same manner as the one described in Example 7.

EXAMPLE 26

7(1H)-(2-Diethylaminoethyloxyimino)-1a,7a-dihydro-1a-phenylcyclopropa[b]chromen [Compound of the general formula (I) wherein $A^1=H$; $A^2=H$; $B^1=H$; $B^2=H$; $NR^1R^2=N(C_2H_5)_2$ and $n=2$]

Starting from the compound of Reference Example III-1, the titled compound was produced in the same manner as the one described in Example 7.

EXAMPLE 27

7(1H)-(2-Diethylaminoethyloxyimino)-1a,7a-dihydro-4,5-dimethoxy-1a-phenylcyclopropa[b]chromen [Compound of the general formula (I) wherein $A^1=4$-OCH$_3$; $A^2=5$-OCH$_3$; $B^1=H$; $B^2=H$; $NR^1R^2=N(C_2H_5)_2$ and $n=2$]

Starting from the compound of Reference Example III-12, the titled compound was produced in the same manner as the one described in Example 7.

EXAMPLE 28

1a,7a-Dihydro-7(1H)-(2-morpholinoethyloxyimino)-1a-phenylcyclopropa[b]chromen [Compound of the general formula (I) wherein $A^1=H$; $A^2=H$; $B^1=H$; $B^2=H$; $NR^1R^2=$morpholino and $n=2$]

Starting from the compound of Reference Example IV-1, the titled compound was produced in the same manner as the one described in Example 1.

EXAMPLE 29

1a,7a-Dihydro-7(1H)-[2-(4-methyl-1-piperazinyl)e-thyloxyimino]-1a-phenylcyclopropa[b]chromen [Compound of the general formula (I) wherein $A^1=H$; $A^2=H$; $B^1=H$; $B^2=H$;

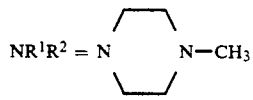

and n=2]

Starting from the compound of Reference Example IV-2, the titled compound was produced in the same manner as the one described in Example 1.

EXAMPLE 30

1a,7a-Dihydro-1a-phenyl-7(1H)-[2-(1-piperidinyl)e-thyloxyimino]-cyclopropa[b]chromen [Compound of the general formula (I) wherein $A^1=H$; $A^2=H$; $B^1=H$; $B^2=H$; $NR^1R^2$=piperidinyl and n=2]

Starting from the compound of Reference Example IV-2, the titled compound was produced in the same manner as the one described in Example 1.

EXAMPLE 31

1a,7a-Dihydro-7(1H)-[2-(1-homopiperidinyl)ethylox-yimino]-1a-phenylcyclopropa[b]chromen [Compound of the general formula (I) wherein $A^1=H$; $A^2=H$; $B^1=H$; $B^2=H$; $NR^1R^2$=homopiperidinyl and n=2]

Starting from the compound of Reference Example IV-2, the titled compound was produced in the same manner as the one described in Example 1.

EXAMPLE 32

7(1H)-(3-aminopropyloxyimino)-1a,7a-dihydro-1a-phenylcyclopropa[b]chromen [Compound of the general formula (I) wherein $A^1=H$; $A^2=H$; $B^1=H$; $B^2=H$; $NR^1R^2=NH_2$ and n=3]

Starting from the compound of Reference Example III-1, the titled compound was produced in the same manner as the one described in Example 7.

EXAMPLE 33

1a,7a-Dihydro-7(1H)-(3-methylaminopropyloxyimino)-1a-phenylcyclopropa[b]chromen [Compound of the general formula (I) wherein $A^1=H$; $A^2=H$; $B^1=H$; $B^2=H$; $NR^1R^2=NHCH_3$ and n=3]

Starting from the compound of Reference Example IV-9, the titled compound was produced in the same manner as the one described in Example 1. Then the obtained product was converted into the fumarate (m.p.: 131°–133° C.), the maleate (m.p.: 160°–162° C.) and the oxalate (m.p.: 168°–171° C.), in addition to the tartrate.

EXAMPLE 34

1a,7a-Dihydro-4-fluoro-7(1H)-(3-methylamino-propyloxyimino)-1a-phenylcyclopropa[b]chromen [Compound of the general formula (I) wherein $A^1=4$-F; $A^2=H$; $B^1=H$; $B^2=H$; $NR^1R^2=NHCH_3$ and n=3]

Starting from the compound of Reference Example III-2, the titled compound was produced in the same manner as the one described in Example 7.

EXAMPLE 35

4-Chloro-1a,7a-dihydro-7(1H)-(3-methylamino-propyloxyimino)-1a-phenylcyclopropa[b]chromen [Compound of the general formula (I) wherein $A^1=4$-Cl; $A^2=H$; $B^1=H$; $B^2=H$; $NR^1R^2=NHCH_3$ and n=3]

Starting from the compound of Reference Example III-3, the titled compound was produced in the same manner as the one described in Example 7.

EXAMPLE 36

4-Bromo-1a,7a-dihydro-7(1H)-(3-methylamino-propyloxyimino)-1a-phenylcyclopropa[b]chromen [Compound of the general formula (I) wherein $A^1=4$-Br; $A^2=H$; $B^1=H$; $B^2=H$; $NR^1R^2=NHCH_3$ and n=3]

Starting from the compound of Reference Example III-4, the titled compound was produced in the same manner as the one described in Example 7.

EXAMPLE 37

1a,7a-Dihydro-4-methoxy-7(1H)-(3-methylamino-propyloxyimino)-1a-phenylcyclopropa[b]chromen [Compound of the general formula (I) wherein $A^1=4$-OCH$_3$; $A^2=H$; $B^1=H$; $B^2=H$; $NR^1R^2=NHCH_3$ and n=3]

Starting from the compound of Reference Example III-5, the titled compound was produced in the same manner as the one described in Example 7.

EXAMPLE 38

5-Chloro-1a,7a-dihydro-7(1H)-(3-methylamino-propyloxyimino)-1a-phenylcyclopropa[b]chromen [Compound of the general formula (I) wherein $A^1=5$-Cl; $A^2=H$; $B^1=H$; $B^2=H$; $NR^1R^2=NHCH_3$ and n=3]

Starting from the compound of Reference Example III-7, the titled compound was produced in the same manner as the one described in Example 7.

EXAMPLE 39

4,5-Dichloro-1a,7a-dihydro-7(1H)-(3-methylamino-propyloxyimino)-1a-phenylcyclopropa[b]chromen [Compound of the general formula (I) wherein $A^1=4$-Cl; $A^2=5$-Cl; $B^1=H$; $B^2=H$; $NR^1R^2=NHCH_3$ and n=3]

Starting from the compound of Reference Example III-11, the titled compound was produced in the same manner as the one described in Example 7.

EXAMPLE 40

1a,7a-Dihydro-4,5-dimethoxy-7(1H)-(3-methylaminopropyloxyimino)-1a-phenylcyclopropa[b]chromen [Compound of the general formula (I) wherein $A^1=4\text{-OCH}_3$; $A^2=5\text{-OCH}_3$; $B^1=H$; $B^2=H$; $NR^1R^2=NHCH_3$ and $n=3$]

Starting from the compound of Reference Example III-12, the titled compound was produced in the same manner as the one described in Example 7.

EXAMPLE 41

1a,7a-Dihydro-7(1H)-(3-methylaminopropyloxyimino)-1a-(4-methoxyphenyl)cyclopropa[b]chromen [Compound of the general formula (I) wherein $A^1=H$; $A^2=H$; $B^1=4\text{-OCH}_3$; $B^2=H$; $NR^1R^2=NHCH_3$ and $n=3$]

Starting from the compound of Reference Example III-20, the titled compound was produced in the same manner as the one described in Example 7.

EXAMPLE 42

1a-(3,4-Dichlorophenyl)-1a,7a-dihydro-7(1H)-(3-methylaminopropyloxyimino)cyclopropa[b]chromen [Compound of the general formula (I) wherein $A^1=H$; $A^2=H$; $B^1=3\text{-Cl}$; $B^2=4\text{-Cl}$; $NR^1r^2=NHCH_3$ and $n=3$]

Starting from the compound of Reference Example III-26, the titled compound was produced in the same manner as the one described in Example 7.

EXAMPLE 43

1a,7a-Dihydro-4-fluoro-1a-(4-fluorophenyl)-7(1H)-(3-methylaminopropyloxyimino)cyclopropa[b]chromen [Compound of the general formula (I) wherein $A^1=4\text{-F}$; $A^2=H$; $B^1=4\text{-F}$; $B^2=H$; $NR^1R^2=NHCH_3$ and $n=3$]

Starting from the compound of Reference Example III-30, the titled compound was produced in the same manner as the one described in Example 7.

EXAMPLE 44

4-Chloro-1a,7a-dihydro-1a-(4-fluorophenyl)-7(1H)-(3-methylaminopropyloxyimino)cyclopropa[b]chromen [Compound of the general formula (I) wherein $A^1=4\text{-Cl}$; $A^2=H$; $B^1=4\text{-F}$; $B^2=H$; $NR^1R^2=NHCH_3$ and $n=3$]

Starting from the compound of Reference Example III-31, the titled compound was produced in the same manner as the one described in Example 7.

EXAMPLE 45

4-Chloro-1a-(4-chlorophenyl)-1a,7a-dihydro-7(1H)-(3-methylaminopropyloxyimino)cyclopropa[b]chromen [Compound of the general formula (I) wherein $A^1=4\text{-Cl}$; $A^2=H$; $B^1=4\text{-Cl}$; $B^2=H$; $NR^1R^2=NHCH_3$ and $n=3$]

Starting from the compound of Reference Example III-28, the titled compound was produced in the same manner as the one described in Example 7. Then the product was converted into the maleate (m.p.: 105°–107° C.) and the fumarate (m.p.: 155°–157° C.), in addition to the tartrate.

EXAMPLE 46

1a-(4-Bromophenyl)-4-chloro-1a,7a-dihydro-7(1H)-(3-methylaminopropyloxyimino)cyclopropa[b]chromen [Compound of the general formula (I) wherein $A^1=4\text{-Cl}$; $A^2=H$; $B^1=4\text{-Br}$; $B^2=H$; $NR^1R^2=NHCH_3$ and $n=3$]

Starting from the compound of Reference Example III-32, the titled compound was produced in the same manner as the one described in Example 7.

EXAMPLE 47

4-Bromo-1a,7a-dihydro-1a-(4-fluorophenyl)-7(1H)-(3-methylaminopropyloxyimino)cyclopropa[b]chromen [Compound of the general formula (I) wherein $A^1=4\text{-Br}$; $A^2=H$; $B^1=4\text{-F}$; $B^2=H$; $NR^1R^2=NHCH_3$ and $n=3$]

Starting from the compound of Reference Example III-33, the titled compound was produced in the same manner as the one described in Example 7.

EXAMPLE 48

4-Bromo-1a-(4-chlorophenyl)-1a,7a-dihydro-7(1H)-(3-methylaminopropyloxyimino)cyclopropa[b]chromen [Compound of the general formula (I) wherein $A^1=4\text{-Br}$; $A^2=H$; $B^1=4\text{-Cl}$; $B^2=H$; $NR^1R^2=NHCH_3$ and $n=3$]

Starting from the compound of Reference Example III-34, the titled compound was produced in the same manner as the one described in Example 7.

EXAMPLE 49

4-Bromo-1a-(4-bromophenyl)-1a,7a-dihydro-7(1H)-(3-methylaminopropyloxyimino)cyclopropa[b]chromen [Compound of the general formula (I) wherein $A^1=4\text{-Br}$; $A^2=H$, $B^1=4\text{-Br}$; $B^2=H$; $NR^1R^2=NHCH_3$ and $n=3$]

Starting from the compound of Reference Example III-35, the titled compound was produced in the same manner as the one described in Example 7.

EXAMPLE 50

1a,7a-Dihydro-7(1H)-(3-ethylaminopropyloxyimino)-1a-phenylcyclopropa[b]chromen [Compound of the general formula (I) wherein $A^1=H$; $A^2=H$; $B^1=H$; $B^2=H$; $NR^1R^2=NHC_2H_5$ and $n=3$]

Starting from the compound of Reference Example III-1, the titled compound was produced in the same manner as the one described in Example 7.

EXAMPLE 51

1a,7a-Dihydro-4-fluoro-7(1H)-(3-ethylaminopropyloxyimino)-1a-phenylcyclopropa[b]chromen [Compound of the general formula (I) wherein $A^1=4\text{-F}$; $A^2=H$; $B^1=H$; $NR^1R^2=NHC_2H_5$ and $n=3$]

Starting from the compound of Reference Example III-2, the titled compound was produced in the same manner as the one described in Example 7.

EXAMPLE 52

4-Chloro-1a,7a-dihydro-7(1H)-(3-ethylaminopropyloxyimino)-1a-phenylcyclopropa[b]chromen [Compound of the general formula (I) wherein $A^1=4$-Cl; $A^2=H$; $B^1=H$; $B^2=H$; $NR^1R^2=NHC_2H_5$ and $n=3$]

Starting from the compound of Reference Example III-3, the titled compound was produced in the same manner as the one described in Example 74

EXAMPLE 53

4-Bromo-1a,7a-dihydro-7(1H)-(3-ethylaminopropyloxyimino)-1a-phenylcyclopropa[b]chromen [Compound of the general formula (I) wherein $A^1=4$-Br; $A^2=H$; $B^1=H$; $B^2=H$; $NR^1R^2=NHC_2H_5$ and $n=3$]

Starting from the compound of Reference Example III-4, the titled compound was produced in the same manner as the one described in Example 7.

EXAMPLE 54

5-Chloro-1a,7a-dihydro-7(1H)-(3-ethylaminopropyloxyimino)-1a-phenylcyclopropa[b]chromen [Compound of the general formula (I) wherein $A^1=5$-Cl; $A^2=H$; $B^1=H$; $B^2=H$; $NR^1R^2=NHC_2H_5$ and $n=3$]

Starting from the compound of Reference Example III-7, the titled compound was produced in the same manner as the one described in Example 7.

EXAMPLE 55

4,5-Dichloro-1a,7a-dihydro-7(1H)-(3-ethylaminopropyloxyimino)-1a-phenylcyclopropa[b]chromen [Compound of the general formula (I) wherein $A^1=4$-Cl; $A^2=5$-Cl; $B^1=H$; $B^2=H$; $NR^1R^2=NHC_2H_5$ and $n=3$]

Starting from the compound of Reference Example III-11, the titled compound was produced in the same manner as the one described in Example 7.

EXAMPLE 56

1a-(3,4-Dichlorophenyl)-1a,7a-dihydro-7(1H)-(3-ethylaminopropyloxyimino)cyclopropa[b]chromen [Compound of the general formula (I) wherein $A^1=H$; $A^2=H$; $B^1=3$-Cl; $B^2=4$-Cl; $NR^1R^2=NHC_2H_5$ and $n=3$]

Starting from the compound of Reference Example III-26, the titled compound was produced in the same manner as the one described in Example 7.

EXAMPLE 57

4-Chloro-1a-(4-chlorophenyl)-1a,7a-dihydro-7(1H)-(3-ethylaminopropyloxyimino)cyclopropa[b]chromen [Compound of the general formula (I) wherein $A^1=4$-Cl; $A^2=H$; $B^1=4$-Cl; $B^2=H$; $NR^1R^2=NHC_2H_5$ and $n=3$]

Starting from the compound of Reference Example III-28, the titled compound was produced in the same manner as the one described in Example 7.

EXAMPLE 58

1a,7a-Dihydro-7(1H)-(3-propylaminopropyloxyimino)-1a-phenylcyclopropa[b]chromen [Compound of the general formula (I) wherein $A^1=H$; $A^2=H$; $B^1=H$; $B^2=H$; $NR^1R^2=NHCH_2CH_2CH_3$ and $n=3$]

Starting from the compound of Reference Example III-1, the titled compound was produced in the same manner as the one described in Example 7.

EXAMPLE 59

1a,7a-Dihydro-7(1H)-[3-(N-isopropylamino)propyloxyimino]-1a-phenylcyclopropa[b]chromen [Compound of the general formula (I) wherein $A^1=H$; $A^2=H$; $B^1=H$; $B^2=H$; $NR^1R^2=NHCH(CH_3)_2$ and $n=3$]

Starting from the compound of Reference Example III-1, the titled compound was produced in the same manner as the one described in Example 7.

EXAMPLE 60

7(1H)-[3-(N-Benzylamino)propyloxyimino]-1a,7a-dihydro-1a-phenylcyclopropa[b]chromen [Compound of the general formula (I) wherein $A^1=H$; $A^2=H$; $B^1=H$; $B^2=H$; $NR^1R^2=NHCH_2$-$C_6H_5$ and $n=3$]

Starting from the compound of Reference Example IV-9, the titled compound was produced in the same manner as the one described in Example 1.

EXAMPLE 61

1a,7a-Dihydro-1a-phenyl-7(1H)-[3-(N-phenylethylamino)propyloxyimino]cyclopropa[b]chromen [Compound of the general formula (I) wherein $A^1=H$; $A^2=H$; $B^1=H$; $B^2=H$; $NR^1R^2=NHCH_2CH_2$-$C_6H_5$ and $n=3$]

Starting from the compound of Reference Example IV-9, the titled compound was produced in the same manner as the one described in Example 1.

EXAMPLE 62

1a,7a-Dihydro-7(1H)-(3-dimethylaminopropyloxyimino)-1a-phenylcyclopropa[b]chromen [Compound of the general formula (I) wherein $A^1=H$; $A^2=H$; $B^1=H$; $B^2=H$; $NR^1R^2=N(CH_3)_2$ and $n=3$]

Starting from the compound of Reference Example III-1, the titled compound was produced in the same manner as the one described in Example 7.

EXAMPLE 63

1a,7a-Dihydro-7(1H)-(3-dimethylaminopropyloxyimino)-4-fluoro-1a-phenylcyclopropa[b]chromen [Compound of the general formula (I) wherein $A^1=4$-F; $A^2=H$; $B^1=H$; $B^2=H$; $NR^1R^2=N(CH_3)_2$ and $n=3$]

Starting from the compound of Reference Example III-2, the titled compound was produced in the same manner as the one described in Example 7.

EXAMPLE 64

4-Chloro-1a,7a-dihydro-7(1H)-(3-dimethylamino-propyloxyimino)-1a-phenylcyclopropa[b]chromen [Compound of the general formula (I) wherein $A^1=4\text{-Cl}$; $A^2=H$; $B^1=H$; $B^2=H$; $NR^1R^2=N(CH_3)_2$ and $n=3$]

Starting from the compound of Reference Example III-3, the titled compound was produced in the same manner as the one described in Example 7.

EXAMPLE 65

4-Bromo-1a,7a-dihydro-7(1H)-(3-dimethylamino-propyloxyimino)-1a-phenylcyclopropa[b]chromen [Compound of the general formula (I) wherein $A^1=4\text{-Br}$; $A^2=H$; $B^1=H$; $B^2=H$; $NR^1R^2=N(CH_3)_2$ and $n=3$]

Starting from the compound of Reference Example III-4, the titled compound was produced in the same manner as the one described in Example 7.

EXAMPLE 66

1a,7a-Dihydro-7(1H)-(3-dimethylaminopropylox-yimino)-4-methoxy-1a-phenylcyclopropa[b]chromen [Compound of the general formula (I) wherein $A^1=4\text{-OCH}_3$, $A^2=H$; $B^1=H$; $B^2=H$; $NR^1R^2=N(CH_3)_2$ and $n=3$]

Starting from the compound of Reference Example III-5, the titled compound was produced in the same manner as the one described in Example 7.

EXAMPLE 67

1a,7a-Dihydro-7(1H)-(3-dimethylaminopropylox-yimino)-4-benzyloxy-1a-phenylcyclopropa[b]chromen [Compound of the general formula (I) wherein $A^1=4\text{-OCH}_2\text{-C}_6\text{H}_5$, $A^2=H$; $B^1=H$; $B^2=H$; $NR^1R^2=N(CH_3)_2$ and $n=3$]

Starting from the compound of Reference Example III-6, the titled compound was produced in the same manner as the one described in Example 7.

EXAMPLE 68

5-Chloro-1a,7a-dihydro-7(1H)-(3-dimethylamino-propyloxyimino)-1a-phenylcyclopropa[b]chromen [Compound of the general formula (I) wherein $A^1=5\text{-Cl}$; $A^2=H$; $B^1=H$; $B^2=H$; $NR^1R^2=N(CH_3)_2$ and $n=3$]

Starting from the compound of Reference Example III-7, the titled compound was produced in the same manner as the one described in Example 7.

EXAMPLE 69

1a,7a-Dihydro-7(1H)-(3-dimethylaminopropylox-yimino)-5-methoxy-1a-phenylcyclopropa[b]chromen [Compound of the general formula (I) wherein $A^1=5\text{-OCH}_3$, $A^2=H$; $B^1=H$; $B^2=H$; $NR^1R^2=N(CH_3)_2$ and $n=3$]

Starting from the compound of Reference Example III-8, the titled compound was produced in the same manner as the one described in Example 7.

EXAMPLE 70

1a,7a-Dihydro-7(1H)-(3-dimethylaminopropylox-yimino)-6-methoxy-1a-phenylcyclopropa[b]chromen [Compound of the general formula (I) wherein $A^1=6\text{-OCH}_3$; $A^2=H$; $B^1=H$; $B^2=H$; $NR^1R^2=N(CH_3)_2$ and $n=3$]

Starting from the compound of Reference Example III-9, the titled compound was produced in the same manner as the one described in Example 7.

EXAMPLE 71

1a,7a-Dihydro-7(1H)-(3-dimethylaminopropylox-yimino)-3,4-dimethoxy-1a-phenylcyclopropa[b]chromen [Compound of the general formula (I) wherein $A^1=3\text{-OCH}_3$; $A^2=4\text{-OCH}_3$; $B^1=H$; $B^2=H$; $NR^1R^2=N(CH_3)_2$ and $n=3$]

Starting from the compound of Reference Example III-10, the titled compound was produced in the same manner as the one described in Example 7.

EXAMPLE 72

4,5-Dichloro-1a,7a-dihydro-7(1H)-(3-dimethylamino-propyloxyimino)-1a-phenylcyclopropa[b]chromen [Compound of the general formula (I) wherein $A^1=4\text{-Cl}$; $A^2=5\text{-Cl}$; $B^1=H$; $B^2=H$; $NR^1R^2=N(CH_3)_2$ and $n=3$]

Starting from the compound of Reference Example III-11, the titled compound was produced in the same manner as the one described in Example 7.

EXAMPLE 73

1a,7a-Dihydro-4,5-dimethoxy-7(1H)-(3-dimethylamino-propyloxyimino)-1a-phenylcyclopropa[b]chromen [Compound of the general formula (I) wherein $A^1=4\text{-OCH}_3$; $A^2=5\text{-OCH}_3$; $B^1=H$; $B^2=H$; $NR^1R^2=N(CH_3)_2$ and $n=3$]

Starting from the compound of Reference Example III-12, the titled compound was produced in the same manner as the one described in Example 7.

EXAMPLE 74

4,5-Dibenzyloxy-1a,7a-dihydro-7(1H)-(3-dime-thylaminopropyloxyimino)cyclopropa[b]chromen [Compound of the general formula (I) wherein $A^1=4\text{-OCH}_2\text{-C}_6\text{H}_5$; $A^2=5\text{-OCH}_2\text{-C}_6\text{H}_5$; $B^1=H$; $B^2=H$; $NR^1R^2=N(CH_3)_2$ and $n=3$]

Starting from the compound of Reference Example III-13, the titled compound was produced in the same manner as the one described in Example 7.

EXAMPLE 75

1a,7a-Dihydro-7(1H)-(3-dimethylaminopropylox-yimino)-1a-(2-methoxyphenyl)cyclopropa[b]chromen [Compound of the general formula (I) wherein $A^1=H$; $A^2=H$; $B^12\text{-OCH}_3$; $B^2=H$; $NR^1R^2=N(CH_3)_2$ and $n=3$]

Starting from the compound of Reference Example III-14, the titled compound was produced in the same manner as the one described in Example 7.

EXAMPLE 76

1a,7a-Dihydro-7(1H)-(3-dimethylaminopropyloxyimino)-1a-(2-methylphenyl)cyclopropa[b]chromen [Compound of the general formula (I) wherein $A^1=H$; $A^2=H$; $B^1=2\text{-}CH_3$; $B^2=H$; $NR^1R^2=N(CH_3)_2$ and $n=3$]

Starting from the compound of Reference Example III-15, the titled compound was produced in the same manner as the one described in Example 7.

EXAMPLE 77

1a,7a-Dihydro-7(1H)-(3-dimethylaminopropyloxyimino)-1a-(3-chlorophenyl)cyclopropa[b]chromen [Compound of the general formula (I) wherein $A^1=H$; $A^2=H$; $B^1=3\text{-}Cl$; $B^2=H$; $NR^1R^2=N(CH_3)_2$ and $n=3$]

Starting from the compound of Reference Example III-16, the titled compound was produced in the same manner as the one described in Example 7.

EXAMPLE 78

1a,7a-Dihydro-7(1H)-(3-dimethylaminopropyloxyimino)-1a-(3-methoxyphenyl)cyclopropa[b]chromen [Compound of the general formula (I) wherein $A^1=H$; $A^2=H$; $B^1=3\text{-}OCH_3$; $B^2=H$; $NR^1R^2=N(CH_3)_2$ and $n=3$]

Starting from the compound of Reference Example III-17, the titled compound was produced in the same manner as the one described in Example 7.

EXAMPLE 79

1a,7a-Dihydro-7(1H)-(3-dimethylaminopropyloxyimino)-1a-(3-methylphenyl)cyclopropa[b]chromen [Compound of the general formula (I) wherein $A^1=H$; $A^2=H$; $B^1=3\text{-}CH_3$; $B^2=H$; $NR^1R^2=N(CH_3)_2$ and $n=3$]

Starting from the compound of Reference Example III-18, the titled compound was produced in the same manner as the one described in Example 7.

EXAMPLE 80

1a-(4-Chlorophenyl)-1a,7a-dihydro-7(1H)-(3-dimethylaminopropyloxyimino)cyclopropa[b]chromen [Compound of the general formula (I) wherein $A^1=H$; $A^2=H$; $B^1=4\text{-}Cl$; $B^2=H$; $NR^1R^2=N(CH_3)_2$ and $n=3$]

Starting from the compound of Reference Example III-19, the titled compound was produced in the same manner as the one described in Example 7.

EXAMPLE 81

1a,7a-Dihydro-7(1H)-(3-dimethylaminopropyloxyimino)-1a-(4-methoxyphenyl)cyclopropa[b]chromen [Compound of the general formula (I) wherein $A^1=H$; $A^2=H$; $B^1=4\text{-}OCH_3$; $B^2=H$; $NR^1R^2=N(CH_3)_2$ and $n=3$]

Starting from the compound of Reference Example III-20, the titled compound was produced in the same manner as the one described in Example 7.

EXAMPLE 82

1a,7a-Dihydro-7(1H)-(3-dimethylaminopropyloxyimino)-1a-(4-methylphenyl)cyclopropa[b]chromen [Compound of the general formula (I) wherein $A^1=H$; $A^2=H$; $B^1=4\text{-}CH_3$; $B^2=H$; $NR^1R^2=N(CH_3)_2$ and $n=3$]

Starting from the compound of Reference Example III-21, the titled compound was produced in the same manner as the one described in Example 7.

EXAMPLE 83

1a,7a-Dihydro-7(1H)-(3-dimethylaminopropyloxyimino)-1a-(4-trifluoromethylphenyl)cyclopropa[b]chromen [Compound of the general formula (I) wherein $A^1=H$; $A^2=H$; $B^1=4\text{-}CF_3$; $B^2=H$; $NR^1R^2=N(CH_3)_2$ and $n=3$]

Starting from the compound of Reference Example III-22, the titled compound was produced in the same manner as the one described in Example 7.

EXAMPLE 84

1a,7a-Dihydro-7(1H)-(3-dimethylaminopropyloxyimino)-1a-(4-methoxycarbonylphenyl)cyclopropa[b]chromen [Compound of the general formula (I) wherein $A^1=H$; $A^2=H$; $B^1=4\text{-}CO_2CH_3$; $B^2=H$; $NR^1R^2=N(CH_3)_2$ and $n=3$]

Starting from the compound of Reference Example III-23, the titled compound was produced in the same manner as the one described in Example 7.

EXAMPLE 85

1a-(4-Cyanophenyl)-1a,7a-dihydro-7(1H)-(3-dimethylaminopropyloxyimino)cyclopropa[b]chromen [Compound of the general formula (I) wherein $A^1=H$; $A^2=H$; $B^1=4\text{-}CN$; $B^2=H$; $NR^1R^2=N(CH_3)_2$ and $n=3$]

Starting from the compound of Reference Example III-24, the titled compound was produced in the same manner as the one described in Example 7.

EXAMPLE 86

1a,7a-Dihydro-7(1H)-(2-dimethylaminopropyloxyimino)-1a-(4-nitrophenyl)cyclopropa[b]chromen [Compound of the general formula (I) wherein $A^1=H$; $A^2=H$; $B^1=4\text{-}NO_2$; $B^2=H$; $NR^1R^2=N(CH_3)_2$ and $n=3$]

Starting from the compound of Reference Example III-25, the titled compound was produced in the same manner as the one described in Example 7.

EXAMPLE 87

1a-(3,4-Dichlorophenyl)-1a,7a-dihydro-7(1H)-(3-dimethylaminopropyloxyimino)cyclopropa[b]chromen [Compound of the general formula (I) wherein $A^1=H$; $A^2=H$; $B^1=3\text{-}Cl$; $B^2=4\text{-}Cl$; $NR^1R^2=N(CH_3)_2$ and $n=3$]

Starting from the compound of Reference Example III-26, the titled compound was produced in the same manner as the one described in Example 7.

EXAMPLE 88

1a,7a-Dihydro-7(1H)-(3-dimethylaminopropyloxyimino)-1a-(3,4-dimethoxyphenyl)cyclopropa[b]chromen [Compound of the general formula (I) wherein $A^1=H$; $A^2=H$; $B^1=3\text{-}OCH_3$; $B^2=4\text{-}OCH_3$; $NR^1R^2=N(CH_3)_2$ and $n=3$]

Starting from the compound of Reference Example III-27, the titled compound was produced in the same manner as the one described in Example 7.

EXAMPLE 89

4-Chloro-1a-(4-chlorophenyl)-1a,7a-dihydro-7(1H)-(3-dimethylaminopropyloxyimino)cyclopropa[b]chromen [Compound of the general formula (I) wherein $A^1=4\text{-}Cl$; $A^2=H$; $B^1=4\text{-}Cl$; $B^2=H$; $NR^1R^2=N(CH_3)_2$ and $n=3$]

Starting from the compound of Reference Example III-28, the titled compound was produced in the same manner as the one described in Example 7.

EXAMPLE 90

4-Chloro-1a,7a-dihydro-7(1H)-(3-dimethylaminopropyloxyimino)-1a-(4-nitrophenyl)cyclopropa[b]chromen [Compound of the general formula (I) wherein $A^1=4\text{-}Cl$; $A^2=H$; $B^1=4\text{-}NO_2$, $B^2=H$; $NR^1R^2=N(CH_3)_2$ and $n=3$]

Starting from the compound of Reference Example III-29, the titled compound was produced in the same manner as the one described in Example 7.

EXAMPLE 91

1a,7a-Dihydro-7(1H)-(3-dimethylaminopropyloxyimino)-4-hydroxy-1a-phenylcyclopropa[b]chromen [Compound of the general formula (I) wherein $A^1=4\text{-}OH$; $A^2=H$; $B^1=H$; $B^2=H$; $NR^1R^2=N(CH_3)_2$ and $n=3$]

93 mg of 10% palladium on carbon was suspended in 6 ml of ethyl acetate and subjected to hydrogen-replacement under suction. Next, 311 mg of the compound of Example 67 was added thereto and the mixture was stirred under a hydrogen gas stream (atmospheric pressure) at room temperature for 24 hours. After filtering, the filtrate was concentrated and introduced through a silica gel column chromatography with the use of methylene chloride/methanol (9:1) as the eluent. Thus 195 mg (yield: 78%) of the titled compound was obtained.

EXAMPLE 92

4-Acetyloxy-1a,7a-dihydro-7(1H)-(3-dimethylaminopropyloxyimino)-1a-phenylcyclopropa[b]chromen [Compound of the general formula (I) wherein $A^1=4\text{-}OCOCH_3$; $A^2=H$; $B^1=H$; $B^2=H$; $NR^1R^2=N(CH_3)_2$ and $n=3$]

300 mg of the compound of Example 91 was dissolved in 10 ml of pyridine and 5 ml of acetic anhydride. After stirring at room temperature for 1 hour, the solvent was distilled off and the residue was dissolved in methylene chloride. Next it was washed with an aqueous solution of sodium hydrogencarbonate and then with water and dried over anhydrous magnesium sulfate. After filtering, the filtrate was concentrated and introduced through a silica gel column chromatography with the use of methylene chloride/methanol (9:1) as the eluent. Thus 329 mg (yield: 98.0%) of the titled compound was obtained.

EXAMPLE 93

1a,7a-Dihydro-4-(N,N-dimethylcarbamoyloxy)-7(1H)-(3-dimethylaminopropyloxyimino)-1a-phenylcyclopropa[b]chromen [Compound of the general formula (I) wherein $A^1=4\text{-}OCON(CH_3)_2$; $A^2=H$; $B^1=H$; $B^2=H$; $NR^1R^2=N(CH_3)_2$ and $n=3$]

139 mg of the compound of Example 91 was dissolved in 20 ml of methylene chloride. After adding 0.11 ml (3 equivalents) of N,N-dimethylcarbamoyl chloride and 0.55 ml (10 equivalents) of triethylamine, the mixture was heated under reflux for 7 hours. The reaction mixture was cooled, washed with an aqueous solution of sodium hydrogencarbonate and then with water and dried over anhydrous magnesium sulfate. After filtering and concentrating, the obtained residue was purified through silica gel column chromatography by using methylene chloride/methanol (95:5) as the eluent. Thus 144 mg (yield: 86.2%) of the titled compound was obtained.

EXAMPLE 94

4-(2-Amino-2-oxoethyloxy)-1a,7a-dihydro-7(1H)-(3-dimethylaminopropyloxyimino)-1a-phenylcyclopropa[b]chromen [Compound of the general formula (I) wherein $A^1=4\text{-}OCH_2CONH_2$; $A^2=H$; $B^1=H$; $B^2=H$; $NR^1R^2=N(CH_3)_2$ and $n=3$]

129 mg of the compound of Example 91 was dissolved in 20 ml of dioxane. After adding 21.9 mg (1.5 equivalents) of sodium hydride (60% oil dispersion), the mixture was heated to 100° C. for 30 minutes. Next, 72.2 mg (2 equivalents) of 2-chloroacetamide and 0.5 ml of dimethylsulfoxide were added thereto and the mixture was stirred at 100° C. for 3 hours. The reaction mixture was concentrated and ice/water was added thereto. After extracting with ether, the ether layer was washed with water and dried over anhydrous magnesium sulfate. After filtering and concentrating, the obtained residue was purified with a silica gel column chromatography by using methylene chloride/methanol (9:1) as the eluent. Thus 94.3 mg (yield: 62.9%) of the titled compound was obtained.

EXAMPLE 95

1a,7a-Dihydro-4,5-dihydroxy-7(1H)-(3-dimethylaminopropyloxyimino)cyclopropa[b]chromen [Compound of the general formula (I) wherein $A^1=4\text{-}OH$; $A^2=5\text{-}OH$; $B^1=H$; $B^2=H$; $NR^1R^2=N(CH_3)_2$ and $n=3$]

48 mg of 10% palladium on carbon was suspended in 20 ml of ethyl acetate and subjected to hydrogen-replacement under suction. 240 mg of the compound of Example 74 was added thereto and the mixture was stirred under a hydrogen stream (atmospheric pressure) at room temperature for 5 hours. Then it was treated in the same manner as the one described in Example 91. Thus 67.0 mg (yield: 41.5%) of the titled compound was obtained.

EXAMPLE 96

1a,7a-Dihydro-7(1H)-(3-diethylaminopropyloxyimino)-1a-phenylcyclopropa[b]chromen [Compound of the general formula (I) wherein $A^1=H$; $A^2=H$; $B^1=H$; $B^2=H$; $NR^1R^2=N(C_2H_5)_2$ and $n=3$]

Starting from the compound of Reference Example IV-9, the titled compound was produced in the same manner as the one described in Example 1.

EXAMPLE 97

1a,7a-Dihydro-7(1H)-(3-dipropylaminopropyloxyimino)-1a-phenylcyclopropa[b]chromen [Compound of the general formula (I) wherein $A^1=H$; $A^2=H$; $B^1=H$; $B^2=H$; $NR^1R^2=N(CH_2CH_2CH_3)_2$ and $n=3$]

Starting from the compound of Reference Example IV-8, the titled compound was produced in the same manner as the one described in Example 1.

EXAMPLE 98

1a,7a-Dihydro-1a-phenyl-7(1H)-(3-pyrrolidinylpropyloxyimino)cyclopropa[b]chromen [Compound of the general formula (I) wherein $A^1=H$; $A^2=H$; $B^1=H$; $B^2=H$; $NR^1R^2=$pyrrolidinyl and $n=3$]

Starting from the compound of Reference Example IV-9, the titled compound was produced in the same manner as the one described in Example 1.

EXAMPLE 99

1a,7a-Dihydro-7(1H)-[3-(4-methyl-1-piperazinyl)-propyloxyimino]-1a-phenylcyclopropa[b]chromen [Compound of the general formula (I) wherein $A^1=H$; $A^2=H$; $B^1=H$; $B^2=H$;

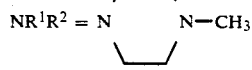

and $n=3$]

Starting from the compound of Reference Example IV-9, the titled compound was produced in the same manner as the one described in Example 1.

EXAMPLE 100

1a,7a-Dihydro-1a-phenyl-7(1H)-[3-(1-piperidinyl)-propyloxyimino]-cyclopropa[b]chromen [Compound of the general formula (I) wherein $A^1=H$; $A^2=H$; $B^1=H$; $B^2=H$; $NR^1R^2=$piperidinyl and $n=3$]

Starting from the compound of Reference Example IV-9, the titled compound was produced in the same manner as the one described in Example 1.

EXAMPLE 101

1a,7a-Dihydro-7(1H)-[3-(1-homopiperidinyl)propyloxyimino]-1a-phenylcyclopropa[b]chromen [Compound of the general formula (I) wherein $A^1=H$; $A^2=H$; $B^1=H$; $B^2=H$; $NR^1R^2=$homopiperidinyl and $n=3$]

Starting from the compound of Reference Example IV-9, the titled compound was produced in the same manner as the one described in Example 1.

EXAMPLE 102

1a,7a-Dihydro-7(1H)-(3-dimethylamino-2-methylpropyloxyimino)-1a-phenylcyclopropa[b]chromen [Compound of the general formula (I) wherein $A^1=H$; $A^2=H$; $B^1=H$; $B^2=H$; $NO(CH_2)_nNR^1R^2=NOCH_2CH(CH_3)CH_2N(CH_3)_2$ and $n=3$]

Starting from the compound of Reference Example III-1, the titled compound was produced in the same manner as the one described in Example 7.

EXAMPLE 103

7(1H)-[3-(N-Benzyl-N-methylamino)propyloxyimino]-1a,7a-dihydro-1a-phenylcyclopropa[b]chromen [Compound of the general formula (I) wherein $A^1=H$; $A^2=H$; $B^1=H$; $B^2=H$; $NR^1R^2=N(CH_3)CH_2$-$C_6H_5$ and $n=3$]

Starting from the compound of Reference Example IV-9, the titled compound was produced in the same manner as the one described in Example 1.

EXAMPLE 104

1a,7a-Dihydro-1a-phenyl-7(1H)-[3-(1-pyrrolidonyl)-propyloxyimino]cyclopropa[b]chromen [Compound of the general formula (I) wherein $A^1=H$; $A^2=H$; $B^1=H$; $B^2=H$; $NR^1R^2=$pyrrolidonyl and $n=3$]

Starting from the compound of Reference Example IV-9, the titled compound was produced in the same manner as the one described in Example 1.

EXAMPLE 105

1a,7a-Dihydro-1a-phenyl-7(1H)-[2-(8-pyrrolitidinyl)ethyloxyimino]cyclopropa[b]chromen [Compound of the general formula (I) wherein $A^1=H$; $A^2=H$; $B^1=H$; $B^2=H$ and

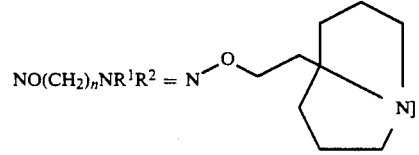

Starting from the compound of Reference Example III-1, the titled compound was produced in the same manner as the one described in Example 7.

EXAMPLE 106

4-Chloro-1a,7a-dihydro-7(1H)-(2-hydroxy-3-isopropylaminopropyloxyimino)-1a-phenylcyclopropa[b]chromen [Compound of the general formula (I) wherein $A^1=4$-Cl; $A^2=H$; $B^1=H$; $B^2=H$;

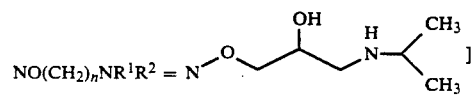

Starting from the compound of Reference Example IV-17, the titled compound was produced in the same manner as the one described in Example 1.

EXAMPLE 107

1a,7a-Dihydro-7(1H)-(4-methylaminobutyloxyimino)-1a-phenylcyclopropa[b]chromen [Compound of the general formula (I) wherein $A^1=H$; $A^2=H$; $B^1=H$; $B^2=H$; $NR^1R^2=NHCH_3$ and $n=4$]

Starting from the compound of Reference Example IV-14, the titled compound was produced in the same manner as the one described in Example 1.

EXAMPLE 108

1a,7a-Dihydro-7(1H)-(4-dimethylaminobutyloxyimino)-1a-phenylcyclopropa[b]chromen [Compound of the general formula (I) wherein $A^1=H$; $A^2=H$; $B^1=H$; $B^2=H$; $NR^1R^2=N(CH_3)_2$ and $n=4$]

Starting from the compound of Reference Example IV-14, the titled compound was produced in the same manner as the one described in Example 1.

EXAMPLE 109

1a,7a-Dihydro-7(1H)-(5-dimethylaminopentyloxyimino)-1a-phenylcyclopropa[b]chromen [Compound of the general (I) wherein $A^1=H$; $A^2=h$; $B^1=H$; $B^2=H$; $NR^1R^2=N(CH_3)_2$ and $n=5$]

Starting from the compound of Reference Example IV-15, the titled compound was produced in the same manner as the one described in Example 1.

EXAMPLE 110

4-Chloro-1a-(4-chlorophenyl)-1a,7a-dihydro-7(1H)-(4-methylaminobutyloxyimino)cyclopropa[b]chromen [Compound of the general formula (I) wherein $A^1=4$-Cl; $A^2=H$; $B^1=4$-Cl; $B^2=H$; $NR^1R^2=NHCH_3$ and $n=4$]

Starting from the compound of Reference Example IV-16, the titled compound was produced in the same manner as the one described in Example 1.

The physicochemical data of the compounds produced in the above Examples are given in Table 4.

TABLE 4

| Example | Structure | m.p. (°C.) | IR | NMR | Elementary Analysis/MS |
|---|---|---|---|---|---|
| 1 | (structure: N-methylaminoethyl oxime of phenyl cyclopropane chromene) | hygroscopic | 2900 2780<br>1610 1450<br>1380 1340<br>1305 1250<br>1225 1040<br>970 940<br>870 760<br>740 690 | 1.62(t, 1H, J=6.6Hz)<br>1.90(dd, 1H, J=6.6Hz & 10.6Hz)<br>2.49(s, 3H), 2.96(t, 2H, J=5.3Hz)<br>3.02(dd, 1H, J=6.6Hz & 10.6Hz)<br>4.32(t, 2H, J=5.3Hz)<br>6.95–7.49(m, 8H)<br>7.81(dd, 1H, J=1.5Hz & 7.9Hz) | L-tartrate.5/4H$_2$O<br>  C    H    N<br>Calc.: 57.43 5.76 5.82<br>Found: 57.30 5.84 5.68 |
| 2 | (structure: Cl-substituted analog) | 75–78<br>L-tartrate | 2930<br>1610 1475<br>1450 1415<br>1215 1040<br>980 920<br>808 746<br>609 | 1.62(t, 1H, J=6.6Hz)<br>1.91(dd, 1H, J=6.6Hz & 10.6Hz)<br>2.48(s, 3H)2.9–3.05(m, 3H)<br>4.31(t, 2H, J=5.3Hz)<br>6.9–7.01(m, 2H)<br>7.3–7.5(m, 5H)<br>7.76(d, 1H, J=8.6Hz) | L-tartrate.1H$_2$O<br>  C    H    N<br>Calc.: 54.06 5.33 5.48<br>Found: 54.11 5.38 5.34 |
| 3 | (structure: Br-substituted analog) | 163–170<br>L-tartrate | 2920 1602<br>1585 1470<br>1442 1405<br>1300 1215<br>1102 1040<br>975 912<br>802 742<br>685 | 1.59(t, 1H, J=7.3Hz)<br>1.91(dd, 1H, J=7.3Hz & 10.6Hz)<br>2.48(s, 3H)2.9–3.05(m, 3H)<br>4.31(t, 2H, J=5.3Hz)<br>7.10(dd, 1H, J=2.0Hz & 8.3Hz)<br>7.17(d, 1H, J=2.0Hz)<br>7.3–7.5(m, 5H)<br>7.69(d, 1H, J=8.6Hz) | L-tartrate<br>  C    H    N<br>Calc.: 51.40 4.69 5.21<br>Found: 51.29 4.90 5.50 |
| 4 | (structure: dimethoxy-substituted analog) | 88–89<br>L-tartrate | 2930 2840<br>1600 1500<br>1455 1420<br>1380 1310<br>1260 1215<br>1165 1080<br>1040 860<br>800 755<br>695 | 1.57(t, 1H, J=6.6Hz)<br>1.88(dd, 1H, J=6.6Hz & 10.6Hz)<br>2.49(s, 3H), 2.94(t, 2H, J=5.1Hz)<br>2.97(dd, 1H, J=6.6Hz & 10.6Hz)<br>3.87(s, 3H), 3.89(s, 3H)<br>4.31(t, 2H, J=5.1Hz)<br>6.49(s, 1H)<br>7.22–7.49(m, 6H) | L-tartrate.1H$_2$O<br>  C    H    N<br>Calc.: 55.96 6.01 5.22<br>Found: 55.79 6.06 4.91 |

TABLE 4-continued

| | | | | |
|---|---|---|---|---|
| 5 | 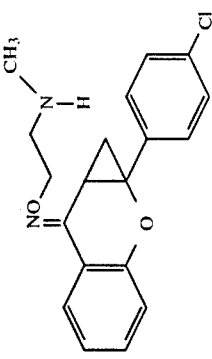 | hygroscopic | 2930 2850<br>1610 1480<br>1450 1380<br>1310 1255<br>1230 1100<br>1090 1040,<br>975 940<br>880 815<br>760 | 1.63(t, 1H, J=6.6Hz)<br>1.85(dd, 1H, J=6.6Hz & 10.6Hz)<br>2.48(s, 3H), 2.95(t, 2H, J=5.3Hz)<br>2.97(dd, 1H, J=6.6Hz & 10.6Hz)<br>4.32(t, 2H, J=5.3Hz)<br>6.95–7.42(m, 7H)<br>7.81(dd, 1H, J=1.3Hz & 7.9Hz) | L-tartrate.1H$_2$O<br>    C    H    N<br>Calc.: 54.07 5.33 5.48<br>Found: 53.76 5.22 5.42 |
| 6 | 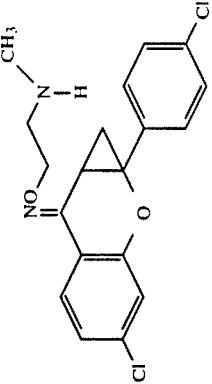 | 88–93<br>L-tartrate | 2930 2870<br>2790 1612<br>1598 1480<br>1415 1380<br>1308 1225<br>1098 1050<br>982 920<br>885 815<br>755 | 1.60(t, 1H, J=6.6Hz)<br>1.86(dd, 1H, J=6.6Hz & 10.9Hz)<br>2.48(s, 3H)2.9–3.05(m, 3H)<br>4.25–4.35(m, 2H)<br>6.9–7.0(m, 2H)<br>7.37(s, 4H)<br>7.76(d, 1H, J=8.6Hz) | L-tartrate 5/4H$_2$O<br>    C    H    N<br>Calc.: 50.23 4.85 5.09<br>Found: 50.00 4.73 5.00 |
| 7 | 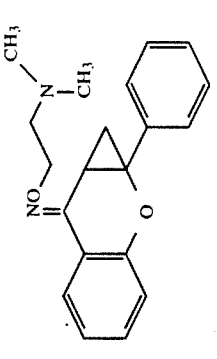 | 115–118<br>maleate | 2960 2940<br>2820 2760<br>1615 1600<br>1450 1250<br>1230 1030<br>760 740<br>690 | 1.62(t, 1H, J=6.4Hz)<br>1.87(dd, 1H, J=6.4Hz & 10.9Hz)<br>2.30(s, 6H), 2.69(t, 2H, J=5.8Hz)<br>3.03(dd, 1H, J=6.4Hz & 10.9Hz)<br>4.18–4.42(m, 2H)<br>6.95–7.85(m, 9H) | oleate.½H$_2$O<br>    C    H    N<br>Calc.: 64.41 6.08 6.26<br>Found: 64.86 6.06 6.29 |
| 8 | 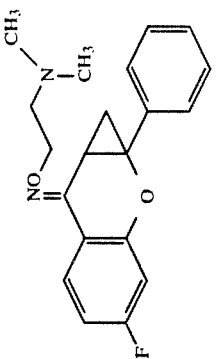 | 148.5–150<br>maleate | 2940 1620<br>1602 1500<br>1430 1260<br>1210 1148<br>1025 995<br>845 | 1.59(t, 1H, J=6.6Hz)<br>1.89(dd, 1H, J=6.6Hz & 10.6Hz)<br>2.31(s, 6H), 2.69(t, 2H, J=5.9Hz)<br>3.02(dd, 1H, J=6.6Hz & 10.6Hz)<br>4.24–4.35(m, 2H)<br>6.65–6.75(m, 2H)7.29–7.5(m, 5H)<br>7.79–7.85(m, 1H) | maleate    C    H    N<br>Calc.: 63.15 5.52 6.13<br>Found: 63.00 5.62 6.08 |

TABLE 4-continued

| | | | | |
|---|---|---|---|---|
| 9 | 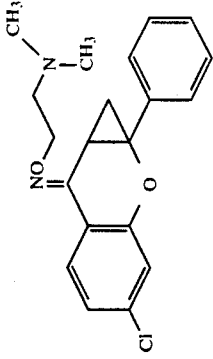 | 164-166 maleate | 3060 2950 2820 2770 1620 1605 1560 1420 1230 1040 980 750 695 | 1.58(t, 1H, J=6.6Hz) 1.89(dd, 1H, J=6.6Hz & 10.6Hz) 2.31(s, 6H)2.7(t, 2H, J=5.9Hz) 3.02(dd, 1H, J=6.6Hz & 10.6Hz) 4.30(m, 2H) 6.95(dd, 1H, J=2.3Hz & 8.6Hz) 6.99(d, 1H, J=2.3Hz) 7.27-7.50(m, 5H) 7.77(d, 1H, J=8.6Hz) | HiMS Calc.: 356.1288 Found: 356.1271 |
| 10 | 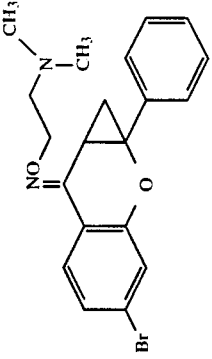 | 164.5-165.5 maleate | 2950 1610 1595 1480 1415 1310 1205 1040 980 920 860 720 | 1.5-1.65(m, 1H) 1.89(dd, 1H, J=6.6Hz & 10.6Hz) 2.31(s, 6H), 2.69(t, 2H, J=5.9Hz) 3.01(dd, 1H, J=6.6Hz & 10.6Hz) 4.25-4.35(m, 2H) 7.09(dd, 1H, J=2.0Hz & 8.3Hz) 7.15-7.17(m, 1H) 7.3-7.5(m, 5H) 7.70(d, 1H, J=8.6Hz) | maleate.1/6H$_2$O Calc.: C 55.39 H 4.91 N 5.38 Found: 55.04 4.87 5.26 |
| 11 | 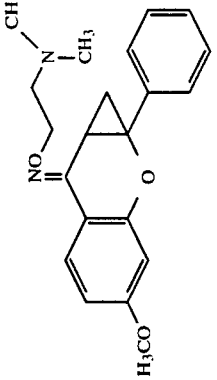 | oil | 2920 2800 2750 1615 1580 1495 1440 1420 1380 1340 1280 1260 1190 1160 1080 1025 990 750 | 1.58(t, 1H, J=6.6Hz) 1.87(dd, 1H, J=6.6Hz & 10.2Hz) 2.32(s, 6H), 2.70(t, 2H, J=5.8Hz) 2.98(dd, 1H, J=6.6Hz & 10.2Hz) 3.79(s, 3H), 4.29(m, 2H) 4.47-7.76(m, 8H) | HiMS Calc.: 352.1785 Found: 352.1765 |
| 12 | 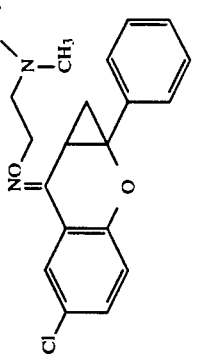 | 144.5-148 maleate | 3050 2940 2820 2770 1615 1595 1470 1450 1430 1375 1290 1250 1225 1110 1035 980 882 810 760 700 | 1.58(t, 1H, J=7.3Hz) 1.89(dd, 1H, J=7.3Hz & 10.6Hz) 2.32(s, 6H) 2.70(t, 2H, J=5.9Hz) 3.01(dd, 1H, J=7.3Hz & 10.6Hz) 4.25-4.4(m, 2H) 6.91(d, 1H, J=9.2Hz) 7.23-7.5(m, 6H) 7.81(d, 1H, J=2.6Hz) | maleate Calc.: C 60.95 H 5.33 N 5.92 Found: 60.78 5.34 5.89 |

TABLE 4-continued

| | Structure | mp / salt | IR | NMR | Analysis |
|---|---|---|---|---|---|
| 13 | 4-methoxy chromene with cyclopropyl-phenyl and N(CH₃)₂ oxime-ethyl | 145–146 maleate | 2930 2750 1600 1480 1450 1430 1300 1250 1215 1080 1035 980 860 820 | 1.57(t, 1H, J=6.6Hz) 1.84(dd, 1H, J=6.6Hz & 10.6Hz) 2.31(s, 6H), 2.70(t, 2H, J=5.9Hz) 3.01(dd, 1H, J=6.6Hz & 10.6Hz) 3.81(s, 3H) 4.32(t, 2H, J=5.9Hz) 6.90–7.47(m, 8H) | maleate.½H₂O<br>    C    H    N<br>Calc.: 64.14 6.58 5.54<br>Found: 64.18 6.12 5.97 |
| 14 | 8-methoxy chromene analog | citrate hygroscopic | 2930 2750 1600 1450 1380 1330 1275 1240 1220 1095 1030 930 840 780 750 725 690 | 1.66(t, 1H, J=6.6Hz) 1.75(dd, 1H, J=6.6Hz & 10.6Hz) 2.33(s, 6H), 2.68–2.80(m, 2H) 3.29(dd, 1H, J=6.6Hz & 10.6Hz) 3.88(s, 3H), 4.29–4.38(m, 2H) 6.57–6.64(m, 2H) 7.18–7.48(m, 6H) | MS<br>352(M⁺) |
| 15 | 6,7-dichloro chromene analog | 177–179 maleate | 2940 2820 2760 1615 1465 1402 1280 1235 1122 1035 988 885–760 742 | 1.45–1.55(m, 1H) 1.90(dd, 1H, J=6.6Hz & 10.6Hz) 2.31(s, 6H)2.69(t, 2H, J=6.1Hz) 2.99(dd, 1H, J=6.6Hz & 10.6Hz) 4.25–4.35(m, 2H)7.10(s, 1H) 7.3–7.45(m, 5H) 7.91(s, 1H) | maleate.½H₂O<br>    C    H    N<br>Calc.: 56.31 4.82 5.47<br>Found: 56.37 4.70 5.43 |
| 16 | 6,7-dimethoxy chromene analog | 122–125 maleate | 2920 2800 2750 1600 1500 1445 1415 1250 1205 1190 1160 1080 1030 860 800 750 690 | 1.55(t, 1H, J=6.6Hz) 1.85(dd, 1H, J=6.6Hz & 10.6Hz) 2.32(s, 6H), 2.70(t, 2H, J=5.9Hz) 2.99(dd, 1H, J=6.6Hz & 10.6Hz) 3.86(s, 3H), 3.89(s, 3H) 4.30(t, 2H, J=5.9Hz) 6.49(s, 1H) 7.25–7.47(m, 6H) | maleate<br>    C    H    N<br>Calc.: 62.64 6.07 5.62<br>Found: 62.65 6.17 5.60 |

TABLE 4-continued

| | | | | |
|---|---|---|---|---|
| 17 | 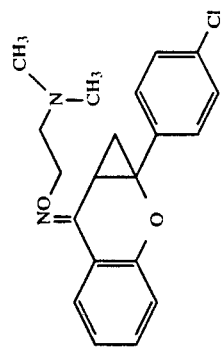 | 113–114 maleate | 3050 2940 2810 2760 1615 1495 1460 1380 1315 1255 1235 1095 1035 980 885 820 760 750 | 1.62(t, 1H, J=6.6Hz) 1.84(dd, 1H, J=6.6Hz & 10.5Hz) 2.41(s, 6H), 2.82(dd, 1H, J=5.7Hz) 3.02(dd, 1H, J=6.6Hz & 10.5Hz) 4.37(t, 2H, J=5.7Hz) 6.95–7.41(m, 7H) 7.81(d, 1H, J=7.9Hz) | maleate.1H$_2$O    C    H    N Calc.: 60.18 5.68 5.85 Found: 60.21 5.25 5.84 |
| 18 | 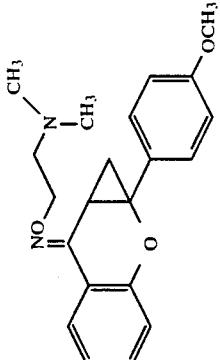 | 109–110 maleate | 2930 2800 2760 1610 1510 1450 1460 1385 1300 1245 1230 1170 1100 1030 970 820 770 760 740 | 1.56(t, 1H, J=6.6Hz) 1.82(dd, 1H, J=6.6Hz & 10.6Hz) 2.32(s, 6H), 2.70(t, 2H, J=5.9Hz) 2.98(dd, 1H, J=6.6Hz & 10.6Hz) 3.82(s, 3H), 4.31(t, 2H, J=5.9Hz) 6.91–7.42(m, 7H) 7.82(dd, 1H, J=1.3Hz & 8.1Hz) | maleate Calc.: 63.99 6.12 5.95 Found: 64.09 6.02 5.98 |
| 19 | 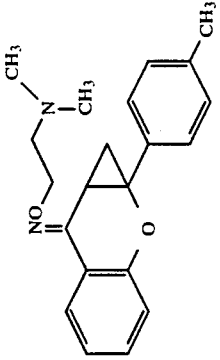 | 137–139 maleate | 2940 2880 2820 2770 1620 1485 1460 1385 1315 1260 1235 1105 1040 980 890 810 765 750 | 1.57(t, 1H, J=6.6Hz) 1.83(dd, 1H, J=6.6Hz & 10.6Hz) 2.31(s, 6H), 2.35(s, 3H), 2.69(t, 2H, J=5.9Hz) 3.01(dd, 1H, J=6.6Hz & 10.6Hz) 4.30(t, 2H, J=5.9Hz) 6.93–7.36(m, 7H) 7.82(dd, 1H, J=1.3Hz & 8.1Hz) | maleate.½H$_2$O Calc.: 66.65 6.77 5.76 Found: 66.26 6.31 6.14 |
| 20 | 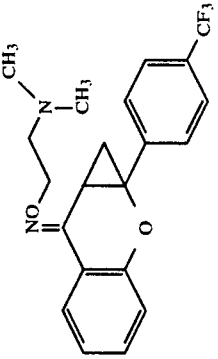 | 56–58 maleate | 2940 2860 2820 2770 1615 1480 1455 1410 1320 1255 1235 1170 1120 1030 980 950 825 760 | 1.69(t, 1H, J=7.3Hz) 1.90(dd, 1H, J=7.3Hz & 10.6Hz) 2.33(s, 6H), 2.73(t, 2H, J=5.7Hz) 3.09(dd, 1H, J=7.3Hz & 10.6Hz) 4.33(t, 2H, J=5.7Hz) 6.98–7.67(m, 7H) 7.84(dd, 1H, J=2.0Hz & 7.9Hz) | maleate.½H$_2$O Calc.: 58.25 5.08 5.43 Found: 58.25 5.06 5.41 |

TABLE 4-continued

| | | | | NMR | |
|---|---|---|---|---|---|
| 21 | [structure: chromene with =N-O-CH2CH2-N(CH3)2 oxime ether and cyclopropane bearing 4-CO2CH3-phenyl] | 116-118 maleate | 2930 1720 1610 1455 1435 1400 1380 1315 1280 1235 1180 1115 1040 980 950 840 825 760 740 700 | 1.69(t, 1H, J=7.2Hz) 1.91(dd, 1H, J=7.2Hz & 10.5Hz) 2.34(s, 6H), 2.74(t, 2H, J=5.9Hz) 3.09(dd, 1H, J=7.2Hz & 10.5Hz) 3.93(s, 3H)4.34(t, 2H, J=5.9Hz) 6.97-8.07(m, 8H) | maleate.½H2O  C  H  N Calc.: 62.33 5.73 5.59 Found: 62.34 5.60 5.55 |
| 22 | [structure: chromene with =N-O-CH2CH2-N(CH3)2 oxime ether and cyclopropane bearing 4-CN-phenyl] | 128-130 maleate | 2940 2230 2860 2820 1615 1480 1460 1380 1310 1255 1200 1102 1030 980 820 710 | 1.72(t, 1H, J=7.3Hz) 1.89(dd, 1H, J=7.3Hz & 10.6Hz) 2.31(s, 6H), 2.70(t, 2H, J=5.9Hz) 3.10(dd, 1H, J=7.3Hz & 10.6Hz) 4.25-4.40(m, 2H)6.95-7.05(m, 2H) 7.30-7.40(m, 1H) 7.53(d, 2H, J=7.9Hz) 7.69(d, 2H, J=7.9Hz) 7.83(dd, 1H, J=2.0Hz & 8.3Hz) | maleate  C  H  N Calc.: 64.78 5.44 9.07 Found: 65.15 5.49 9.07 |
| 23 | [structure: chromene with =N-O-CH2CH2-N(CH3)2 oxime ether and cyclopropane bearing 4-NO2-phenyl] | 142-144 maleate | 3070 2950 2770 1605 1520 1480 1345 1260 1235 1105 1040 855 840 765 745 | 1.76(t, 1H, J=7.3Hz) 1.94(dd, 1H, J=10.6Hz & 7.3Hz) 2.32(s, 6H), 2.70(t, 2H, J=5.9Hz) 3.14(dd, 1H, J=7.3Hz & 10.6Hz) 4.32(m, 2H)7.03(m, 2H) 7.32(m, 2H)7.58(d, 2H, J=9.2Hz) 7.84(dd, 1H, J=8.6Hz & 1.3Hz) 8.26(d, 2H, J=9.2Hz) | maleate  C  H  N Calc.: 59.62 5.21 8.69 Found: 59.49 5.20 8.61 |
| 24 | [structure: chromene with =N-O-CH2CH2-N(CH3)2 oxime ether and cyclopropane bearing 3,4-dichlorophenyl] | 110-111.5 maleate | 2940 2830 2780 1618 1480 1460 1380 1310 1205 1128 1105 1028 980 945 815 | 1.64(t, 1H, J=6.6Hz) 1.83(dd, 1H, J=6.6Hz & 10.6Hz) 2.32(s, 6H), 2.70(t, 2H, J=5.9Hz) 3.03(dd, 1H, J=6.6Hz & 10.6Hz) 4.25-4.4(m, 2H) 6.95-7.05(m, 2H ) 7.21-7.36(m, 2H) 7.46(d, 1H, J=8.6Hz) 7.56(d, 1H, J=2.0Hz) 7.8-7.85(m, 1H) | maleate  C  H  N Calc.: 56.81 4.77 5.52 Found: 56.74 4.66 5.49 |

TABLE 4-continued

| | | | | | |
|---|---|---|---|---|---|
| 25 | structure with N(CH₃)₂ ethyl oxime, chromane, 4-Cl phenyl | 122–123.5 maleate | 2930 2760<br>1610 1598<br>1480 1415<br>1308 1220<br>1098 1070<br>1030 982<br>920 810<br>755 | 1.55–1.7(m, 1H)<br>1.85(dd, 1H, J=7.3Hz & 10.6Hz)<br>2.31(s, 6H),<br>2.69(t, 2H, J=5.9Hz)<br>2.99(dd, 1H, J=7.3Hz & 10.6Hz)<br>4.2–4.4(m, 2H)<br>6.9–7.0(m, 2H)7.36(s, 4H)<br>7.77(d, 1H, J=8.6Hz) | maleate<br>C H N<br>Calc.: 56.81 4.77 5.52<br>Found: 56.63 4.59 5.48 |
| 26 | structure with N(CH₂CH₃)₂ ethyl oxime, chromane, phenyl | 148.0–148.5 citrate | 2960 2800<br>1615 1455<br>1380 1345<br>1310 1255<br>1230 1030<br>980 870<br>760 740<br>690 | 1.06(t, 6H, J=6.8Hz)<br>1.61(t, 1H, J=6.6Hz)<br>1.87(dd, 1H, J=6.6Hz & 10.6Hz)<br>2.64(quartett, 4H, J=6.8Hz)<br>2.87(t, 2H, J=6.6Hz)<br>3.03(dd, 1H, J=6.6Hz & 10.6Hz)<br>4.31(t, 2H, J=6.6Hz)<br>6.95–7.48(m, 8H)<br>7.83(dd, 1H, J=1.6Hz & 7.9Hz) | citrate<br>C H N<br>Calc.: 61.98 6.32 5.16<br>Found: 61.82 6.41 5.10 |
| 27 | structure with N(CH₃)₂ ethyl oxime, dimethoxy chromane, phenyl | 156–157 citrate | 2950 2810<br>1615 1600<br>1500 1460<br>1450 1420<br>1255 1210<br>1080 1035<br>970 860<br>800 755<br>690 | 1.07(t, 6H, J=7.3Hz)<br>1.55(t, 1H, J=6.6Hz)<br>1.85(dd, 1H, J=6.6Hz & 10.6Hz)<br>2.66(quartett, 4H, J=7.3Hz)<br>2.88(t, 2H, J=6.2Hz)<br>2.98(dd, 1H, J=6.6Hz & 10.6Hz)<br>3.86(s, 3H), 3.89(s, 3H)<br>4.31(t, 2H, J=6.2Hz)6.49(s, 1H)<br>7.24–7.47(m, 6H) | citrate.½H₂O<br>C H N<br>Calc.: 58.91 6.43 4.58<br>Found: 58.86 6.28 4.57 |
| 28 | structure with morpholinoethyl oxime, chromane, phenyl | 136.5–137.5 maleate | 2960 2850<br>2800 1620<br>1600 1480<br>1455 1380<br>1310 1255<br>1235 1120<br>1110 1035<br>980 865<br>760 745<br>690 | 1.62(t, 1H, J=6.4Hz)<br>1.87(dd, 1H, J=6.4Hz & 10.9Hz)<br>2.52–2.57(m, 4H)<br>2.76(t, 2H, J=5.8Hz)<br>3.00(dd, 1H, J=6.4Hz & 10.9Hz)<br>3.66–3.70(m, 4H)<br>4.30–4.36(m, 2H)<br>6.94–7.84(m, 9H) | maleate<br>C H N<br>Calc.: 64.99 5.87 5.83<br>Found: 65.00 5.95 5.80 |

TABLE 4-continued

| | | | | | |
|---|---|---|---|---|---|
| 29 | 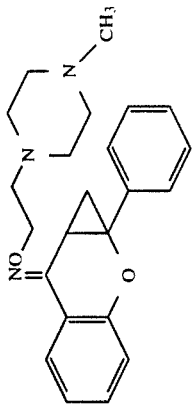 | 188–190 maleate | 2930 2790 1610 1450 1375 1342 1308 1280 1255 1230 1162 1100 1030 1010 975 760 740 690 | 1.61(t, 1H, J=6.6Hz) 1.87(dd, 1H, J=6.6Hz & 10.6Hz) 2.27(s, 3H), 2.3–2.7(m, 8H) 2.78(t, 2H, J=6.6Hz) 3.02(dd, 1H, J=6.6Hz & 10.6Hz) 4.25–4.4(m, 2H) 6.95–7.0(m, 2H)7.25–7.5(m, 6H) 7.82(dd, 1H, J=2.0Hz & 8.3Hz) | HiMS Calc.: 377.2102 Found: 377.2126 |
| 30 | 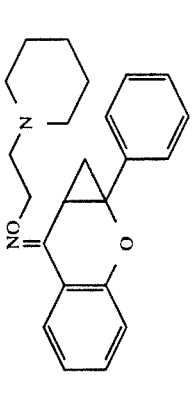 | 72–79 L-tartrate | 2920 2760 1610 1450 1380 1342 1305 1252 1228 1125 1105 1025 975 865 760 740 688 | 1.35–1.65(m, 7H) 1.87(dd, 1H, J=6.6Hz & 10.6Hz) 2.4–2.55(m, 4H) 2.73(t, 2H, J=5.9Hz) 3.03(dd, 1H, J=6.6Hz & 10.6Hz) 4.30–4.45(m, 2H) 6.95–7.00(m, 2H) 7.25–7.50(m, 6H) 7.81(dd, 1H, J=2.0Hz & 8.3Hz) | L-tartrate.1H$_2$O C H N Calc.: 61.12 6.46 5.28 Found: 60.97 6.27 5.20 |
| 31 | 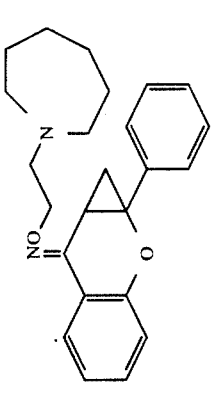 | 64–67 L-tartrate | 2910 1605 1445 1378 1305 1250 1225 1100 1105 1025 738 685 | 1.45–1.70(m, 9H) 1.87(dd, 1H, J=6.6Hz & 10.2Hz) 2.75(t, 4H, J=5.3Hz) 2.91(t, 2H, J=6.6Hz) 3.03(dd, 1H, J=6.6Hz & 10.2Hz) 4.28–4.34(m, 2H) 6.95–7.01(m, 2H)7.25–7.5(m, 6H) 7.83(dd, 1H, J=2.0Hz & 8.2Hz) | L-tartrate.1H$_2$O C H N Calc.: 61.74 6.65 5.14 Found: 61.90 6.67 5.13 |
| 32 | 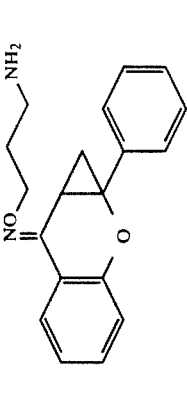 | 154–160 L-tartrate | 2920 1605 1445 1375 1305 1250 1225 1102 1025 910 860 755 740 685 | 1.62(t, 1H, J=6.6Hz) 1.8–1.95(m, 3H) 2.86(t, 2H, J=6.6Hz) 3.00(dd, 1H, J=6.6Hz & 10.6Hz) 4.2–4.35(m, 2H)6.93–7.0(m, 2H) 7.25–7.5(m, 6H). 7.83(dd, 1H) | L-tartrate.½H$_2$O C H N Calc.: 59.09 5.82 5.99 Found: 59.08 5.96 6.01 |

| | | | | |
|---|---|---|---|---|
| 33 | ![structure: chromene with N-CH3 aminopropyl cyclopropyl phenyl] | 109-112 L-tartrate | 3300 2950 2890 2810 1620 1485 1465 1390 1320 1260 1240 1115 1040 985 875 765 750 700 | 1.61(t, 1H, J=6.6Hz) 1.88(dd, 1H, J=6.6Hz & 10.5Hz) 1.92-2.02(m, 2H), 2.45(s, 3H) 2.62(br.s, 1H), 2.75(t, 2H, J=7.2Hz) 3.00(dd, 1H, J=6.6Hz & 10.5Hz) 4.27(t, 2H, J=5.9Hz) 6.94-7.85(m, 9H) | L-tartrate.½H₂O Calc.: C 60.43 H 6.02 N 5.87 Found: 60.27 5.97 5.79 |
| 34 | ![structure: 6-F chromene derivative] | 175-179 maleate | 2920 2780 1720 1610 1490 1425 1375 1315 1260 1200 1145 1110 1080 1030 995 940 875 840 805 740 690 | 1.60(t, 1H, J=6.6Hz) 1.85-2.02(m, 3H) 2.45(s, 3H) 2.73(t, 2H, J=7.3Hz) 3.00(dd, 1H, J=6.6Hz & 10.2Hz) 4.25(m, 2H) 6.65-6.75(m, 2H) 7.3-7.5(m, 5H) 7.81(t, 1H) | maleate Calc.: C 62.53 H 5.58 N 6.08 Found: 62.52 5.83 5.86 |
| 35 | ![structure: 6-Cl chromene derivative] | hygroscopic L-tartrate | 3300 2950 2850 2780 1610 1595 1480 1415 1380 1310 1225 1075 1035 980 810 750 695 | 1.59(t, 1H, J=6.6Hz) 1.90(dd, 1H, J=6.6Hz & 10.5Hz) 1.95(quintett, 2H, J=7.0Hz) 2.46(s, 3H), 2.77(t, 2H, J=7.0Hz) 2.97(dd, 1H, J=6.6Hz & 10.5Hz) 4.26(t, 2H, J=7.0Hz) 6.73-7.45(m, 7H) 7.75(d, 1H, J=8.6Hz) | L-tartrate.½H₂O Calc.: C 55.87 H 5.47 N 5.43 Found: 55.65 5.37 5.51 |
| 36 | ![structure: 6-Br chromene derivative] | hygroscopic L-tartrate | 2930 1605 1475 1410 1220 1030 980 745 | 1.59(t, 1H, J=6.6Hz) 1.85-2.1(m, 3H), 2.46(s, 3H), 2.76(t, 2H, J=7.3Hz) 2.98(dd, 1H, J=6.6Hz & 10.6Hz) 4.26(t, 2H, J=6.6Hz) 7.09(dd, 1H, J=2.0Hz & 8.2Hz) 7.16(d, 1H, J=2.0Hz) 7.29-7.5(m, 5H) 7.69(d, 1H, J=7.9Hz) | L-tartrate.2H₂O Calc.: C 49.07 H 5.32 N 4.77 Found: 49.28 5.17 4.66 |

TABLE 4-continued

| | Structure | | NMR | Salt / Analysis |
|---|---|---|---|---|
| 40 | (3,4-dimethoxyphenyl chromene cyclopropane phenyl, N-methylpropylamine oxime) | 110-115 L-tartrate | 2920 1600 1460<br>1500 1420<br>1445 1300<br>1365 1205<br>1255 1160<br>1190 1040<br>1080 860<br>985 755<br>800 690<br>720 | 1.56(t, 1H, J=6.6Hz)<br>1.87(dd, 1H, J=6.6Hz & 10.6Hz)<br>1.94(quintett, 2H, J=6.6Hz)<br>2.44(s, 3H), 2.73(t, 2H, J=6.6Hz)<br>2.96(dd, 1H, J=6.6Hz & 10.6Hz)<br>3.86(s, 3H), 3.89(s, 3H),<br>4.25(t, 2H, J=6.6Hz)<br>6.49(s, 1H)<br>7.23–7.48(m, 6H) | L-tartrate.2H₂O<br>C H N<br>Calc.: 54.92 6.38 4.93<br>Found: 55.20 6.23 5.40 |
| 41 | (chromene cyclopropane p-methoxyphenyl, N-methylpropylamine oxime) | 75-80 fumarate | 2930 2790<br>1605 1510<br>1450 1375<br>1460 1240<br>1300 1170<br>1230 1020<br>1101 880<br>970 760<br>820 | 1.56(t, 1H, J=6.6Hz)<br>1.82(dd, 1H, J=6.6Hz & 10.6Hz)<br>1.94(quintett, 2H, J=6.6Hz)<br>2.44(s, 3H)2.72(t, 2H, J=6.6Hz)<br>2.95(dd, 1H, J=6.6Hz & 10.6Hz)<br>3.82(s, 3H)<br>4.27(t, 2H, J=6.6Hz)<br>6.91–7.42(m, 7H)<br>7.81(dd, 1H, J=2.0Hz & 7.9Hz) | fumarate.H₂O<br>C H N<br>Calc.: 61.72 6.21 5.76<br>Found: 62.02 6.41 6.03 |
| 42 | (chromene cyclopropane 3,4-dichlorophenyl, N-methylpropylamine oxime) | 88-92 maleate | 3435 2955<br>2790 1615<br>1585 1480<br>1460 1385<br>1235 1030<br>865 760 | 1.64(t, 1H, J=6.6Hz)<br>1.72(br.s, 1H)<br>1.83(dd, 1H, J=6.6Hz & 10.6Hz)<br>1.96(m, 2H)2.45(s, 3H)<br>2.73(t, 2H, J=7.3Hz)<br>2.98(dd, 1H, J=6.6Hz & 10.6Hz)<br>4.27(m, 2H)6.98(m, 2H)<br>7.2(m, 2H) 7.46(d, 1H, J=8.6Hz)<br>7.57(d, 1H, J=2.6Hz)7.81(d, 1H, J=7.9Hz) | maleate.½H₂O<br>C H N<br>Calc.: 56.32 4.82 5.47<br>Found: 56.30 4.81 5.36 |
| 43 | (fluoro chromene cyclopropane p-fluorophenyl, N-methylpropylamine oxime) | 68-70 fumarate | 2940 2795<br>1622 1606<br>1516 1500<br>1429 1382<br>1262 1226<br>1151 1026<br>1000 832<br>809 762 | 1.59(t, 1H, J=6.6Hz)<br>1.84(dd, 1H, J=6.6Hz & 10.6Hz)<br>1.94(t, 2H, J=6.6Hz)2.44(s, 3H)<br>2.72(t, 2H, J=6.6Hz)<br>2.96(dd, 1H, J=6.6Hz & 10.6Hz)<br>4.26(t, 2H, J=6.6Hz)<br>6.63–7.84(m, 7H) | fumarate.H₂O<br>C H N<br>Calc.: 58.53 5.32 5.69<br>Found: 58.97 4.91 5.68 |

TABLE 4-continued

| | | | | | |
|---|---|---|---|---|---|
| 44 | 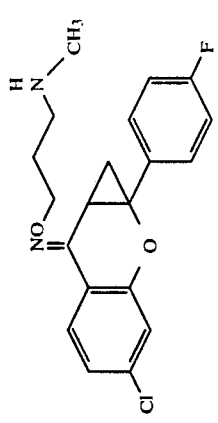 | 161-163 fumarate | 3435 2960 2775 1680 1615 1515 1415 1225 985 830 | 1.49(broad, 1H) 1.57(t, 1H, J=6.6Hz) 1.84(dd, 1H, J=6.6Hz & 10.6Hz) 1.94(m, 2H)2.44(s, 3H) 2.71(t, 2H, J=6.6Hz) 2.95(dd, 1H, J=6.6Hz & 10.6Hz) 4.27(m, 2H)6.9(m, 2H) 7.1(m, 2H)7.4(m, 2H) 7.76(d, 1H, J=7.9Hz) | fumarate.¼H₂O<br>　　　C　　H　　N<br>Calc.: 58.19 4.98 5.65<br>Found: 57.96 4.98 5.63 |
| 45 | 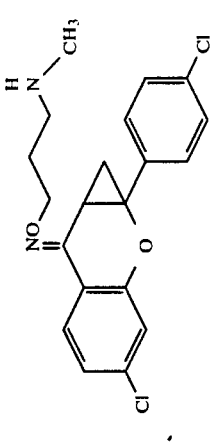 | 72-80 amorphous L-tartrate | 2930 2870 2790 1610 1597 1480 1415 1380 1308 1225 1110 1095 1070 1020 1008 982 920 890 815 750 | 1.55-1.65(m, 1H)1.8-2.0(m, 3H) 2.44(s, 3H), 2.72(t, 2H, J=6.6Hz) 2.95(dd, 1H, J=7.3Hz & 10.6Hz) 4.2-4.35(m, 2H), 6.9-7.0(m, 2H) 7.37(s, 4H), 7.76(d, 1H, J=8.6Hz) | L-tartrate.5/4H₂O<br>　　　C　　H　　N<br>Calc.: 51.12 5.09 4.97<br>Found: 51.10 4.92 4.91 |
| 46 | 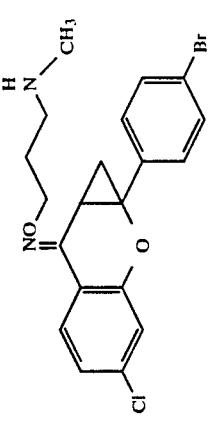 | 160-163 fumarate | fumarate 3440 2960 2780 1680 1615 1415 1230 1075 1010 985 815 | 1.49(broad, 1H) 1.59(dd, 1H, J=6.6Hz & 7.3Hz) 1.85(dd, 1H, J=7.3Hz & 10.6Hz) 1.93(m, 2H)2.44(s, 3H) 2.71(t, 2H, J=7.3Hz) 2.95(dd, 1H, J=6.6Hz & 10.6Hz) 4.26(m, 2H)6.9(m, 2H) 7.30(d, 2H, J=8.6Hz) 7.53(d, 2H, J=8.6Hz) 7.76(d, 1H, J=8.6Hz) | fumarate.¼H₂O<br>　　　C　　H　　N<br>Calc.: 51.40 4.49 5.00<br>Found: 51.38 4.38 4.99 |
| 47 | 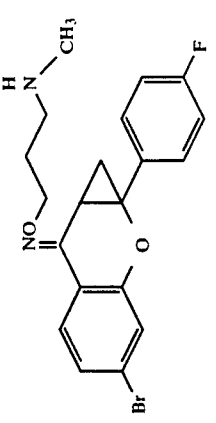 | 178-179 fumarate | fumarate 3435 2960 2780 1680 1610 1515 1410 1225 985 830 | 1.49(broad, 1H) 1.56(t, 1H, J=6.6Hz) 1.84(dd, 1H, J=6.6Hz & 10.6Hz) 1.93(m, 2H)2.44(s, 3H) 2.71(t, 2H, J=7.3Hz) 2.95(dd, 1H, J=6.6Hz & 10.6Hz) 4.26(m, 2H)7.1(m, 4H) 7.4(m, 2H)7.69(d, 1H, J=8.6Hz) | fumarate<br>　　　C　　H　　N<br>Calc.: 53.84 4.52 5.23<br>Found: 53.62 4.56 5.14 |

TABLE 4-continued

| | Structure | mp/salt | IR | NMR | Analysis |
|---|---|---|---|---|---|
| 48 | [structure: 6-Br chromene with cyclopropane, 4-Cl phenyl, N-CH₃ oxime propyl] | 168–171 fumarate | 3435 2955 2780 1675 1615 1410 1225 985 820 | 1.50(broad, 1H) 1.59(t, 1H, J=6.6Hz) 1.85(dd, 1H, J=6.6Hz & 10.6Hz) 1.93(m, 2H)2.44(s, 3H) 2.71(t, 2H, J=7.3Hz) 2.95(dd, 1H, J=6.6Hz & 10.6Hz) 4.26(m, 2H)7.1(m, 2H) 7.36(s, 4H)7.69(d, 1H, J=7.9Hz) | fumarate.½H₂O<br>C H N<br>Calc.: 51.82 4.44 5.04<br>Found: 51.81 4.37 4.96 |
| 49 | [structure: 6-Br chromene with cyclopropane, 4-Br phenyl, N-CH₃ oxime propyl] | 168–170 fumarate | 3435 2960 2780 1675 1610 1415 1225 1070 1010 985 815 | 1.46(broad, 1H) 1.59(t, 1H, J=6.6Hz) 1.84(dd, 1H, J=7.3Hz & 10.6Hz) 1.93(m, 2H)2.44(s, 3H) 2.71(t, 2H, J=7.3Hz) 2.95(dd, 1H, J=6.6Hz & 10.6Hz) 4.26(m, 2H)7.1(m, 2H) 6.6(m, 2H)7.52(d, 2H, J=8.6Hz) 7.69(d, 1H, J=8.6Hz) | fumarate<br>C H N<br>Calc.: 48.34 4.06 4.70<br>Found: 48.41 4.10 4.66 |
| 50 | [structure: chromene with cyclopropane, phenyl, N-CH₂CH₃ oxime butyl] | 134.5–136 maleate | 2920 1602 1442 1370 1335 1302 1245 1220 1120 1020 970 860 750 735 682 | 1.09(t, 3H, J=7.3Hz) 1.62(t, 1H, J=6.6Hz) 1.84–2.0(m, 3H)2.6–2.7(m, 2H) 2.76(t, 2H, J=6.6Hz) 3.01(dd, 1H, J=6.6Hz & 10.6Hz) 4.2–4.35(m, 2H) 6.9–7.0(m, 2H) 7.25–7.5(m, 6H) 7.82(dd, 1H, J=2.0Hz & 8.3Hz) | maleate<br>C H N<br>Calc.: 66.36 6.24 6.19<br>Found: 66.17 6.26 6.06 |
| 51 | [structure: 6-F chromene with cyclopropane, phenyl, N-CH₃ oxime propyl] | 155–157 maleate | 2920 2790 1605 1485 1420 1370 1310 1250 1220 1140 1110 1080 1030 990 950 870 840 800 740 685 | 1.11(t, 3H, J=7.3Hz) 1.59(t, 1H, J=7.3Hz) 1.85–2.05(m, 3H) 2.68(q, 2H, J=7.3Hz) 2.78(t, 2H, J=7.3Hz) 2.99(dd, 1H, J=7.3Hz & 10.6Hz) 4.24(t, 2H) 6.65–6.75(m, 2H) 7.25–7.5(m, 5H) 7.8–7.85(m, 1H) | maleate<br>C H N<br>Calc.: 63.82 5.78 5.95<br>Found: 63.74 5.72 5.85 |

TABLE 4-continued

| | Structure | mp (°C) / salt | IR | NMR | Analysis |
|---|---|---|---|---|---|
| 52 | 4-Cl phenyl, cyclopropane-O, =NO-(CH$_2$)$_3$-NH-CH$_2$CH$_3$ | 145–147 maleate | 2910 2850; 2800 1600; 1550 1470; 1440 1405; 1370 1325; 1300 1260; 1215 1110; 1065 1025; 1010 980; 920 850; 800 740; 685 | 1.10(t, 3H, J=7.3Hz); 1.59(t, 1H, J=6.6Hz); 1.85–2.05(m, 3H); 2.67(q, 2H, J=7.3Hz); 2.77(t, 2H, J=7.3Hz); 2.98(dd, 1H, J=6.6Hz & 10.2Hz); 4.2–4.3(m, 2H); 6.9–7.0(m, 2H); 7.3–7.5(m, 5H); 7.76(d, 1H, J=7.9Hz) | maleate<br>Calc.: C 61.66 H 5.59 N 5.75<br>Found: 61.68 5.68 5.71 |
| 53 | 4-Br phenyl, cyclopropane-O, =NO-(CH$_2$)$_3$-NH-CH$_2$CH$_3$ | 138–139 maleate | 2910 2860; 2800 1600; 1585 1545; 1470 1440; 1400 1370; 1320 1300; 1260 1215; 1120 1025; 975 905; 800 740; 685 | 1.11(t, 3H, J=7.3Hz); 1.59(t, 1H, J=6.6Hz); 1.85–2.0(m, 3H); 2.67(q, 2H, J=7.3Hz); 2.77(t, 2H, J=6.6Hz); 2.98(dd, 1H, J=6.6Hz & 10.6Hz); 4.26(t, 2H); 7.10(dd, 1H, J=2.0Hz & 8.6Hz); 7.16(d, 1H, J=2.0Hz); 7.25–7.5(m, 4H); 7.69(d, 1H, J=8.6Hz) | maleate<br>Calc.: C 56.51 H 5.12 N 5.27<br>Found: 56.46 5.15 5.13 |
| 54 | 5-Cl phenyl, cyclopropane-O, =NO-(CH$_2$)$_3$-NH-CH$_2$CH$_3$ | 97–98 maleate | 2920 2860; 2800 1610; 1595 1465; 1450 1425; 1370 1285; 1245 1220; 1105 1030; 1015 975; 910 880; 810 755; 740 690 | 1.11(t, 3H, J=7.3Hz); 1.59(t, 1H, J=6.6Hz); 1.85–2.05(m, 3H); 2.67(q, 2H, J=7.3Hz); 2.76(t, 2H, J=6.6Hz); 2.97(dd, 1H, J=6.6Hz & 10.6Hz); 4.28(t, 2H); 6.91(d, 1H, J=9.2Hz); 7.2–7.55(m, 6H); 7.80(d, 1H, J=2.6Hz) | maleate<br>Calc.: C 59.46 H 5.79 N 5.55<br>Found: 59.63 5.53 5.53 |
| 55 | 4,5-diCl phenyl, cyclopropane-O, =NO-(CH$_2$)$_3$-NH-CH$_2$CH$_3$ | 137–140 fumarate | 3435 2945; 2790 1690; 1615 1405; 1285 1240; 1130 985; 760 745; 700 | 1.10(t, 3H, J=7.3Hz)1.52(br, 1H); 1.57(t, 1H, J=6.6Hz)1.9(m, 3H); 2.66(q, 2H, J=7.3Hz); 2.76(t, 2H, J=7.3Hz); 2.96(dd, 1H, J=6.6Hz & 10.6Hz); 4.27(m, 2H)7.10(s, 1H); 7.4(m, 5H)7.91(s, 1H) | fumarate·½H$_2$O<br>Calc.: C 57.10 H 5.08 N 5.33<br>Found: 57.08 5.06 5.05 |

TABLE 4-continued
| | | | | |
|---|---|---|---|---|
| 56 | 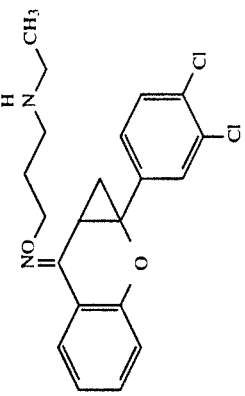 | 61-66 maleate | 3435 2950<br>2790 1690<br>1585 1500<br>1460 1385<br>1200 1050<br>1030 865<br>755 715 | 1.10(t, 3H, J=7.3Hz)1.47(br, 1H)<br>1.65(t, 1H, J=7.3Hz)<br>1.83(dd, 1H, J=7.3Hz & 10.6Hz)<br>1.95(m, 2H)2.66(q, 2H, J=7.3Hz)<br>2.76(t, 2H, J=7.3Hz)<br>2.98(dd, 1H, J=7.3Hz & 10.6Hz)<br>4.28(m, 2H)6.99(m, 2H)<br>7.2(m, 2H)7.46(d, 1H, J=7.9Hz)<br>7.56(d, 1H, J=2.0Hz)7.81(d, 1H, J=7.9Hz) | maleate.¼H₂O<br>C H N<br>Calc.: 57.10 5.08 5.33<br>Found: 56.95 5.08 5.18 |

| | | | | |
|---|---|---|---|---|
| 57 | 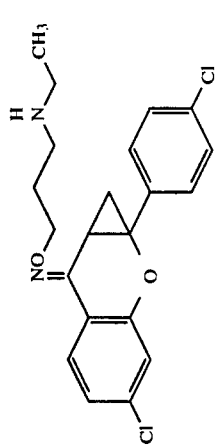 | 172-173.5 maleate | 2920 2860<br>2800 1605<br>1595 1555<br>1475 1405<br>1375 1330<br>1300 1260<br>1220 1105<br>1085 1040<br>1005 980<br>920 885<br>850 805<br>750 720 | 1.13(t, 3H, J=7.3Hz)<br>1.59(t, 1H, J=6.6Hz)<br>1.86(dd, 1H, J=6.6Hz & 10.6Hz)<br>1.99(t, 2H, J=5.9Hz)<br>2.70(q, 2H, J=7.3Hz)<br>2.79(t, 2H, J=5.9Hz)<br>2.95(dd, 1H, J=6.6Hz & 10.6Hz)<br>4.27(t, 2H, J=5.9Hz)<br>6.9-7.0(m, 2H)<br>7.26(s, 4H)<br>7.37(s, 4H)<br>7.76(d, 1H, J=8.6Hz) | maleate.¼H$_2$O<br>C H N<br>Calc.: 57.10 5.08 5.33<br>Found: 57.27 5.11 5.29 |
| 58 | 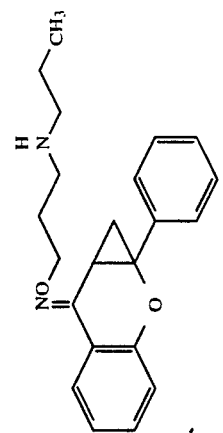 | oil | 2920 1605<br>1445 1375<br>1340 1305<br>1250 1222<br>1120 1102<br>1012 975<br>865 755<br>740 685 | 0.89(t, 3H, J=7.3Hz)1.4-1.6(m, 2H)<br>1.62(t, 1H, J=6.6Hz)<br>1.84-2.0(m, 3H)<br>2.57(t, 2H, J=7.3Hz)<br>2.75(t, 2H, J=7.3Hz)<br>3.01(dd, 1H, J=6.6Hz & 10.6Hz)<br>4.15-4.3(m, 2H)6.9-7.0(m, 2H)<br>7.25-7.5(m, 6H),<br>7.82(dd, 1H, J=1.3Hz & 1.9Hz) | maleate.¼H$_2$O<br>(oil) C H N<br>Calc.: 66.30 6.93 5.95<br>Found: 66.35 6.64 5.94 |
| 59 | 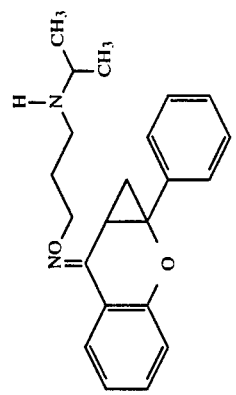 | 123.5-124.5 maleate | 2940 1615<br>1455 1380<br>1340 1310<br>1255 1230<br>1170 1130<br>1105 1030<br>980 865<br>760 742<br>695 | 1.05(d, 6H, J=5.9Hz)<br>1.61(t, 1H, J=6.6Hz)<br>1.84-2.0(m, 3H)2.7-2.85(m, 3H)<br>3.00(dd, 1H, J=6.6Hz & 10.7Hz)<br>4.2-4.35(m, 2H)<br>6.9-7.0(m, 2H)<br>7.25-7.50(m, 6H)<br>7.82(dd, 1H, J=2.0Hz & 7.9Hz) | maleate<br>C H N<br>Calc.: 66.93 6.48 6.01<br>Found: 66.84 6.51 5.87 |
| 60 | 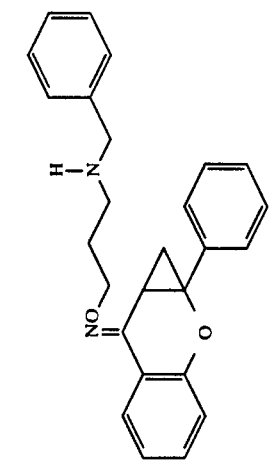 | 73-80 L-tartrate | 3050 3020<br>2860 2810<br>1610 1480<br>1450 1380<br>1340 1308<br>1255 1228<br>1122 1108<br>1025 978<br>875 798<br>760 740<br>692 | 1.57(t, 1H, J=6.6Hz)<br>1.81(dd, 1H, J=6.6Hz & 10.6Hz)<br>1.95-2.05(m, 2H),<br>2.79(t, 2H, J=6.6Hz)<br>2.96(dd, 1H, J=6.6Hz & 10.6Hz)<br>3.79(s, 2H)4.28(t, 2H, J=6.6Hz)<br>6.93-7.0(m, 2H),<br>7.17-7.46(m, 1H)<br>7.81(dd, 1H, J=2.0Hz & 7.9Hz) | L-tartrate.2H$_2$O<br>C H N<br>Calc.: 61.63 6.21 4.79<br>Found: 61.57 6.03 4.66 |

| | | | | |
|---|---|---|---|---|
| 61 | 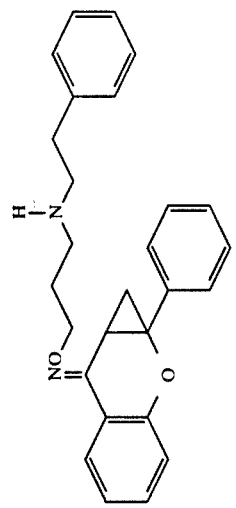 | 60-75<br>L-tartrate | 3020 2920<br>1610 1450<br>1378 1340<br>1308 1250<br>1225 1120<br>1102 1025<br>975 740<br>690 | 1.5-1.7(m, 1H)<br>1.87(dd, 1H, J=6.6Hz & 10.6Hz)<br>1.8-2.0(m, 2H)2.75-2.85(s, 4H)<br>2.85-2.93(m, 2H)<br>2.99(dd, 1H, J=6.6Hz & 10.6Hz)<br>4.22-4.28(m, 2H)<br>6.94-7.00(m, 2H)<br>7.15-7.5(m, 11H)<br>7.81(dd, 1H, J=2.0Hz & 7.9Hz) | L-tartrate.9/4H₂O<br>C H N<br>Calc.: 62.48 5.94 4.55<br>Found: 62.45 6.23 4.62 |
| 62 | 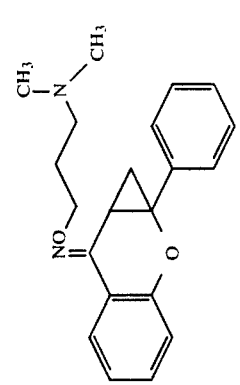 | 138.5-139.0<br>maleate | 2940 2820<br>2760 1615<br>1600 1455<br>1380 1360<br>1315 1255<br>1235 1055<br>1040 975<br>900 885<br>870 760<br>740 690 | 1.62(t, 1H, J=6.6Hz)<br>1.86-2.00(m, 3H), 2.25(s, 6H)<br>2.49(t, 2H, J=7.9Hz)<br>3.01(dd, 1H, J=6.6Hz & 10.6Hz)<br>4.24(t, 2H, J=6.3Hz)<br>6.95-7.84(m, 9H) | maleate<br>C H N<br>Calc.: 66.36 6.24 6.19<br>Found: 65.71 6.24 6.13 |
| 63 | 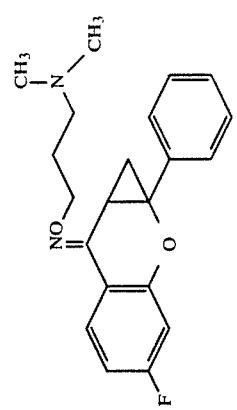 | 156-158<br>maleate | 2940 1620<br>1605 1500<br>1430 1380<br>1260 1210<br>1148 998<br>850 | 1.60(t, 1H, J=6.6Hz)<br>1.85-2.0(m, 3H), 2.25(s, 6H)<br>2.41(t, 2H, J=7.3Hz)<br>3.01(dd, 1H, J=6.6Hz & 10.6Hz)<br>4.15-4.3(m, 2H)<br>6.65-6.75(m, 5H)<br>7.3-7.5(m, 5H)<br>7.78-7.85(m, 1H) | maleate<br>C H N<br>Calc.: 63.82 5.98 5.95<br>Found: 63.70 5.91 5.91 |
| 64 | 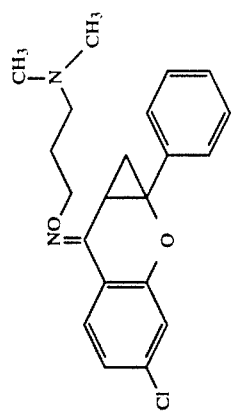 | 162-164<br>maleate | 3050 2940<br>2860 2810<br>2760 1610<br>1590 1555<br>1410 1220<br>980 740<br>690 | 1.59(t, 1H, J=6.6Hz)<br>1.86-2.03(m, 3H), 2.31(s, 6H)<br>2.50(t, 1H, J=6.9Hz)<br>2.98(dd, 1H, J=6.6Hz & 10.6Hz)<br>4.24(t, 2H, J=6.3Hz)<br>6.95(dd, 1H, J=2.0Hz & 8.2Hz)<br>6.99(d, 1H, J=2.0Hz)<br>7.28-7.48(m, 5H)<br>7.75(d, 1H, J=8.2Hz) | maleate<br>C H N<br>Calc.: 61.66 5.59 5.75<br>Found: 61.54 5.72 5.62 |

| No. | Structure | mp/form | IR | NMR | Analysis |
|---|---|---|---|---|---|
| 65 | 4-Br-phenyl chromene oxime with O-(CH₂)₃-N(CH₃)₂ | 165-166.5 maleate | 2950 1615, 1598 1480, 1470 1455, 1418 1380, 1310 1220, 1205 1115, 1060 1035, 1020 980, 920 860, 720 662 | 1.59(t, 1H, J=6.6Hz), 1.85-2.0(m, 3H), 2.25(s, 6H)2.35-2.45(m, 2H), 2.99(dd, 1H, J=6.6Hz & 10.9Hz), 4.15-4.3(m, 2H), 7.08(dd, 1H)7.10-7.11(m, 1H), 7.25-7.5(m, 5H), 7.69(d, 1H, J=8.6Hz) | maleate C H N Calc.: 56.50 5.12 5.27 Found: 55.88 5.10 5.15 |
| 66 | 6-H₃CO-phenyl chromene oxime with O-(CH₂)₃-N(CH₃)₂ | oil | 2930 2850, 2800 2750, 1610 1560, 1495 1420, 1380 1340, 1260 1230, 1195 1160, 1085 1030, 960 830, 745 690 | 1.59(t, 1H, J=6.6Hz), 1.83-1.99(m, 3H), 2.22(s, 6H), 2.38-2.44(m, 2H), 2.99(dd, 1H, J=6.6Hz & 10.6Hz), 3.77(s, 3H), 4.18-4.24(m, 2H), 6.47(d, 1H, J=2.6Hz), 6.56(dd, 1H, J=2.6Hz & 8.6Hz), 7.28-7.48(m, 5H), 7.74(d, 1H, J=8.6Hz) | MS 366(M⁺) |
| 67 | benzyloxy-phenyl chromene oxime with O-(CH₂)₃-N(CH₃)₂ | oil | 2940 2860, 2810 2770, 1615 1500, 1490 1430, 1380 1260, 1235 1165, 1085 1035, 955 825, 745 690 | 1.58(t, 1H, J=6.3Hz), 1.83-1.96(m, 3H), 2.25(s, 6H), 2.40(t, 2H, J=7.9Hz), 2.97(dd, 1H, J=6.3Hz & 10.5Hz), 4.20(m, 2H)5.03(s, 2H), 6.54-7.76(m, 13H) | MS 442(M⁺) |
| 68 | 6-Cl-phenyl chromene oxime with O-(CH₂)₃-N(CH₃)₂ | 157-158.5 maleate | 2940 2810, 2760 1615, 1470 1450, 1428 1370, 1290 1250, 1225 1110, 1035 975, 810 755 | 1.58(t, 1H, J=6.6Hz), 1.85-2.00(m, 3H)2.24(s, 6H), 2.40(t, 2H, J=7.3Hz), 4.2-4.3(m, 2H), 6.91(d, 1H, J=8.6Hz), 7.22(dd, 1H, J=2.6Hz & 8.6Hz), 7.3-7.5(m, 5H), 7.80(d, 1H, J=2.6Hz) | maleate C H N Calc.: 61.66 5.59 5.75 Found: 61.47 5.59 5.72 |

| | Structure | | | | |
|---|---|---|---|---|---|
| 69 | 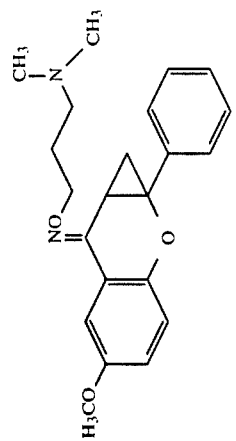 | 147–150 maleate | 2940 2860 2810 2760 1600 1485 1455 1435 1375 1300 1215 1040 980 860 820 750 720 695 | 1.57(t, 1H, J=6.6Hz) 1.84(dd, 1H, J=6.6Hz & 10.6Hz) 1.93(quintett, 2H, J=7.0Hz) 2.24(s, 6H), 2.41(t, 2H, J=7.0Hz) 2.99(dd, 1H, J=6.6Hz & 10.6Hz) 3.78(s, 3H), 4.24(t, 2H, J=7.0Hz) 6.89–7.47(m, 8H) | maleate Calc.: C 62.64 H 6.07 N 5.62 Found: 62.78 6.18 5.59 |
| 70 | 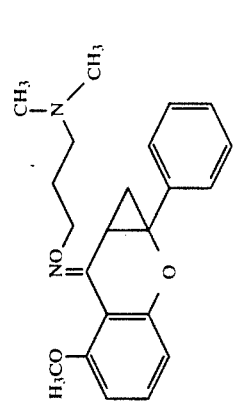 | 147–148 citrate | 2920 2800 2750 1600 1460 1375 1330 1270 1240 1090 1030 870 780 740 720 690 | 1.67(t, 1H, J=6.6Hz) 1.76(dd, 1H, J=6.6Hz & 9.9Hz) 1.90–2.00(m, 2H) 2.25(s, 6H) 2.41–2.47(m, 2H) 3.27(dd, 1H, J=6.6Hz & 9.9Hz) 3.87(s, 3H) 4.20–4.30(m, 2H) 6.60–6.65(m, 2H) 7.18–7.48(m, 6H) | citrate.½H₂O Calc.: C 58.78 H 6.25 N 4.90 Found: 58.53 6.28 5.33 |
| 71 | 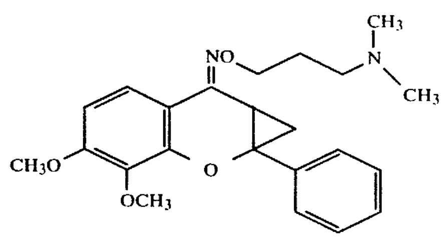 | 85–90 citrate | 2940 1600 1500 1450 1420 1380 1345 1285 1225 1095 1030 960 795 750 720 690 | 1.62(t, 1H, J=6.6Hz) 1.8–2.0(m, 3H) 2.25(s, 6H) 2.25–2.45(m, 2H) 3.02(dd, 1H, J=6.6Hz & 10.6Hz) 3.88(s, 6H) 4.15–4.3(m, 2H) 6.60(d, 1H, J=9.2Hz) 7.25–7.6(m, 6H) | citrate.2H₂O Calc.: C 58.28 H 6.24 N 4.69 Found: 58.50 6.20 4.68 |
| 72 | 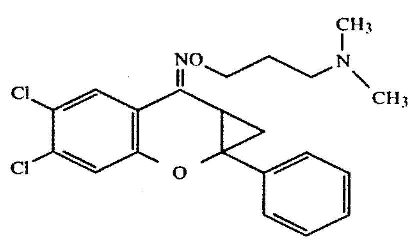 | 181–184 maleate | 2940 1615 1462 1402 1280 1235 1122 1040 985 | 1.5–1.65(m, 1H) 1.85–2.0(m, 3H) 2.27(s, 6H) 2.97(dd, 1H, J=6.6Hz & 10.6Hz) 2.40(t, 2H, J=7.3Hz) 4.24(t, 2H)7.10(s, 1H) 7.3–7.45(m, 5H) 7.91(s, 1H) | maleate Calc.: C 57.59 H 5.03 N 5.37 Found: 57.49 5.08 5.34 |

| | | -continued | | | |
|---|---|---|---|---|---|
| 73 | 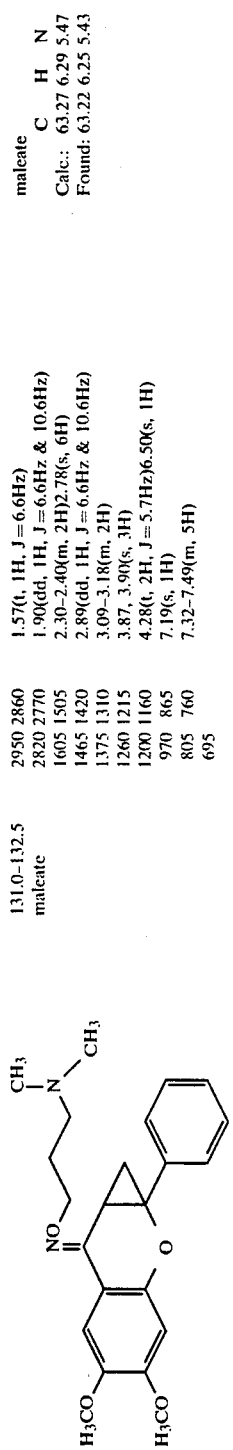 | 131.0–132.5 maleate | 2950 2860 2820 2770 1605 1505 1465 1420 1375 1310 1260 1215 1200 1160 970 865 805 760 695 | 1.57(t, 1H, J=6.6Hz) 1.90(dd, 1H, J=6.6Hz & 10.6Hz) 2.30–2.40(m, 2H)2.78(s, 6H) 2.89(dd, 1H, J=6.6Hz & 10.6Hz) 3.09–3.18(m, 2H) 3.87, 3.90(s, 3H) 4.28(t, 2H, J=5.7Hz)6.50(s, 1H) 7.19(s, 1H) 7.32–7.49(m, 5H) | maleate C H N Calc.: 63.27 6.29 5.47 Found: 63.22 6.25 5.43 |
| 74 | 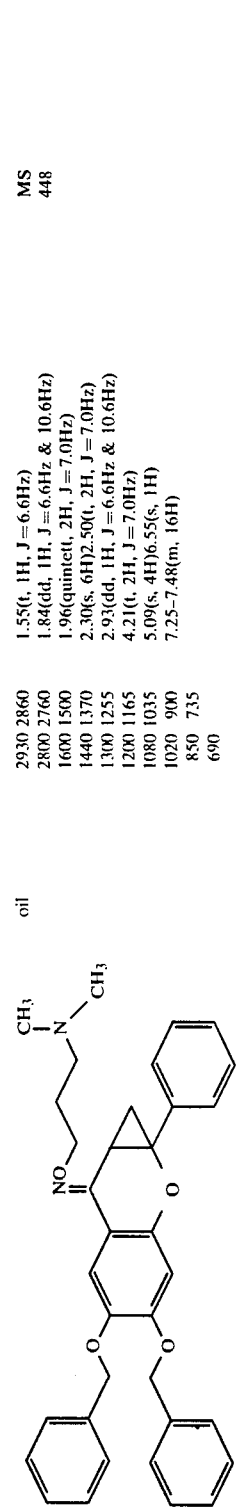 | oil | 2930 2860 2800 2760 1600 1500 1440 1370 1300 1255 1200 1165 1080 1035 1020 900 850 810 690 | 1.55(t, 1H, J=6.6Hz) 1.84(dd, 1H, J=6.6Hz & 10.6Hz) 1.96(quintett, 2H, J=7.0Hz) 2.30(s, 6H)2.50(t, 2H, J=6.6Hz) 2.93(dd, 1H, J=6.6Hz & 10.6Hz) 4.21(t, 2H, J=7.0Hz) 5.09(s, 4H)6.55(s, 1H) 7.25–7.48(m, 16H) | MS 448 |
| 75 | 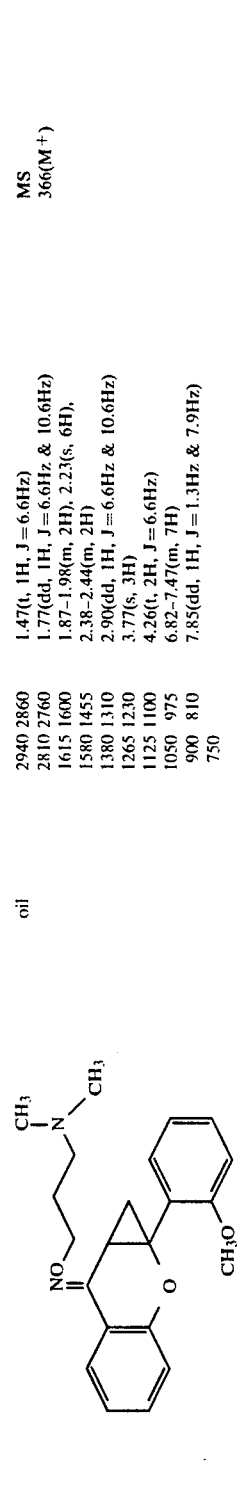 | oil | 2940 2860 2810 2760 1615 1600 1580 1455 1380 1310 1265 1230 1125 1100 1050 975 900 810 750 | 1.47(t, 1H, J=6.6Hz) 1.77(dd, 1H, J=6.6Hz & 10.6Hz) 1.87–1.98(m, 2H) 2.23(s, 6H), 2.38–2.44(m, 2H) 2.90(dd, 1H, J=6.6Hz & 10.6Hz) 3.77(s, 3H) 4.26(t, 2H, J=6.6Hz) 6.82–7.47(m, 7H) 7.85(dd, 1H, J=1.3Hz & 7.9Hz) | MS 366(M+) |
| 76 | 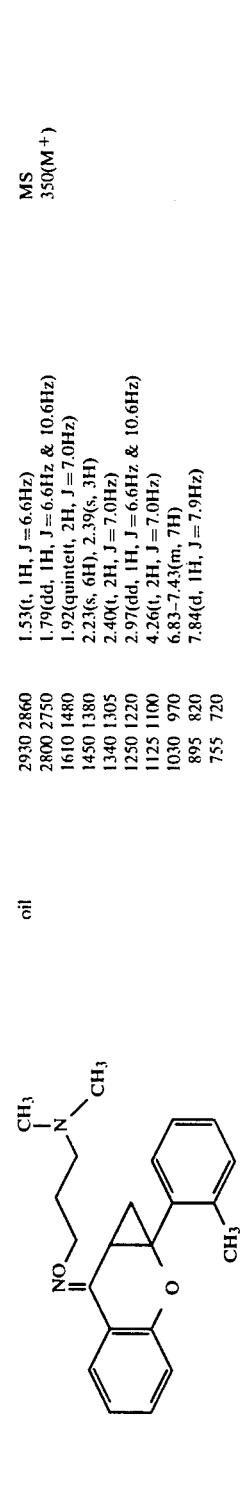 | oil | 2930 2860 2800 2750 1610 1480 1450 1380 1340 1305 1250 1220 1125 1100 1030 970 895 820 755 720 | 1.53(t, 1H, J=6.6Hz) 1.79(dd, 1H, J=6.6Hz & 10.6Hz) 1.92(quintett, 2H, J=7.0Hz) 2.23(s, 6H), 2.39(s, 3H) 2.40(t, 2H, J=7.0Hz) 2.97(dd, 1H, J=6.6Hz & 10.6Hz) 4.26(t, 2H, J=7.0Hz) 6.83–7.43(m, 7H) 7.84(d, 1H, J=7.9Hz) | MS 350(M+) |

| | | | | |
|---|---|---|---|---|
| 77 | [structure: chromene with N-oxime, N(CH3)2 propyl chain, cyclopropane linked to 3-chlorophenyl] | oil | 2940 2850<br>2800 2750<br>1615 1595<br>1480 1455<br>1375 1305<br>1250 1230<br>1035 975<br>820 780<br>760 680 | 1.66(t, 1H, J=6.6Hz)<br>1.81–2.01(m, 3H)2.26(s, 6H)<br>2.44(t, 2H, J=7.6Hz)<br>3.00(dd, 1H, J=6.6Hz & 10.5Hz)<br>4.24(t, 2H, J=6.6Hz)<br>6.96–7.48(m, 7H)<br>7.81(dd, 1H, J=2.0Hz & 7.1Hz) | MS<br>370(M$^+$) |
| 78 | [structure: chromene with N-oxime, N(CH3)2 propyl chain, cyclopropane linked to 3-methoxyphenyl] | oil | 2930 2860<br>2810 2760<br>1615 1600<br>1580 1450<br>1375 1310<br>1290 1255<br>1230 1185<br>980 845<br>760 690 | 1.61(t, 1H, J=6.6Hz)<br>1.87(dd, 1H, J=6.6Hz & 10.6Hz)<br>1.94(quintett, 2H, J=6.6Hz)<br>2.26(s, 6H),<br>2.44(t, 2H, J=6.6Hz)<br>3.01(dd, 1H, J=6.6Hz & 10.6Hz)<br>3.83(s, 3H), 4.24(t, 2H, J=6.6Hz)<br>6.84–7.34(m, 7H)<br>7.82(dd, 1H, J=1.3Hz & 6.6Hz) | MS<br>366(M$^+$) |
| 79 | [structure: chromene with N-oxime, N(CH3)2 propyl chain, cyclopropane linked to 3-methylphenyl] | oil | 2940 2860<br>2800 2750<br>1615 1455<br>1380 1340<br>1310 1255<br>1230 1185<br>1090 1040<br>975 850<br>780 760<br>690 | 1.59(t, 1H, J=6.6Hz)<br>1.83–1.99(m, 3H), 2.25(s, 6H)<br>2.38(s, 3H),<br>2.43(t, 2H, J=7.3Hz)<br>3.00(dd, 1H, J=6.6Hz & 10.6Hz)<br>4.24(t, 2H, J=6.5Hz)<br>6.93–7.31(m, 7H)<br>7.82(dd, 1H, J=2.0Hz & 7.9Hz) | MS<br>350(M$^+$) |
| 80 | [structure: chromene with N-oxime, N(CH3)2 propyl chain, cyclopropane linked to 4-chlorophenyl] | 87.5–88.5<br>maleate | 2930 2850<br>2750 1610<br>1600 1490<br>1450 1380<br>1305 1250<br>1225 1100<br>1085 1030<br>1000 975<br>880 815<br>760 | 1.62(t, 1H, J=7.2Hz)<br>1.84(dd, 1H, J=7.2Hz & 10.6Hz)<br>1.97(quintett, 2H, J=7.0Hz)<br>2.30(s, 6H),<br>2.49(t, 2H, J=7.0Hz)<br>2.98(dd, 1H, J=7.2Hz & 10.6Hz)<br>4.24(t, 2H, J=7.0Hz)<br>6.94–7.38(m, 7H)<br>7.82(dd, 1H, J=2.0Hz & 7.9Hz) | maleate.1H$_2$O<br>   C    H    N<br>Calc.: 59.46 5.79 5.55<br>Found: 59.31 5.54 5.55 |

| | | -continued | | | |
|---|---|---|---|---|---|
| 81 | 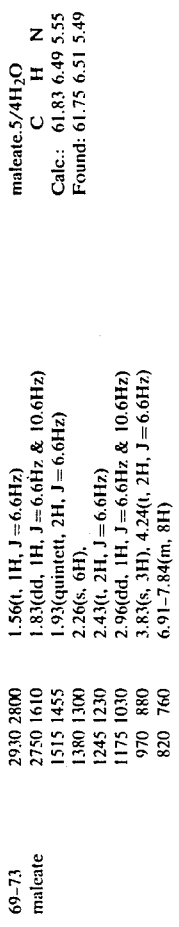 | 69–73 maleate | 2930 2800<br>2750 1610<br>1515 1455<br>1380 1300<br>1245 1230<br>1175 1030<br>970 880<br>820 760 | 1.56(t, 1H, J=6.6Hz)<br>1.83(dd, 1H, J=6.6Hz & 10.6Hz)<br>1.93(quintett, 2H, J=6.6Hz)<br>2.26(s, 6H),<br>2.43(t, 2H, J=6.6Hz)<br>2.96(dd, 1H, J=6.6Hz & 10.6Hz)<br>3.83(s, 3H), 4.24(t, 2H, J=6.6Hz)<br>6.91–7.84(m, 8H) | maleate.5/4H₂O<br>    C    H    N<br>Calc.: 61.83 6.49 5.55<br>Found: 61.75 6.51 5.49 |
| 82 | | 84.5–85.5 maleate | 2930 2850<br>2800 2750<br>1610 1600<br>1480 1455<br>1380 1360<br>1310 1250<br>1230 1100<br>1035 970<br>885 805<br>760 740 | 1.58(t, 1H, J=6.6Hz)<br>1.84(dd, 1H, J=6.6Hz & 10.6Hz)<br>1.92(quintett, 2H, J=7.0Hz)<br>2.24(s, 6H), 2.36(s, 3H)<br>2.41(t, 2H, J=7.0Hz)<br>2.98 (dd, 1H, J=6.6Hz & 10.6Hz)<br>4.23(t, 2H, J=7.0Hz)<br>6.93–7.34(m, 7H)<br>7.82(dd, 1H, J=1.6Hz & 8.4Hz) | maleate.1H₂O<br>    C    H    N<br>Calc.: 64.44 6.66 5.78<br>Found: 64.33 6.57 5.74 |
| 83 | | oil | 2940 2860<br>2810 2760<br>1620 1460<br>1325 1255<br>1235 1170<br>1120 1070<br>890 830<br>760 740<br>685 | 1.70(t, 1H, J=6.6Hz)<br>1.87–1.98(m, 3H), 2.27(s, 6H)<br>2.45(t, 2H, J=7.3Hz)<br>3.05(dd, 1H, J=6.6Hz & 10.6Hz)<br>4.26(t, 2H, J=6.6Hz)<br>6.97–7.85(m, 8H) | MS<br>404(M⁺) |
| 84 | | oil | 2930 1720<br>1610 1450<br>1430 1370<br>1305 1280<br>1250 1225<br>1180 1105<br>1050 975<br>900 840<br>760 740 | 1.69(t, 1H, J=6.6Hz)<br>1.93(dd, 1H, J=6.6Hz & 10.5Hz)<br>2.04–2.18(m, 2H)<br>2.53(s, 6H),<br>2.81(t, 2H, J=8.1Hz)<br>3.04(dd, 1H, J=6.6Hz & 10.5Hz)<br>3.92(s, 3H), 4.26(t, 2H, J=6.6Hz & 5.9Hz)<br>6.96–8.08(m, 8H) | MS<br>394(M⁺) |

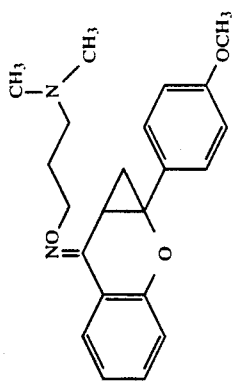

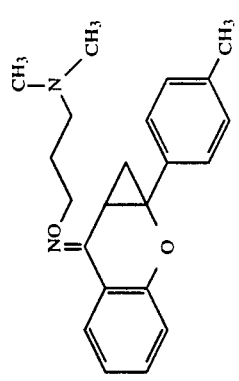

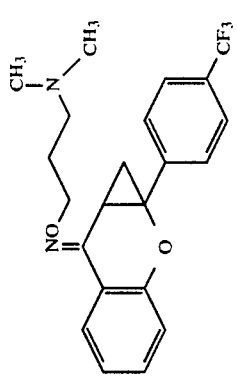

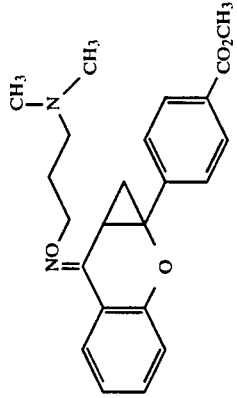

| | | | | |
|---|---|---|---|---|
| 85 | 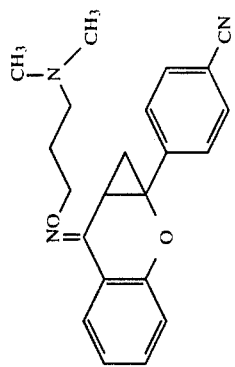 | 103-107 maleate | 1685 1570<br>1470 1355<br>1290 1245<br>1200 1045<br>865 740 | 1.73(t, 1H, J=6.6Hz)<br>1.85-2.0(m, 3H), 2.26(s, 6H)<br>2.42(t, 2H, J=7.3Hz)<br>3.06(dd, 1H, J=6.6Hz & 10.6Hz)<br>4.2-4.3(m, 2H)<br>6.95-7.05(m, 2H)<br>7.3-7.4(m, 1H)<br>7.54(d, 2H, J=8.6Hz)<br>7.69(d, 2H, J=8.6Hz)<br>7.8-7.9(m, 1H) | maleate.½H₂O<br>    C   H   N<br>Calc.: 64.18 5.59 8.64<br>Found: 63.94 5.66 8.62 |
| 86 | 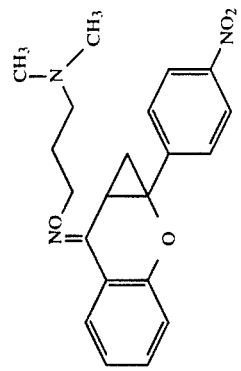 | 176-179 maleate | 3070 2950<br>2860 2820<br>2770 1605<br>1520 1460<br>1350 1260<br>1235 1105<br>1040 875<br>860 765<br>745 | 1.77(dd, 1H, J=6.6Hz & 7.3Hz)<br>1.94(m, 3H), 2.24(s, 6H)<br>2.40(t, 2H)<br>3.11(dd, 1H, J=6.6Hz & 10.6Hz)<br>4.25(m, 2H)7.02(m, 2H)<br>7.31(m, 1H)<br>7.59(d, 2H, J=9.2Hz)<br>7.84(dd, 1H, J=7.9Hz & 1.3Hz)<br>8.26(d, 2H, J=9.2Hz) | maleate<br>    C   H   N<br>Calc.: 60.36 5.47 8.45<br>Found: 60.28 5.60 8.28 |
| 87 | 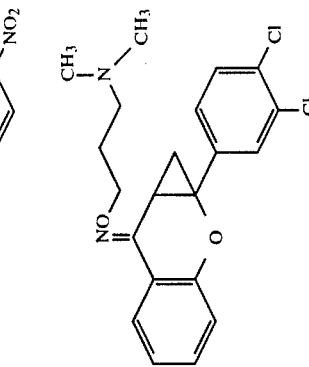 | 93-96 maleate | 2940 2820<br>2770 1618<br>1480 1460<br>1380 1310<br>1210 1130<br>1108 1028<br>980 815 | 1.65(t, 1H, J=6.6Hz)<br>1.83(dd, 1H, J=6.6Hz & 10.6Hz)<br>1.88-1.99(m, 2H)2.25(s, 6H)<br>2.41(t, 1H, J=7.3Hz)<br>3.00(dd, 1H, J=6.6Hz & 10.6Hz)<br>4.2-4.27(m, 2H)<br>6.95-7.05(m, 2H)7.2-7.36(m, 2H)<br>7.47(d, 1H, J=8.6Hz)<br>7.57(d, 1H, J=2.0Hz)<br>7.82(d, 1H, J=8.0Hz) | maleate.4/5H₂O<br>    C   H   N<br>Calc.: 56.04 5.19 5.23<br>Found: 55.85 4.72 5.22 |
| 88 | 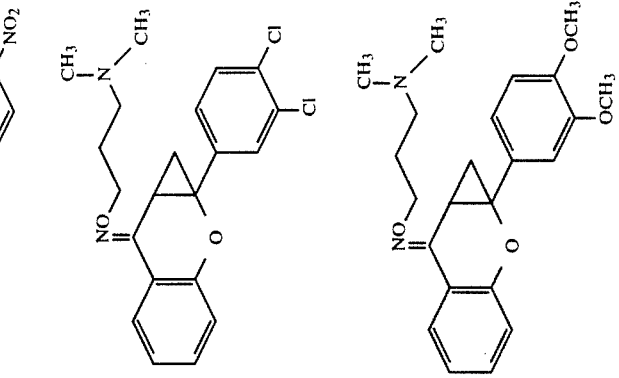 | oil | 2930<br>2800 2750<br>1610 1510<br>1455 1405<br>1370 1305<br>1255 1220<br>1170 1140<br>1020 975<br>900 840<br>800 760 | 1.57(t, 1H, J=6.6Hz)<br>1.83-2.01(m, 3H)2.27(s, 6H)<br>2.43-2.48(m, 2H),<br>2.94-3.07(m, 1H)<br>3.89, 3.93(s, 3H)<br>4.25(t, 2H, J=6.6Hz)<br>6.89-7.36(m, 6H)<br>7.83(d, 1H, J=7.9Hz) | MS<br>396(M⁺) |

| | | | -continued | | |
|---|---|---|---|---|---|
| 89 | 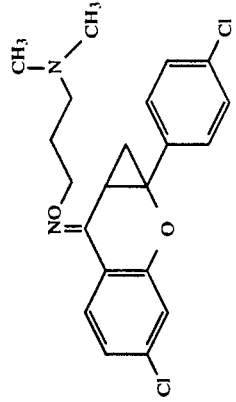 | 140-143 maleate | 2940 2810<br>2760 1615<br>1600 1480<br>1418 1380<br>1310 1225<br>1098<br>1040<br>1010 985<br>920 815<br>760 | 1.59(t, 1H, J=7.3Hz)<br>1.80-2.0(m, 3H)2.24(s, 6H)<br>2.40(t, 2H, J=7.3Hz)<br>2.96(dd, 1H, J=7.3Hz & 10.9Hz)<br>4.15-4.3(m, 2H)6.9-7.0(m, 2H)<br>7.37(s, 4H)7.76(d, 1H) | maleate.½H$_2$O<br>    C   H   N<br>Calc.: 56.60 5.13 5.28<br>Found: 56.63 4.93 5.32 |
| 90 | 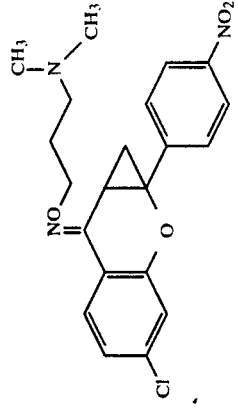 | 159-160 maleate | 3070 2950<br>2820 2760<br>1610 1595<br>1520 1420<br>1350 1230<br>1040 990<br>855 840<br>745 | 1.73(t, 1H, J=6.7Hz)1.95(m, 3H)<br>2.24(s, 6H), 2.38(t, 2H, J=7.9Hz)<br>3.08(dd, 1H, J=6.7Hz & 10.9Hz)<br>4.25(m, 2H)<br>6.97(dd, 1H, J=1.8Hz & 9.7Hz)<br>7.03(d, 1H, J=1.8Hz)<br>7.55(d, 2H, J=9.1Hz)<br>7.77(d, 1H, J=9.7Hz)<br>8.25(d, 2H, J=9.1Hz) | HiMS<br>Calc.: 415.1277<br>Found: 415.1304 |
| 91 | 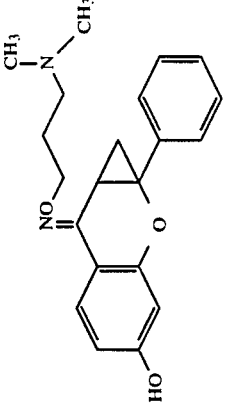 | 64-67 | 3040 2950<br>2860 1610<br>1470 1450<br>1380 1330<br>1260 1160<br>1085 1055<br>1015 995<br>945 890<br>840 830<br>730 695 | 1.54(t, 1H, J=6.9Hz)<br>1.82(dd, 1H, J=6.9Hz & 10.0Hz)<br>1.94-2.04(m, 2H), 2.28(s, 6H)<br>2.47-2.57(m, 2H)<br>2.91(dd, 1H, J=6.9Hz & 10.0Hz)<br>4.12-4.22(m, 2H)<br>6.34-7.53(m, 8H) | MS<br>352(M$^+$) |
| 92 | 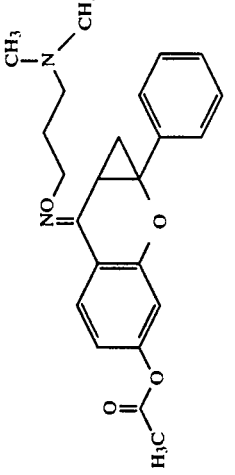 | oil | 2950 2870<br>2820 2770<br>1770 1620<br>1500 1430<br>1370 1200<br>1150 1020<br>960 900<br>750 695 | 1.63(t, 1H, J=6.3Hz)<br>1.90(dd, 1H, J=6.3Hz & 10.5Hz)<br>1.96-2.06(m, 2H)2.28(s, 3H)<br>2.34(s, 6H)<br>2.58(t, 2H, J=7.7Hz)<br>2.97(dd, 1H, J=6.3Hz & 10.5Hz)<br>4.22(t, 2H, J=6.1Hz)<br>6.70-7.85 | HiMS<br>Calc.: 395.1969<br>Found: 395.1929 |

| | | | | |
|---|---|---|---|---|
| 93 | structure | oil | 2950 2880 2820 2770 1735 1625 1610 1440 1395 1260 1030 975 885 810 760 700 | 1.63(t, 1H, J=6.9Hz) 1.92(dd, 1H, J=6.9Hz & 9.9Hz), 2.23-2.34(m, 2H), 2.72(s, 6H), 2.93(dd, 1H, J=6.9Hz & 9.9Hz) 2.98(s, 3H), 3.08(s, 3H) 3.03-3.10(m, 2H), 4.27(t, 2H, J=5.5Hz) 6.74-7.78(m, 8H) | MS 423(M+) |
| 94 | structure | oil | 3300 2940 2860 2820 2770 1690 1610 1505 1435 1390 1345 1260 1240 1175 1095 1050 835 750 690 | 1.58(t, 1H, J=6.3Hz) 1.86-1.98(m, 3H), 2.26(s, 6H) 2.42(t, 2H, J=7.7Hz) 3.00(dd, 1H, J=6.3Hz & 11.0Hz), 4.22(t, 2H, J=6.1Hz)4.48(s, 2H) 5.90(br.s, 2H) 6.48-7.80(m, 8H) | HiMS Calc.: 410.2077 Found: 410.2072 |
| 95 | structure | oil | 3350 2940 1600 1500 1450 1380 1250 1160 1115 1060 1015 980 900 870 810 755 725 695 | 1.58(t, 1H, J=6.6Hz) 1.83(dd, 1H, J=6.6Hz & 10.5Hz) 2.00-2.12(m, 2H), 2.66(s, 6H) 2.88(dd, 1H, J=6.6Hz & 10.5Hz) 2.97-3.03(m, 2H) 4.17-4.25(m, 2H) 6.51(s, 1H) 7.27-7.44(m, 6H) | MS 368(M+) |
| 96 | structure | 75-78 citrate | 2960 2930 2870 2800 1615 1600 1455 1380 1340 1310 1255 1230 1130 1110 1040 980 880 760 740 695 | 1.02(t, 6H, J=7.4Hz) 1.62(t, 1H, J=6.1Hz) 1.85-1.95(m, 3H), 2.52-2.65(m, 6H) 3.01(dd, 1H, J=6.1Hz & 9.9Hz) 4.20-4.26(m, 2H) 6.95-7.84(m, 9H) | HiMs Calc.: 364.2148 Found: 364.2130 |

| # | Structure | mp/form | IR | NMR | MS/Analysis |
|---|---|---|---|---|---|
| 97 | (structure: N,N-diethyl propyl chain, oxime, cyclopropane, phenyl, chromene) | 60–64 L-tartrate | 2950 2860 2800 1610 1600 1450 1380 1340 1305 1250 1230 1070 1030 970 760 740 690 | 0.85(t, 6H, J=7.6Hz) 1.37–1.51(m, 4H) 1.62(t, 1H, J=6.6Hz) 1.80–1.93(m, 3H)2.33–2.39(m, 4H) 2.55(t, 2H, J=7.0Hz) 3.02(dd, 1H, J=6.6Hz & 10.6Hz) 4.23(t, 2H, J=7.0Hz) 6.75–7.48(m, 8H) 7.83(dd, 1H, J=1.3Hz & 7.9Hz) | MS 392(M+) |
| 98 | (structure: pyrrolidine propyl chain, oxime, cyclopropane, phenyl, chromene) | oil | 2980 2890 2800 1620 1610 1490 1460 1390 1350 1320 1260 1240 1180 1140 1120 1050 990 910 880 770 | 1.61(t, 1H, J=6.3Hz) 1.80–1.92(m, 5H) 2.02–2.12(m, 2H) 2.67–2.76(m, 6H) 2.99(dd, 1H, J=6.3Hz & 10.1Hz) 4.25(t, 2H, J=6.1Hz) 6.94–7.82(m, 9H) | HiMs Calc.: 362.1991 Found: 362.1965 |
| 99 | (structure: N-methylpiperazine propyl chain, oxime, cyclopropane, phenyl, chromene) | 184–188 maleate | 2930 2870 2790 1608 1450 1372 1255 1230 1160 1035 1010 975 758 740 | 1.55–1.65(m, 1H) 1.88(dd, 1H, J=6.6Hz & 10.6Hz) 1.85–2.0(m, 2H), 2.28(s, 3H), 2.25–2.60(m, 10H) 3.01(dd, 1H, J=6.6Hz & 10.6Hz) 4.2–4.26(m, 2H) 6.94–7.0(m, 2H) 7.26–7.5(m, 6H) 7.82(dd, 1H, J=2.0Hz & 8.3Hz) | HiMs Calc.: 391.2258 Found: 391.2274 |
| 100 | (structure: piperidine propyl chain, oxime, cyclopropane, phenyl, chromene) | hygroscopic | 2930 2760 1610 1450 1380 1342 1308 1255 1230 1122 1035 980 865 760 742 690 | 1.35–1.7(m, 6H) 1.61(t, 1H, J=6.6Hz) 1.88(dd, 1H, J=6.6Hz & 10.6Hz) 1.85–2.0(m, 2H) 2.3–2.5(m, 6H) 3.01(dd, 1H, J=6.6Hz & 10.6Hz) 4.18–4.26(m, 2H) 6.94–7.0(m, 2H) 7.26–7.50(m, 6H) 7.82(dd, 1H, J=1.3Hz & 7.9Hz) | L-tartrate.3/2H$_2$O Calc.: 60.75 6.74 5.06 Found: 60.56 6.56 4.96 |

| | | | |
|---|---|---|---|
| 101 | 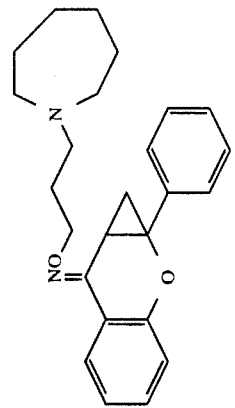 | hygroscopic L-tartrate | 2920 1610 1450 1380 1310 1255 1232 1028 758 741 692 | 1.5-1.75(m, 9H) 1.84-1.97(m, 3H)2.55-2.8(m, 6H) 3.01(dd, 1H, J=6.6Hz & 10.6Hz) 4.23(t, 2H, J=6.6Hz) 6.9-7.0(m, 2H) 7.25-7.5(m, 6H) 7.75-7.85(d, 1H) | L-tartrate.5/4H$_2$O  C H N Calc.: 61.85 6.89 4.98 Found: 61.85 6.73 4.88 |
| 102 | 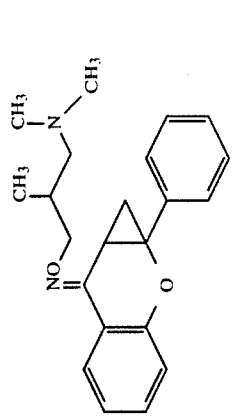 | 118-121 maleate | 2950 2870 2810 2760 1615 1460 1390 1310 1255 1230 1110 1030 980 870 760 745 695 | 1.01(d, 3H, J=4.4Hz) 1.62(t, 1H, J=6.1Hz) 1.87(dd, 1H, J=6.1Hz & 11.0Hz) 2.10-2.30(m, 3H) 2.20, 2.22(s, 3H) 3.02(dd, 1H, J=6.1Hz & 11.0Hz) 3.96-4.04(m, 1H) 4.16-4.24(m, 1H) 6.95-7.84(m, 9H) | maleate.$\frac{1}{4}$H$_2$O  C H N Calc.: 65.66 6.57 5.89 Found: 65.97 6.47 5.87 |
| 103 | 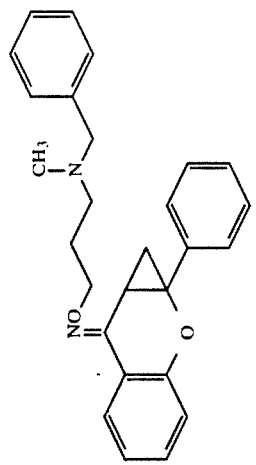 | oil | 2950 2880 2850 2800 1680 1620 1500 1460 1385 1310 1255 1230 1035 980 900 760 740 700 | 1.59(t, 1H, J=6.6Hz) 1.84(dd, 1H, J=6.6Hz & 10.6Hz) 1.91-2.01(m, 2H), 2.21(s, 3H) 2.50(t, 2H, J=7.3Hz) 2.95(dd, 1H, J=6.1Hz & 10.6Hz) 3.50(s, 2H) 4.26(t, 2H, J=5.4Hz) 6.72-7.84(m, 14H) | HiMs Calc.: 412.2147 Found: 412.2134 |
| 104 | | oil | 2930 2870 1690 1680 1615 1600 1450 1380 1310 1285 1250 1230 1030 1010 980 880 760 740 695 | 1.62(t, 1H, J=6.6Hz) 1.82-2.04(m, 5H) 2.36(t, 2H, J=7.9Hz) 3.01(dd, 1H, J=6.6Hz & 7.9Hz) 3.37-3.44(m, 4H) 4.22(t, 2H, J=6.6Hz) 6.75-7.83(m, 9H) | HiMs Calc.: 376.1884 Found: 376.1763 |

| | | | | NMR | HiMs |
|---|---|---|---|---|---|
| 105 | [structure] | 63-67 | 2950 1620 1490 1460 1390 1320 1260 1240 1135 1115 1040 1020 930 810 770 755 740 700 | 1.60(t, 1H, J=6.6Hz), 1.84-2.42(m, 10H), 2.51(t, 1H, J=6.6Hz) 2.86-2.96(m, 2H), 3.22-3.30(m, 3H) 3.75-3.84(m, 1H) 4.31-4.41(m, 1H) 6.91-7.83(m, 9H) | Calc.: 388.2149 Found: 388.2139 |
| 106 | [structure] | oil | 3300 3050 2950 2860 1610 1595 1480 1420 1235 1080 1040 990 750 695 | 1.05(d, 6H, J=7.0Hz)1.59(t, 1H, J=6.4Hz) 1.92(dd, 1H, J=6.4Hz & 10.9Hz), 2.32(br.s, 2H) 2.62(dd, 1H, J=7.7Hz & 12.7Hz) 2.78(m, 2H) 3.02(dd, 1H, J=6.4Hz & 10.9Hz) 4.05(m, 1H)4.22(d, 2H, J=5.8Hz) 6.95(dd, 1H, J=1.9Hz & 7.7Hz) 6.99(d, 1H, J=1.9Hz) 7.28-7.52(m, 5H)7.72(d, 1H, J=7.7Hz) | Calc.: 401.1632 Found: 408.1639 |
| 107 | [structure] | oil | 2430 2950 2780 1620 1605 1460 1235 1040 980 740 | 1.61(t, 1H, J=7.6Hz) 1.72-2.12(m, 5H) 2.60(s, 3H), 2.98(m, 3H) 4.19(t, 2H, J=6.2Hz) 6.97(m, 2H), 7.24-7.52(m, 6H) 7.80(m, 1H, J=7.6Hz) | Calc.: 336.1836 Found: 336.1821 |
| 108 | [structure] | oil | 2940 2850 2800 2750 1610 1600 1450 1380 1250 1230 1040 760 740 690 | 1.62(t, 1H, J=6.4Hz) 1.70-1.82(m, 4H) 1.87(dd, 1H, J=6.4Hz & 10.9Hz) 2.23(s, 6H) 2.32(t, 2H, J=7.1Hz) 3.01(dd, 1H, J=6.4Hz & 10.9Hz) 4.20(t, 2H, J=6.7Hz) 6.72-7.84(m, 9H), | Calc.: 350.1992 Found: 350.1959 |

| | | | | |
|---|---|---|---|---|
| 109 | 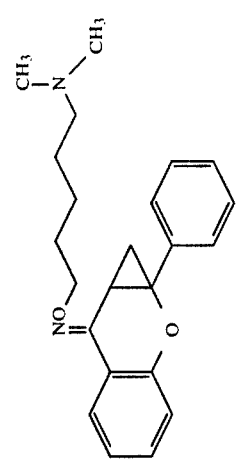 | 103-104 citrate | 2940 2850<br>2750 1615<br>1600 1480<br>1455 1380<br>1310 1255<br>1235 1035<br>860 840<br>690 | 1.37-1.82(m, 7H)<br>1.88(dd, 1H, J=6.4Hz & 10.9Hz)<br>2.21(s, 6H)<br>2.27(t, 2H, J=7.4Hz)<br>3.02(dd, 1H, J=6.4Hz & 10.9Hz)<br>4.18(t, 2H, J=6.4Hz)<br>6.94-7.84(m, 9H) | HiMs<br>Calc.: 364.2148<br>Found: 364.2145 |
| 110 | 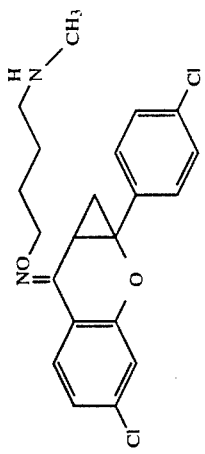 | 91-94 fumarate | 3435 2955<br>2790 1685<br>1615 1415<br>1230 985<br>815 | 1.47(br, 1H)1.61(m, 3H)<br>1.77(m, 2H)<br>1.88(dd, 1H, J=6.6Hz & 10.6Hz)<br>2.42(s, 3H)2.62(t, 2H, J=7.3Hz)<br>3.01(dd, 1H, J=6.6Hz & 10.6Hz)<br>4.21(m, 2H)6.9(m, 2H)<br>7.3(m, 4H)<br>7.82(dd, 1H, J=2.0Hz & 8.6Hz) | fumarate.½H₂O<br>    C    H    N<br>Calc.: 56.61 5.13 5.28<br>Found: 56.35 5.00 5.13 |

TEST EXAMPLE

The compound of the present invention was capable of promoting the extension of nerve dendrites as observed when it was added to a culture cells (NG108-15). Furthermore, it effectively alleviated the defects concerning directional cognition as observed in a model system by performance after the compound had been given to rats suffering from focal resion in the brain, by injection of AF64A into the basal of their forebrain. These effects of the compound of the present invention have been confirmed by the following tests.

(1) Effect of Promoting the Extension of Nerve Dendrites

METHOD

The effect on the extension of nerve dentrites was examined in accordance with a method reported by Nakagawa et al. [Brain Res., 439, 11-18 (1988)]. A specimen was added to NG108-15 cells which had been cultured in Dulbecco's minimum essential medium (DMEM) containing 5% fetal calf serum at 37° C. under 10% $CO_2$. Three days later, the extension of nerve dendrites was observed under a phasecontrast microscope.

RESULTS

Among the test compounds, those produced in Examples 1, 4, 14, 18, 19, 21, 33, 36, 39, 45, 54, 62, 66, 69, 73, 89, 90, 95, 96, 98 and 102 showed an effect of promoting the extension of nerve dendrites when examined at a concentration of from 1 to 15 $\mu M$.

(2) Effect on Morris's Learning Suppression in Water-Labyrinth in an Animal Model Using Rats Suffering from Focal Resion in the Brain Male rats of Fisher strain weighing 290 to 330 g were used. The focal resion (destruction) in the brain were formed in accordance with a method described in Behav. Brain Res., 19, 119-126 (1988). Training was initiated 1 week after the destruction by using a stainless cylindrical vessel (diameter: 132 cm, depth: 60 cm). On the first day of the training, each test animal was allowed to swim freely for 60 seconds without providing any platforms. From the next day, a labyrinth test was performed for 4 days. On the fifth day, a transfer test was performed for 60 seconds without providing any platform so as to examine whether the animal remembered the location of the platform or not. The test items involved (1) the time required for the animal to reach the platform; (2) the residence time in the quarter circle were the platform had been provided; and (3) the frequency at which the animal crossed the place where the platform had been provided.

RESULTS

Among the test compounds, those produced in Examples 33 and 45 significantly prevented the aforesaid Morris's learning suppression in water-labyrinth, when administered continuously in a dose of 10 mg/kg. The improvement was confirmed by intraperitoneal as well as oral administration.

FORMULATION EXAMPLE 1 (capsule)

10 g of the compound of the present invention, 165 g of corn starch, 164 g of crystalline cellulose and 1 g of magnesium stearate were uniformly mixed together and then filled in hard gelatin capsules.

Each capsule comprised the following composition.

| | |
|---|---|
| compound of the invention | 10 mg |
| corn starch | 165 mg |
| crystalline cellulose | 164 mg |
| magnesium stearate | 1 mg |
| | 340 mg |

FORMULATION EXAMPLE 2 (tablet)

1 g of the compound of the present invention, 150 g of lactose, 14 g of corn starch, 4 g of polyvinylpyrrolidone and 2 g of magnesium stearate were uniformly mixed together and formulated into tablets by direct-tableting method.

Each tablet comprised the following composition.

| | |
|---|---|
| compound of invention | 10 mg |
| lactose | 150 mg |
| corn starch | 14 mg |
| polyvinylpyrrolidone (K90) | 4 mg |
| magnesium stearate | 2 mg |
| | 180 mg |

FORMULATION EXAMPLE 3 (INJECTION)

1 g of the compound of the present invention and 50 g of mannitol were dissolved in purified water in such a manner as to adjust the total volume to 1000 ml. The obtained solution was aseptically filled in glass ampuls.

This injection comprised the following composition per ampul.

| | |
|---|---|
| compound of invention | 1 mg |
| mannitol | 50 mg |
| purified water | balance |
| | 1 ml |

As described above, the therapeutic agent of the present invention, which promotes the compensatory recovery of the function of a degenerated neuro-circuit, is an epochmaking drug based on a novel conception depending on the plasticity of synapses in the brain nerves and a learning behavior level. The active ingredient of the therapeutic agent of the present invention can be easily and economically synthesized in order to consistently supply commercial products.

While the invention has been described in detail and with reference to specific examples thereof, it will be apparent to one skilled in the art that various changes and modifications can be made therein without departing from the spirit and scope thereof.

What is claimed is:

1. A method for alleviating a disorder due to atrophic nerve cell degeneration in the brain comprising administering to a patient suffering from said disorder a cyclopropachromen derivative in an amount sufficient to alleviate the symptoms of said disease, wherein the derivative is represented by the general formula (I)

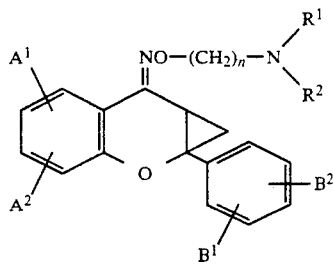

(I)

wherein
n is an integer of from 2 to 5;
the carbon atom is the —(CH$_2$)— moiety may be optionally substituted with a methyl group or a hydroxyl group;
R$^1$ and R$^2$ independently represent a hydrogen atom, an alkyl group having 1 to 5 carbon atoms, a phenyl group or an aralkyl group having 7 to 10 carbon atoms; or alternatively R$^1$ and R$^2$ form together with the nitrogen atom to which they are attached, a morpholino group, a thiomorpholino group, a pyrrolidinyl group, a piperidinyl group, a homopiperidinyl group, a piperazinyl group, a homopiperazinyl group, an N-alkylpiperazinyl group, N-alkylhomopiperazinyl group, an N-hydroxyalkylpiperazinyl group or a pyrrolidonyl group or alternatively R$^1$ and R$^2$ form together with the nitrogen atom to which they are attached, and further a carbon atom to which said nitrogen atom is bound, a pyrrolitidinyl group;
A$^1$ and A$^2$ independently represent a hydrogen atom, a hydroxyl group, a halogen atom, an optionally halogenated alkyl group having 1 to 5 carbon atoms, an optionally substituted alkoxy group, an acyloxy group, a carbamyloxy group or an optionally substituted carboxyl group; and
B$^1$ and B$^2$ independently represent a hydrogen atom, a halogen atom, a nitro group, a cyano group, an optionally halogenated alkyl group having 1 to 5 carbon atoms, an alkoxy group having 1 to 5 carbon atoms or an optionally substituted carboxyl group; or a pharmaceutically acceptable salt thereof as an active ingredient, together with a pharmaceutical carrier or adjuvant.

2. A method as claimed in claim 1 wherein the cyclopropachromen derivative is administered in a dose between 0.1 and 1,000 mg per day via oral administration, intravenous injection or application to mucosa.

3. A method as claimed in claim 1 wherein the cyclopropachromen derivative is administered in a dose between 0.1 and 500 mg per day.

4. A method as claimed in claim 1 wherein said derivative is administered in a dose between 1 and 500 mg per day.

5. A method as claimed in claim 1 wherein one of R$^1$ and R$^2$ in the general formula (I) represents a hydrogen atom and the other represents an alkyl group having 1 to 5 carbon atoms, a phenyl group or an aralkyl group having 7 to 10 carbon atoms.

6. A method as claimed in claim 1 wherein one of A$^1$ and A$^2$ in the general formula (I) represents a hydrogen atom and the other represents a hydroxyl group, a halogen atom, an optionally halogenated alkyl group having 1 to 5 carbon atoms, an optionally substituted alkoxy group, an acyloxy group, a carbamyloxy group or an optionally substituted carboxyl group.

* * * * *